(12) United States Patent
Takata et al.

(10) Patent No.: US 8,383,831 B2
(45) Date of Patent: Feb. 26, 2013

(54) DYE FOR DYE-SENSITIZED SOLAR CELL, SEMICONDUCTOR ELECTRODE, AND DYE-SENSITIZED SOLAR CELL

(75) Inventors: Masakazu Takata, Tokyo (JP); Koichi Sumioka, Tokyo (JP); Takaaki Kozai, Tokyo (JP)

(73) Assignee: Mitsubishi Paper Mills Limited, Tokyo (JP)

( * ) Notice: Subject to any disclaimer, the term of this patent is extended or adjusted under 35 U.S.C. 154(b) by 86 days.

(21) Appl. No.: 13/057,222

(22) PCT Filed: Aug. 5, 2009

(86) PCT No.: PCT/JP2009/064213
§ 371 (c)(1),
(2), (4) Date: Feb. 25, 2011

(87) PCT Pub. No.: WO2010/016612
PCT Pub. Date: Feb. 11, 2010

(65) Prior Publication Data
US 2011/0155241 A1    Jun. 30, 2011

(30) Foreign Application Priority Data
Aug. 6, 2008  (JP) .................................. 2008-202483

(51) Int. Cl.
*H01L 31/0224* (2006.01)
*H01L 51/46* (2006.01)
*C07D 417/14* (2006.01)

(52) U.S. Cl. ........ 548/181; 136/256; 136/263; 548/490; 548/439

(58) Field of Classification Search .................... 548/181
See application file for complete search history.

(56) References Cited

U.S. PATENT DOCUMENTS

| 7,795,529 B2 * | 9/2010 | Horiuchi et al. ............. 136/263 |
| 2004/0099306 A1 | 5/2004 | Hara et al. |
| 2004/0256002 A1 | 12/2004 | Horiuchi et al. |

FOREIGN PATENT DOCUMENTS

| JP | 10-092477 | 4/1998 |
| JP | 11-238905 | 8/1999 |
| JP | 2001-076773 | 3/2001 |
| JP | 2005-019252 | 1/2005 |
| JP | 2008-16383 | 1/2006 |
| JP | 2006-286609 | 10/2006 |
| JP | 2007-048672 | 2/2007 |
| JP | 2007-048680 | 2/2007 |
| JP | 2007-095584 | 4/2007 |
| JP | 2007-115673 | 5/2007 |
| JP | 2008-277206 | 10/2007 |
| JP | 2009-176526 | 8/2009 |
| JP | 2009-187738 | 8/2009 |
| WO | 02/45199 | 6/2002 |
| WO | 2004/011555 | 2/2004 |

OTHER PUBLICATIONS

Horiuchi et al., Journal of the American Chemical Society (2004), 126(39), pp. 12218-12219.*
International Search Report issued Nov. 17, 2009 in International (PCT) Application No. PCT/JP2009/064213 along with the Written Opinion.
B. O'Regan et al., "A Low-Cost, High-Efficiency Solar Cell Based on Dye-Sensitized Colloidal $TiO_2$ Films", Nature, vol. 353, pp. 737-740, Oct. 24, 1991.

* cited by examiner

*Primary Examiner* — Laura L. Stockton
(74) *Attorney, Agent, or Firm* — Wenderoth, Lind & Ponack, L.L.P.

(57) ABSTRACT

The dye for a dye-sensitized solar cell, which dye is a compound classified into melocyanine dyes and has a structure in which an electron donor unit and an electron acceptor unit are connected with conjugated double bonds, provided by this invention, has excellent photoelectric conversion efficiency and excellent durability, and according to this invention, there can be provided a semiconductor electrode sensitized by the dye and a dye-sensitized solar cell using the semiconductor electrode.

3 Claims, No Drawings

DYE FOR DYE-SENSITIZED SOLAR CELL, SEMICONDUCTOR ELECTRODE, AND DYE-SENSITIZED SOLAR CELL

This application is a U.S. national stage of International Application No. PCT/JP2009/064213 filed Aug. 5, 2009.

TECHINCAL FIELD

This invention relates to a dye for a dye-sensitized solar cell, a semiconductor electrode and a dye-sensitized solar cell.

BACKGROUND ART

It has come to be recognized that global warming caused by an increase in carbon dioxide concentration driven by the use of a large amount of fossil fuels and an increase in energy demands driven by population growth have posed problems of annihilation of the human species. In recent years, therefore, studies are being energetically made for the utilization of sunlight that is infinite and free from the occurrence of harmful substances. For utilizing the above sunlight that is a clean energy source, there are practically used inorganic solar cells for residential buildings, such as a solar cell of single crystal silicon, polycrystal silicon, amorphous silicon, cadmium telluride and indium copper selenide.

However, these inorganic solar cells have defects. For example, silicon-based solar cells require silicon having very high purity, and naturally, the purification step thereof is complicated and requires a large number of processes, and a production cost is high. Besides these, a lightening of the cells is also required, and in particular, disadvantageously, it takes a long period of redemption for users for all the cost. They have problems that hinder the spread thereof.

On the other hand, many solar cells using organic materials have been proposed. The organic solar cells include a Schottky type photoelectric conversion device having a junction formed by a p-type organic semiconductor and a metal having a small work function and a hetero-junction type photoelectric conversion device having a junction formed by a p-type organic semiconductor and an n-type inorganic semiconductor or a junction formed by a p-type organic semiconductor and an electron-accepting organic compound. The organic semiconductor used contains a material selected from synthetic dyes or pigments such as chlorophyll, perylene, etc., electrically conductive polymer materials such as polyacetylene, etc., or composite materials of these. A thin film is formed from any one of these materials by a vacuum vapor deposition method, a casting method, a dipping method, on the like to constitute cell materials. The organic materials have advantages that their cost is low and that a large area is easily formed, while they have problems that many of them exhibit a conversion of 1% or less, and that they are poor in durability.

Under the circumstances, a solar cell that exhibits excellent characteristics has been reported by Dr. Michael Graezel of Switzerland, etc., (for example, see Non-Patent Document 1). Further, this Document also discloses materials and production technique, which are necessary for producing the cell. This solar cell is called a dye-sensitized solar cell or Graezel type solar cell, and it is a wet solar cell using, as a working electrode, a porous thin film of titanium oxide spectrally sensitized with a ruthenium (Ru) complex. This system has the following advantages; It is not required to purify a semiconductor of a less expensive oxide such as titanium oxide until it has a high purity, so that the cells are less expensive, and light that can be utilized covers up to a broad visible light region, so that sunlight containing a large quantity of visible light components can be effectively converted to electricity.

However, due to the use of Ru that is a resource-constrained noble metal, the reliable supply of Ru complex cannot be expected when dye-sensitized solar cells are practically used in the near future. Further, since Ru complex is expensive due to resource constraint, the improvement is required in view of mass production. For overcoming these problems, there have been made a variety of proposals for at least partially replacing Ru complex with less expensive organic dyes. As examples therefor, various melocyanine dyes, cyanine dyes, 9-phenylxanthene dyes, coumarin dyes, etc., have been disclosed, while they are considerably inferior to Ru complex in photoelectric conversion efficiency. Also, they have problem about stable adsorption to a semiconductor, and most of them have little practicability (for example, see Patent Documents 1-4).

Recently, organic dyes having high photoelectric conversion efficiency comparable to that of Ru complex have been recently disclosed as dye-sensitizer for dye-sensitized solar cells (for example, see Patent Documents 5, 6 and 11). These organic dyes are compounds that are classified into a melocyanine dye. Melocyanine dyes have a structure in which a unit having an electron-donating substituent (to be referred to as "electron-donor unit" hereinafter) and a unit having an electron-accepting substituent (to be referred to as "electron acceptor unit" hereinafter) are bonded through conjugated double bonds. When a melocyanine dye is used as a dye-sensitizer for a dye-sensitized solar cell, the dye has an acidic group that promotes the adsorption to a semiconductor onto its electron acceptor unit in general. However, the organic dyes described in Patent Documents 5, 6 and 11 cannot adsorb to semiconductors stably in practical use. Most of them hence have the property with a problem that the dye is re-dissolved in an electrolyte with the passage of time when a dye-sensitized solar cell is stored.

There have been disclosed trials to improve adsorption stability to a semiconductor in order to overcome the above re-dissolving problem and to improve stability (durability) with the passage of time (for example, see Patent Documents 7-10 and 12).

In Patent Document 7, two molecules of melocyanine dye are bonded together in electron donor unit to form a dye dimer, so that the adsorption stability is improved. However, the dye dimer is very insoluble to any organic solvent, therefore which it is difficult to purify the dye dimer, and the photoelectric conversion efficiency of the cell applied it thereof is insufficient.

Patent Document 8 proposes a melocyanine dye having two acidic groups which promote adsorption to semiconductor in a specific site of an electron acceptor unit. However, the synthesis of the electron acceptor unit having two acidic groups is complicated, and it has been difficult to produce the dye in a large amount.

Patent Document 9 proposes a melocyanine dye having one adsorption-promoting acid group in an electron donor unit and one adsorption-promoting acid group in an electron acceptor unit. Since, however, the one acidic group is present in the vicinity of an electron-donating substituent, the injection efficiency of electrons from a photo-excited melocyanine dye to a semiconductor is decreased, and therefore the photoelectric conversion efficiency of the cell is insufficient.

Patent Document 10 proposes a melocyanine dye in which two electron acceptor units are connected to one electron doner unit. However, the dye molecules have low symmetry, and the injection efficiency of electrons from a photo-excited melocyanine dye to a semiconductor is decreased, so that the photoelectric conversion efficiency of the cell is not so high.

In Patent Document 12, two molecules of a melocyanine dye are bonded together in an electron acceptor unit portion to form a dye dimer, so that the adsorption stability is improved. This dye dimer is excellent in both adsorption stability to a semiconductor and photoelectric conversion efficiency. Since, however, the synthesis of a dye intermediate is very complicated, it is difficult to produce the dye in a large amount.

From the viewpoint of production of more practical solar cells, therefore, there are demanded further improvements in photoelectric conversion efficiency, durability and facilitation of the production.

[Prior Art Documents]
[Patent Documents]
[Patent Document 1] JP 11-238905 A
[Patent Document 2] JP 2001-76773 A
[Patent Document 3] JP 10-92477 A
[Patent Document 5] Japanese Translation Version No. 2002/045199 of PCT application
[Patent Document 6] Japanese Translation Version No. 2004/011555 of PCT application
[Patent Document 6] JP 2005-19252 A
[Patent Document 7] JP 2006-286609 A
[Patent Document 8] JP 2007-48672 A
[Patent Document 9] JP 2007-48680 A
[Patent Document 10] JP 2007-95584 A
[Patent Document 11] JP 2007-115673 A
[Patent Document 12] JP 2008-16383 A
[Non-patent Document]
[Non-patent Document 1] Nature, 353, 737 (1991)

SUMMARY OF THE INVENTION

Problems to be Solved by the Invention

It is an object of this invention to provide a dye for a dye-sensitized solar cell which dye has excellent photoelectric conversion efficiency and durability and can be easily produced, a semiconductor electrode sensitized by the above dye for a dye-sensitized solar cell and a dye-sensitized solar cell using the semiconductor electrode.

Means to Solve the Problems

For achieving the above object, the present inventors have made diligent studies, and as a result have overcome the problems by a dye for a dye-sensitized solar cell, represented by the general formula [I], [II], [III] or [IV] (to be referred to as "dye" hereinafter), a semiconductor electrode sensitized by this dye, and a dye-sensitized solar cell using the semiconductor electrode.

[CF1]

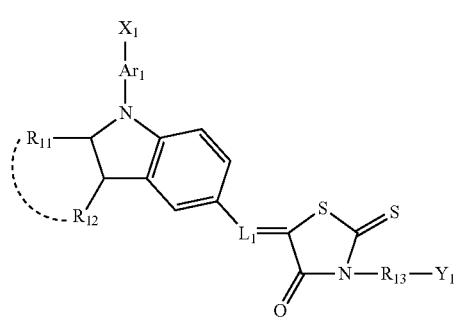

In the general formula [I], each of $R_{11}$ and $R_{12}$ represents a hydrogen atom or an alkyl group, and these two substituents may be bonded to each other and form a cyclopentane ring or a cyclohexane ring. $Ar_1$ represents a divalent aromatic hydrocarbon residue or a divalent heterocyclic ring residue. $X_1$ represents a residue having an acidic group possessing a pKa of less than 6 bonded through an alkylene group having 4 or more carbon atoms. $L_1$ represents a conjugated methine group unit. $R_{13}$ represents an alkylene group having 1 to 3 carbon atoms. $Y_1$ is an acidic group possessing a pKa of less than 6.

[CF2]

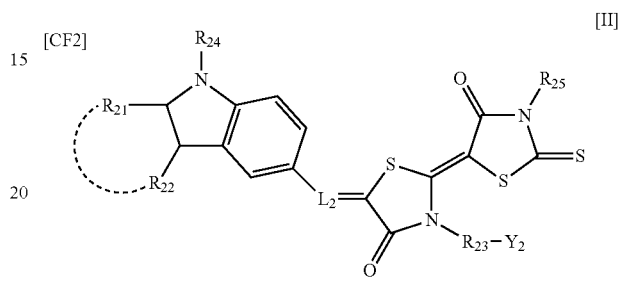

In the general formula [II], each of $R_{21}$ and $R_{22}$ represents a hydrogen atom or an alkyl group, and these two substituents may be bonded to each other and form a cyclopentane ring or a cyclohexane ring. $R_{23}$ represents an alkylene group having 1 to 3 carbon atoms. $Y_2$ represents an acidic group possessing a pKa of less than 6. $R_{24}$ represents an aliphatic hydrocarbon residue, an aromatic hydrocarbon residue or a heterocyclic ring residue. $R_{25}$ represents an alkyl group or an aralkyl group. However, at least one of $R_{24}$ and $R_{25}$ has an acidic group possessing a pKa of less than 6 bonded through an alkylene group having 4 or more carbon atoms. $L_2$ represents a conjugated methine group unit. The steric configuration of two heterocyclic five-membered rings containing a sulfur atom each may be any one of Z-configuration and E-configuration.

[CF3]

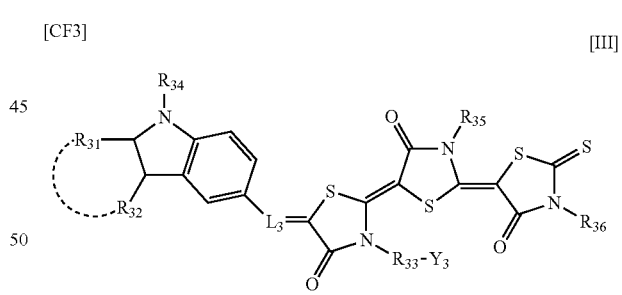

In the general formula [III], each of $R_{31}$ and $R_{32}$ represents a hydrogen atom or an alkyl group, and these two substituents may be bonded to each other and form a cyclopentane ring or a cyclohexane ring. $R_{33}$ represents an alkylene group having 1 to 3 carbon atoms. $Y_3$ represents an acidic group possessing a pKa of less than 6. $R_{34}$ represents an aliphatic hydrocarbon residue, an aromatic hydrocarbon residue or a heterocyclic ring residue. Each of $R_{35}$ and $R_{36}$ represents an alkyl group or an aralkyl group. However, at least one of $R_{34}$, $R_{35}$ and $R_{36}$ contains an acidic group possessing a pKa of less than 6 bonded through an alkylene group having 4 or more carbon atoms. $L_3$ represents a conjugated methine group unit. The combination of steric configurations of the three heterocyclic five-membered rings containing a sulfur atom each may be any one of (ZZ) configuration, (ZE) configuration, (EZ) configuration and (EE) configuration.

[CF4]

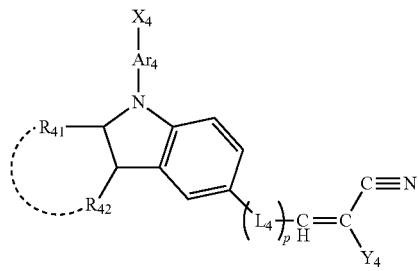

[IV]

In the general formula [IV], each of $R_{41}$ and $R_{42}$ represents a hydrogen atom or an alkyl group, and these two substituents may be bonded to each other and form a cyclopentane ring or a cyclohexane ring. $Ar_4$ represents a divalent aromatic hydrocarbon residue or a divalent heterocyclic ring residue. $X_4$ represents a residue having an acidic group possessing a pKa of less than 6 bonded through an alkylene group having 4 or more carbon atoms. $L_4$ represents a divalent binding group, and p represents 0 or 1. $Y_4$ represents a carboxyl group, an ammonium salt of carboxyl group or an alkali metal salt of carboxyl group.

Effect Of the Invention

The dye of general formula [I], [II], [III] or [IV] is a compound classified into melocyanine dyes, and has a structure in which an electron donor unit and an electron acceptor unit are connected through conjugated double bonds. The dye of this invention has in the same molecule at least two acidic groups that promote adsorbability to a semiconductor. Therefore, dye molecules can be efficiently adsorbed to a semiconductor to improve durability.

Further, high photoelectric conversion efficiency could be achieved by arranging a first acidic group that promotes absorbability to a semiconductor (acidic group bonded to an electron acceptor unit through an alkylene group possessing a pKa of less than 6 having 1 to 3 carbon atoms; carboxyl group, ammonium salt of carboxyl group or alkali metal salt of carboxyl group) in a specific site (—$R_{13}$—$Y_1$ in the general formula [I], —$R_{23}$—$Y_2$ in the general formula [II], —$R_{33}$—$Y_3$ in the general formula [III]; —$Y_4$ in the general formula [IV]), and arranging a second acidic group (acidic group possessing a pKa of less than 6 bonded through an alkylene group having 4 or more carbon atoms) in a specific site ($X_1$ in the general formula [I], at least one of $R_{24}$ and $R_{25}$ in the general formula [II], at least one of $R_{34}$, $R_{35}$ and $R_{36}$ in the general formula [III] or $X_4$ in the general formula [IV]). While the reason therefor is not clear, it is assumed that there is exhibited a barrier effect that the direct contact between a semiconductor and an electrolyte is reduced owing to a steric effect that the alkylene group having 4 or more carbon atoms has, and that, consequently, the back transition of electrons between a semiconductor and an electrolyte can be effectively prevented during the working of cells. Further, it is assumed that since an acidic group possessing a pKa of less than 6 is bonded to a dye through a long-chain alkylene group having 4 or more carbon atoms, the distance between the second acidic group and the conjugated double bonds of a dye skeleton can be made larger, and that, consequently, the negative effect that the second acidic group has on the electron state of the dye can be decreased to a great extent.

It has been found that the effects of the first acidic group and the second acidic group differ depending upon their arrangement sites in a dye molecule, and that the acidic groups in only combinations of the arrangement sites in this invention have performances both of prevention of re-elution of the dye in an electrolyte during storage with time and excellent photoelectric conversion efficiency. It has been also found that when the alkylene group in the second acidic group has less than 4 carbon atoms, or when the alkylene group in the first acidic group has more carbon atoms than the specified number, the effect on prevention of re-elution into an electrolyte is exhibited, but no high photoelectric conversion efficiency can be accomplished.

Further, the dye of this invention can be synthesized by consecutively connecting dye intermediates having acidic groups, so that it can be easily synthesized and purified as compared with conventional organic dyes.

The dye of this invention is excellent in production simplicity, and a semiconductor electrode and a dye-sensitized solar cell which use the dye of this invention have excellent photoelectric conversion efficiency and durability.

PREFERRED EMBODIMENTS OF THE INVENTION

The dye of the general formula [I], [II], [III] or [IV] will be explained.

In the general formula [I], each of $R_{11}$ and $R_{12}$ represents not only a hydrogen atom but also an alkyl group such as methyl, ethyl, n-butyl, n-octyl, etc., and these two substituents may be bonded to each other and form a cyclopentane ring or a cyclohexane ring. Particularly preferably, these two substituents may be bonded to each other and form a cyclopentane ring or a cyclohexane ring.

$Ar_1$ represents a divalent aromatic hydrocarbon residue or a divalent heterocyclic ring residue. Examples of $Ar_1$ include the following, while it shall not be limited thereto.

[CF1]

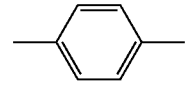

AR-1

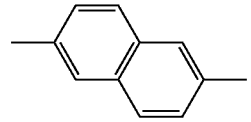

AR-2

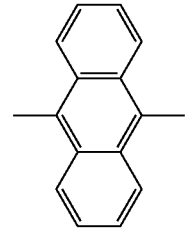

AR-3

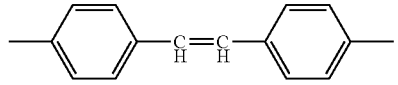

AR-4

AR-5
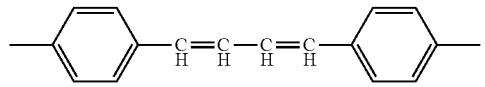

AR-6
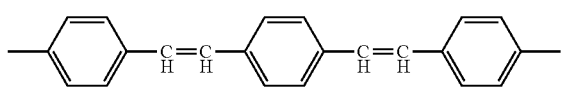

AR-7
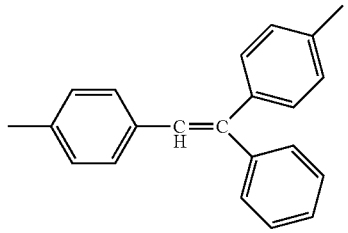

AR-8
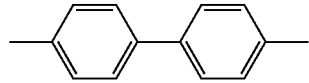

AR-9
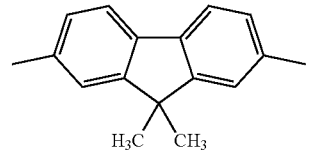

AR-10
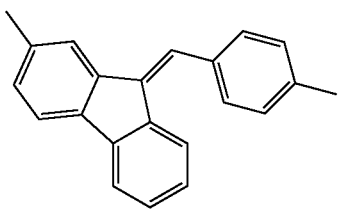

[CF6]

HR-1

HR-2
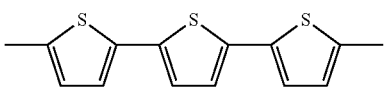

HR-3
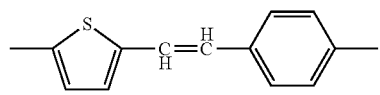

HR-4

HR-5
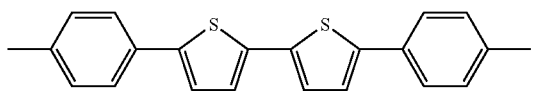

HR-6

HR-7

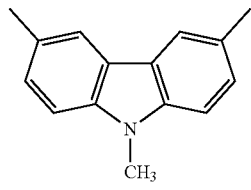

$X_1$ represents a residue having an acidic group possessing a pKa of less than 6 bonded through an alkylene group having 4 or more carbon atoms. The upper limit of the number of carbon atoms is preferably 22. Examples of the acidic group possessing a pKa of less than 6 include a carboxyl group, a sulfo group, a sulfino group, a sulpheno group, a phosphono group and a phosphinico group. Of these, a carboxyl group is particularly preferred. Further, the acidic group possessing a pKa of less than 6 may be a free acid, and it may be also a salt (e.g., ammonium salts such as ammonium salt, trimethylammonium salt, triethylammonium salt, tetra-n-butylammonium salt, etc., or alkali metal salts such as lithium salt, sodium salt, potassium salt, etc.). Specific examples of $X_1$ preferably include the following, while it shall not be limited thereto. Y is an acidic group possessing a pKa of less than 6.

[CF7]

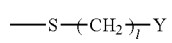     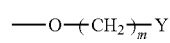

| AC-1 | $l=4$ | AC-11 | $l=14$ | AC-21 | $m=4$ | AC-31 | $m=14$ |
|---|---|---|---|---|---|---|---|
| AC-2 | $l=5$ | AC-12 | $l=15$ | AC-22 | $m=5$ | AC-32 | $m=15$ |
| AC-3 | $l=6$ | AC-13 | $l=16$ | AC-23 | $m=6$ | AC-33 | $m=16$ |
| AC-4 | $l=7$ | AC-14 | $l=17$ | AC-24 | $m=7$ | AC-34 | $m=17$ |
| AC-5 | $l=8$ | AC-15 | $l=18$ | AC-25 | $m=8$ | AC-35 | $m=18$ |
| AC-6 | $l=9$ | AC-16 | $l=19$ | AC-26 | $m=9$ | AC-36 | $m=19$ |
| AC-7 | $l=10$ | AC-17 | $l=20$ | AC-27 | $m=10$ | AC-37 | $m=20$ |
| AC-8 | $l=11$ | AC-18 | $l=21$ | AC-28 | $m=11$ | AC-38 | $m=21$ |
| AC-9 | $l=12$ | AC-19 | $l=22$ | AC-29 | $m=12$ | AC-39 | $m=22$ |
| AC-10 | $l=13$ | AC-20 | $l=23$ | AC-30 | $m=13$ | AC-40 | $m=23$ |

| AC-41 | $n=4$ | AC-51 | $n=14$ |
|---|---|---|---|
| AC-42 | $n=5$ | AC-52 | $n=15$ |
| AC-43 | $n=6$ | AC-53 | $n=16$ |
| AC-44 | $n=7$ | AC-54 | $n=17$ |
| AC-45 | $n=8$ | AC-55 | $n=18$ |
| AC-46 | $n=9$ | AC-56 | $n=19$ |
| AC-47 | $n=10$ | AC-57 | $n=20$ |
| AC-48 | $n=11$ | AC-58 | $n=21$ |
| AC-49 | $n=12$ | AC-59 | $n=22$ |
| AC-50 | $n=13$ | AC-60 | $n=23$ |

[CF8]

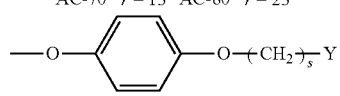

| AC-61 | r = 4 | AC-71 | r = 14 |
| AC-62 | r = 5 | AC-72 | r = 15 |
| AC-63 | r = 6 | AC-73 | r = 16 |
| AC-64 | r = 7 | AC-74 | r = 17 |
| AC-65 | r = 8 | AC-75 | r = 18 |
| AC-66 | r = 9 | AC-76 | r = 19 |
| AC-67 | r = 10 | AC-77 | r = 20 |
| AC-68 | r = 11 | AC-78 | r = 21 |
| AC-69 | r = 12 | AC-79 | r = 22 |
| AC-70 | r = 13 | AC-80 | r = 23 |

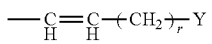

| AC-81 | s = 4 | AC-91 | s = 14 |
| AC-82 | s = 5 | AC-92 | s = 15 |
| AC-83 | s = 6 | AC-93 | s = 16 |
| AC-84 | s = 7 | AC-94 | s = 17 |
| AC-85 | s = 8 | AC-95 | s = 18 |
| AC-86 | s = 9 | AC-96 | s = 19 |
| AC-87 | s = 10 | AC-97 | s = 20 |
| AC-88 | s = 11 | AC-98 | s = 21 |
| AC-89 | s = 12 | AC-99 | s = 22 |
| AC-90 | s = 13 | AC-100 | s = 23 |

$L_1$ is a conjugated methine group, and it is constituted of a conjugated methine chain having an odd number of carbon atom(s). The number of carbon atoms is preferably 1 or 3, and a monomethine group having 1 carbon atom is particularly preferred.

$R_{13}$ is an alkylene group having 1 to 3 carbon atoms. It is preferably an alkylene group having 1-2 carbon atoms. $Y_1$ represents an acidic group possessing a pKa of less than 6. Examples of the acidic group possessing a pKa of less than 6 include those described as examples with regard to $X_1$.

In the general formula [II], each of $R_{21}$ and $R_{22}$ represents a hydrogen atom or an alkyl group, and these two substituents may be bonded to each other and form a cyclopentane ring or a cyclohexane ring. Examples of $R_{21}$ and $R_{22}$ are as described as examples of $R_{11}$ and $R_{12}$ in the general formula [I].

$R_{23}$ represents an alkylene group having 1 to 3 carbon atoms. Above all, an alkylene group having 1-2 carbon atoms is particularly preferred. $Y_2$ represents an acidic group possessing a pKa of less than 6. Examples of the acidic group possessing a pKa of less than 6 are as described with regard to $X_1$ in the general formula [1].

$R_{24}$ represents an aliphatic hydrocarbon residue, an aromatic hydrocarbon residue or a heterocyclic ring residue. Specific examples of the aliphatic hydrocarbon residue include alkyl groups such as methyl, ethyl, propyl, octyl, etc., alkenyl groups such as allyl, butenyl, etc., alkynyl groups such as propargyl, etc., and aralkyl groups such as benzyl, phenethyl, etc. Specific examples of the aromatic hydrocarbon residue include phenyl, tolyl, naphthyl, etc. Specific examples of the heterocyclic ring residue include indolyl, pyridyl, furyl, thienyl, etc. Of these, aromatic hydrocarbon residues are particularly preferred. These aliphatic hydrocarbon residue, aromatic hydrocarbon residue and heterocyclic ring residue may further have various substituents substituted thereon. Examples of the substituents include the above aliphatic hydrocarbon residues, aromatic hydrocarbon residues and heterocyclic ring residues, and besides these, the above examples also include an amino group, a vinyl group, an alkoxy group, an aryloxy group, an alkylthio group, an arylthio group, a hydroxyl group, a halogen atom and an acidic group possessing a pKa of less than 6.

Of the specific examples of the aromatic hydrocarbon residue represented by $R_{24}$, the following are particularly preferred, while the aromatic hydrocarbon residue shall not be limited thereto.

[CF9]

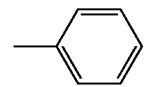
AS-1

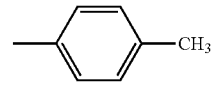
AS-2

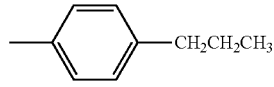
AS-3

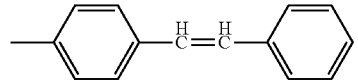
AS-4

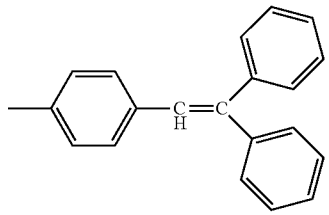
AS-5

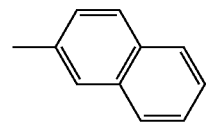
AS-6

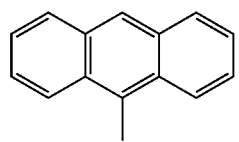
AS-7

AS-8

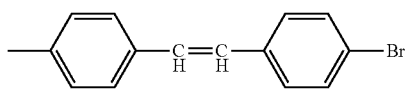
AS-9

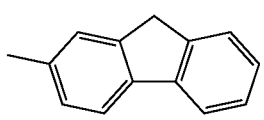
AS-10

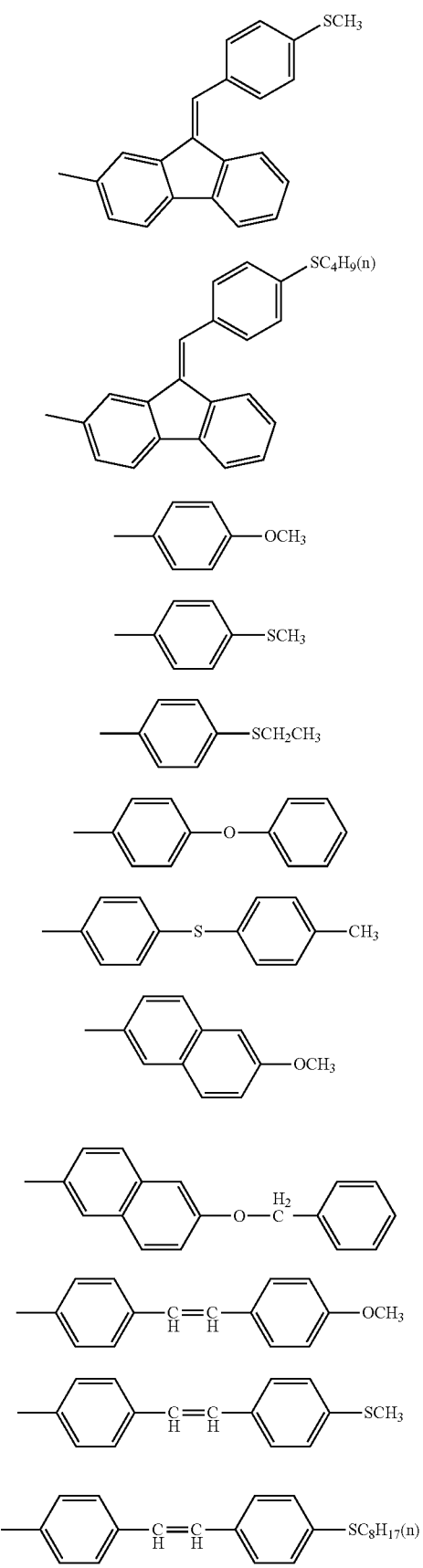
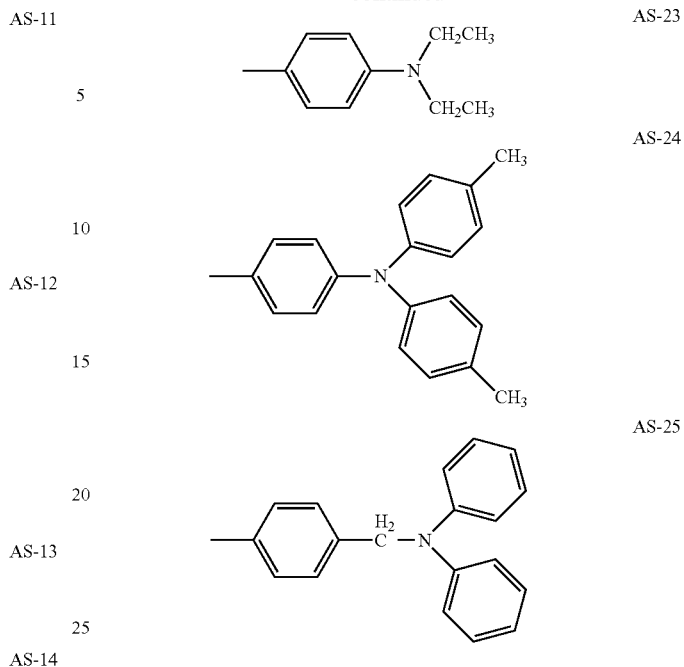

Those which exhibit remarkably preferred properties of photoelectric conversion efficiency among them are AS-5, AS-10 to AS-14, AS-20 to AS-22, etc.

$R_{25}$ represents an alkyl group or an aralkyl group. The alkyl group includes methyl, ethyl, propyl, octyl, pentyl, hexyl, octyl, decyl, dodecyl, etc. These may have a linear or branched structure. An alkyl group having a linear structure and having 5 or more but 14 or less carbon atoms is particularly preferred. The aralkyl group includes benzyl, phenethyl, 1-naphthyl, etc.

At least one of $R_{24}$ and $R_{25}$ has an acidic group possessing a pKa of less than 6 bonded through an alkylene group having 4 or more carbon atoms. Examples of the acidic group possessing a pKa of less than 6 bonded through an alkylene group having 4 or more carbon atoms include the above AC-41 to AC-60. The upper limit of number of carbon atoms is preferably 22. Of these, an acidic group possessing a pKa of less than 6 that is bonded to an alkylene group having 4 or more but 14 or less carbon atoms having a linear structure is particularly preferred. Examples of the acidic group possessing a pKa of less than 6 are similar to that described with regard to $X_1$ in the general formula [I]. Table 1 shows arrangements of acidic groups in the dye of the general formula [II]. In combinations in Table 1, a preferred order is A>B>D>C.

TABLE 1

| Combination | $R_{24}$ | $R_{25}$ |
|---|---|---|
| A | Having no acidic group possessing a pKa of less than 6 bonded through alkylene group having 4 or more carbon atoms | Having an acidic group possessing a pKa of less than 6 bonded through alkylene group having 4 or more carbon atoms |
| B | Having an acidic group possessing a pKa of less than 6 bonded through | Alkyl or aralkyl group (having no acidic group of a pKa of less than 6) |

TABLE 1-continued

| Combination | $R_{24}$ | $R_{25}$ |
|---|---|---|
| C | alkylene group having 4 or more carbon atoms | Having an acidic group possessing a pKa of less than 6 bonded through alkylene group having 3 or less carbon atoms |
| D | | Having an acidic group possessing a pKa of less than 6 bonded through alkylene group having 4 or more carbon atoms |

$L_2$ represents a conjugated methine group, and it is constituted of a conjugated methine chain having an odd number of carbon atom(s). It is preferably a monomethine group having 1 carbon atom.

In the general formula [III], each of $R_{31}$ and $R_{32}$ represents a hydrogen atom or an alkyl group, and these two substituents may bond to each other and form a cyclopentane ring or a cyclohexane ring. Examples of $R_{31}$ and $R_{32}$ are as described with regard to $R_{11}$ and $R_{12}$ in the general formula [I].

$R_{33}$ represents an alkylene group having 1 to 3 carbon atoms. Above all, an alkylene group having 1 to 2 carbon atoms is particularly preferred. $Y_3$ represents an acidic group possessing a pKa of less than 6. Examples of the acidic group possessing a pKa of less than 6 are as described with regard to $X_1$ in the general formula [I].

$R_{34}$ represents an aliphatic hydrocarbon residue, an aromatic hydrocarbon residue or a heterocyclic ring residue. Examples of the aliphatic hydrocarbon residue, aromatic hydrocarbon residue and heterocyclic ring residue are as described with regard to $R_{24}$ in the general formula [II].

Each of $R_{35}$ and $R_{36}$ represents an alkyl group or an aralkyl group. Examples of the alkyl group and aralkyl group are as described with regard to $R_{25}$ in the general formula [II].

At least one of $R_{34}$, $R_{35}$ and $R_{36}$ has an acidic group possessing a pKa of less than 6 bonded through an alkylene group having 4 or more carbon atoms. Examples of the acidic group possessing a pKa of less than 6 bonded through an alkylene group having 4 or more carbon atoms include the above AC-41 to AC-60. The upper limit of the number of carbon atoms is preferably 22. Above all, an acidic group possessing a pKa of less than 6 that is bonded to an alkylene group having 4 or more but 14 or less carbon atoms having a linear structure is particularly preferred. Examples of the acidic group possessing a pKa of less than 6 are similar to that described with regard to $X_1$ in the general formula [I]. Table 2 shows arrangement of acidic groups in the dye of the general formula [III]. In Table 2, it is preferred to select either A, B or C.

TABLE 2

| Combination | $R_{34}$ | $R_{35}$ | $R_{36}$ |
|---|---|---|---|
| A | Having no acidic group possessing a pKa of less than 6 bonded through alkylene group having 4 or more carbon atoms | Having acidic group possessing a pKa of less than 6 bonded through alkylene group having 4 or more carbon atoms | Having acidic group possessing a pKa of less than 6 bonded through alkylene group having 4 or more carbon atoms |
| B | Having acidic group possessing a pKa of less than 6 bonded through alkylene group having 4 or more carbon atoms | Having acidic group possessing a pKa of less than 6 bonded through alkylene group having 4 or more carbon atoms | Having no acidic group possessing a pKa of less than 6 bonded through alkylene group having 4 or more carbon atoms |
| C | | Having no acidic group bonded through alkylene group possessing a pKa of less than 6 having 4 or more carbon atoms | Having acidic group possessing a pKa of less than 6 bonded through alkylene group having 4 or more carbon atoms |
| D | Having acidic group possessing a pKa of less than 6 bonded through alkylene group having 4 or more carbon atoms | Having acidic group possessing a pKa of less than 6 bonded through alkylene group having 4 or more carbon atoms | Having acidic group possessing a pKa of less than 6 bonded through alkylene group having 4 or more carbon atoms |
| E | | Having acidic group bonded through alkylene group possessing a pKa of less than 6 having 4 or more carbon atoms | Having no acidic group possessing a pKa of less than 6 bonded through alkylene group having 4 or more carbon atoms |
| F | | Having no acidic group possessing a pKa of less than 6 bonded through alkylene group having 4 or more carbon atoms | Having acidic group possessing a pKa of less than 6 bonded through alkylene group having 4 or more carbon atoms |
| G | | Having no acidic group possessing a pKa of less than 6 bonded through alkylene group having 4 or more carbon atoms | Having no acidic group possessing a pKa of less than 6 bonded through alkylene group having 4 or more carbon atoms |

$L_3$ represents a conjugated methine group, and it is constituted of a conjugated methine chain having an odd number of carbon atom(s). It is preferably a monomethine group having 1 carbon atom.

In the general formula [IV], each of $R_{41}$ and $R_{42}$ represents a hydrogen atom or an alkyl group, and these two substituents may bond to each other and form a cyclopentane ring or a cyclohexane ring. Examples of $R_{41}$ and $R_{42}$ are as described with regard to $R_{11}$ and $R_{12}$ in the general formula [I].

$Ar_4$ represents a divalent aromatic hydrocarbon residue or a divalent heterocyclic ring residue. Examples of $Ar_4$ are as described with regard to $Ar_1$ in the general formula [I].

$X_4$ represents a residue having an acidic group possessing a pKa of less than 6 bonded through an alkylene group having 4 or more carbon atoms. Examples of $X_4$ are as described with regard to $X_1$ in the general formula [I].

$L_4$ represents a divalent binding group, and specific examples thereof preferably include divalent conjugated hydrocarbon residues such as a vinylene group, etc., divalent aromatic hydrocarbon residues such as, a 1,4-phenylene group, a 4-substituted styryl group, etc., and divalent heterocyclic ring residues such as a 2,5-thienylene group, 2,2'-bithienylene group, etc. These may further have a substituent each, and p represents 0 or 1.

$Y_4$ represents an ammonium salt of carboxyl group or an alkali metal salt of carboxyl group.

The dye of the general formula [II] or [III] has geometric isomers due to the steric configuration of substituents on two carbon atoms of the conjugated double bonds bonding a heterocyclic five-membered ring containing a sulfur atom. In the general formula [II], there are two geometric isomers such as E configuration and Z configuration. In the general formula

[III], two sets of carbon atoms of the conjugated double bonds are present in the dye molecule, so that there are four geometric isomers such as (ZZ) configuration, (ZE) configuration, (EZ) configuration and (EE) configuration. Chemical structures of the geometric isomers are as shown below.

[CF11]

General formula [II]

E configuration  Z configuration

[CF12]

General formula [III]

(ZZ) configuration (ZE) configuration (EZ) configuration (EE) configuration

In any one of the general formulae [I], [II] and [III], further, there are geometric isomers depending upon differences in geometric structure of substituent in the conjugated methine group. When each of $L_1$, $L_2$ and $L_3$ is a monomethine group, there are two geometric isomers (E configuration, Z configuration) as shown below.

[CF13]

General formulae [I], [II] and [III]

E configuration  Z configuration

In the general formula [IV], there are geometric isomers depending upon a difference in geometric structure of substituent on a conjugated methine group. When p is 0, there are two geometric isomers (E configuration, Z configuration) as shown below.

[CF14]

General formula [IV]

E configuration

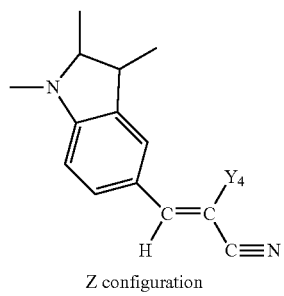

Z configuration

Further, when each of $L_1$, $L_2$ and $L_3$ in the general formulae [I], [II] and [III] is a trimethine group, and when p in the general formula [IV] is 1 and $L_4$ is a vinylene group, there are two geometric isomers (cis configuration, trans configuration) as shown below, depending upon a difference in geometric structure of conjugated double bonds thereof.

[CF15]

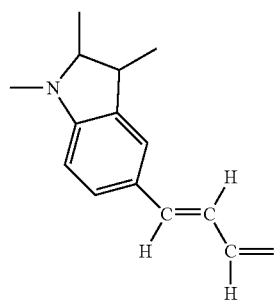

trans configuration cis configuration

When synthesized, normally, the dye of this invention is isolated as a mixture of these geometric isomers. In this invention, the dye may be any one of these geometric isomers and may be a mixture of these.

The compound of the general formula [I] in this invention specifically includes the following compounds, while it shall not be limited thereto.

[CF16]

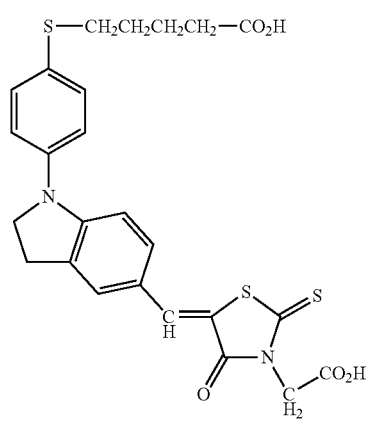

A-1

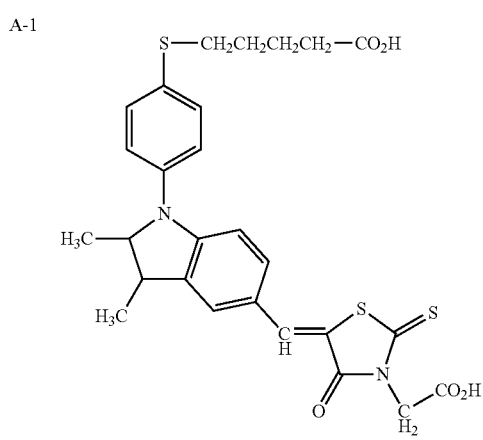

A-2

-continued
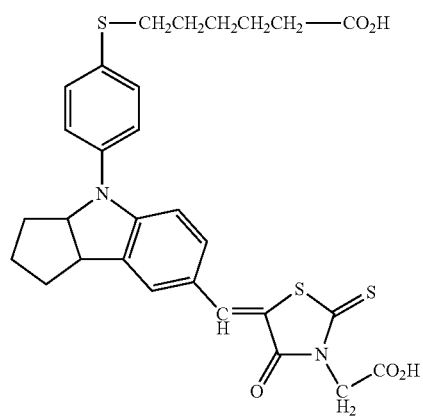
A-3
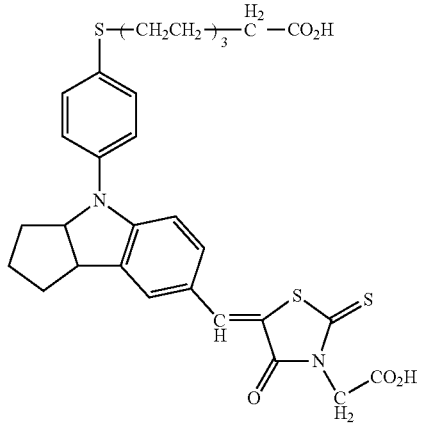
A-4
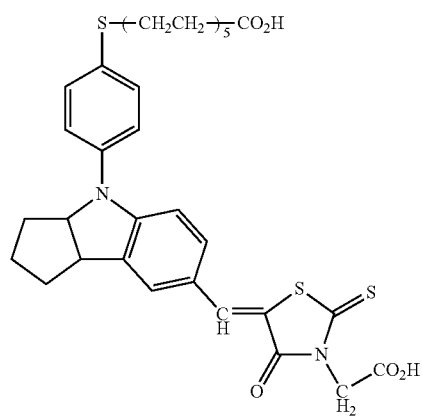
A-5
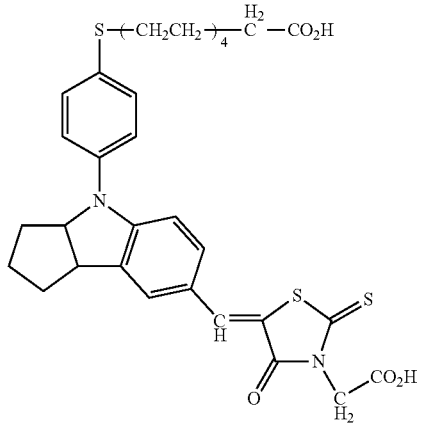
A-6
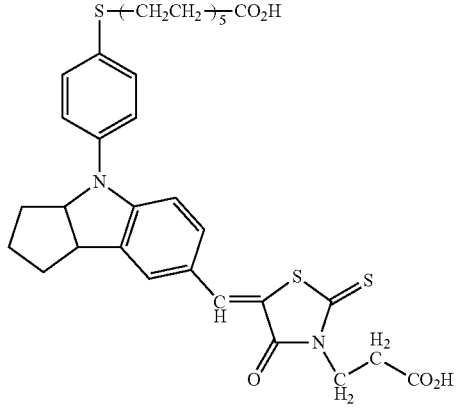
A-7
A-8
[CF18]
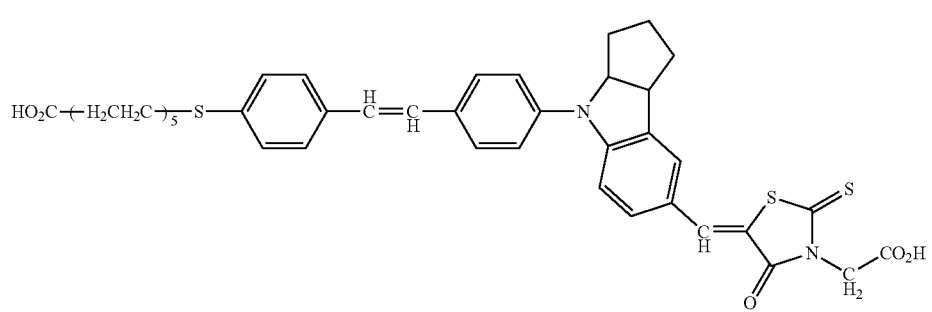
A-9

-continued
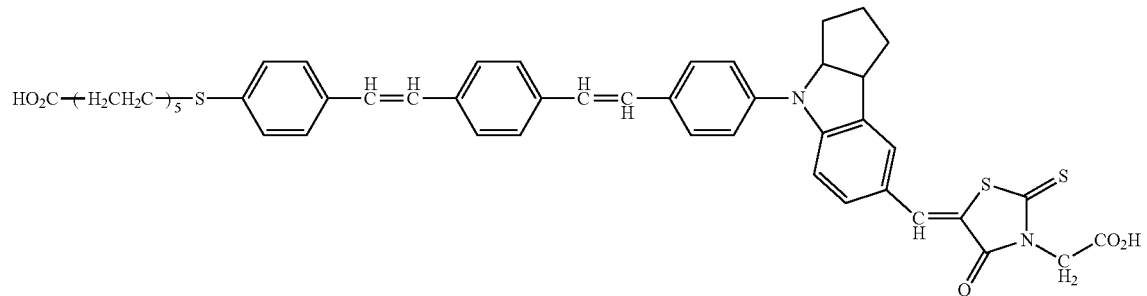
A-10
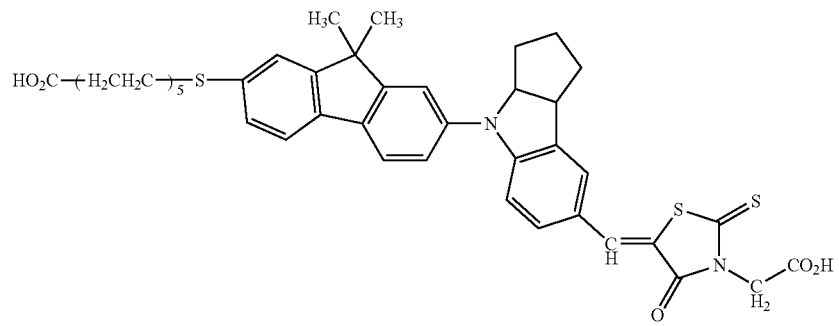
A-11
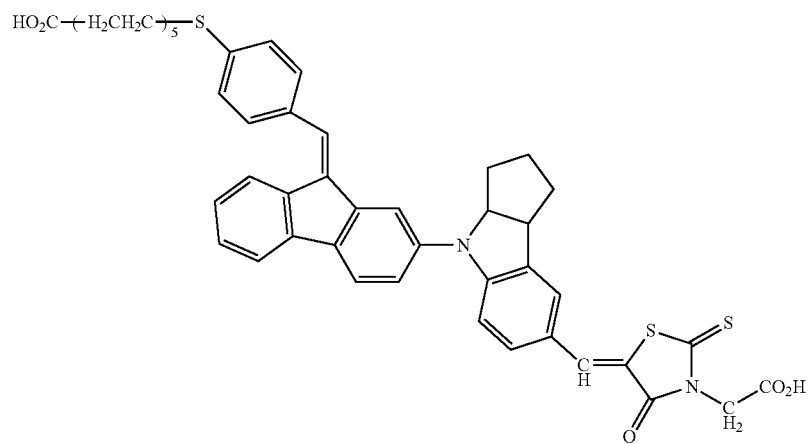
A-12
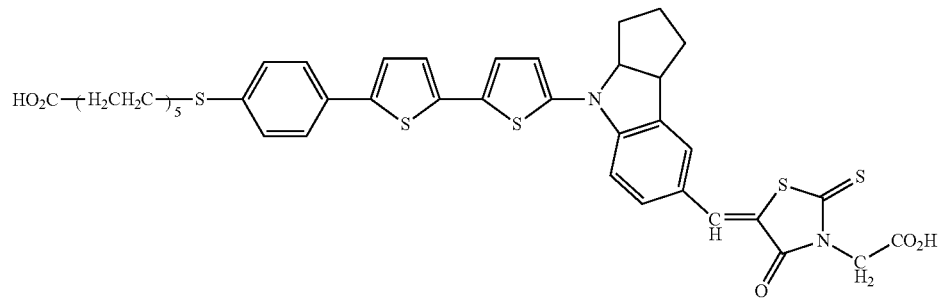
A-13

-continued
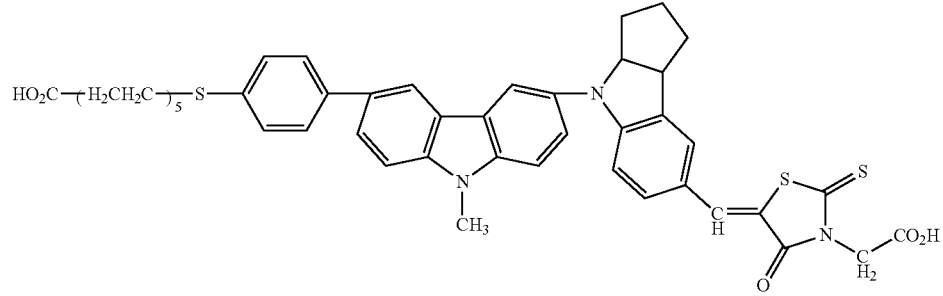
A-14
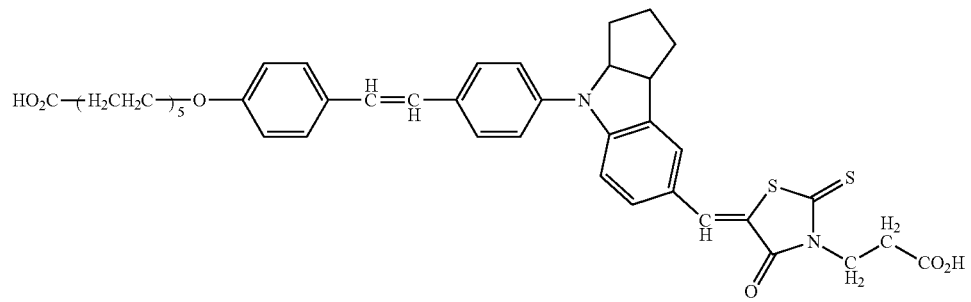
A-15
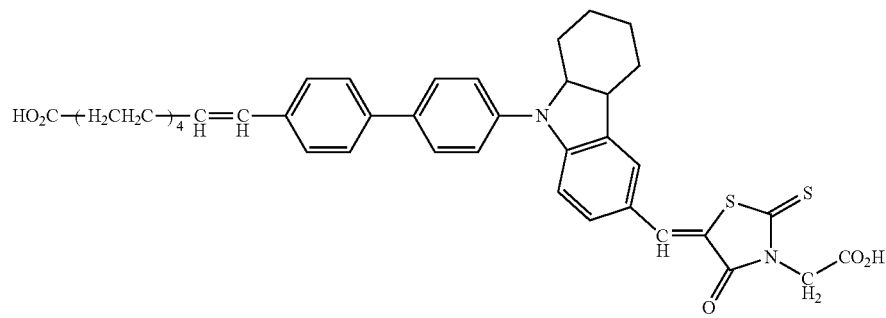
A-16
[CF20]
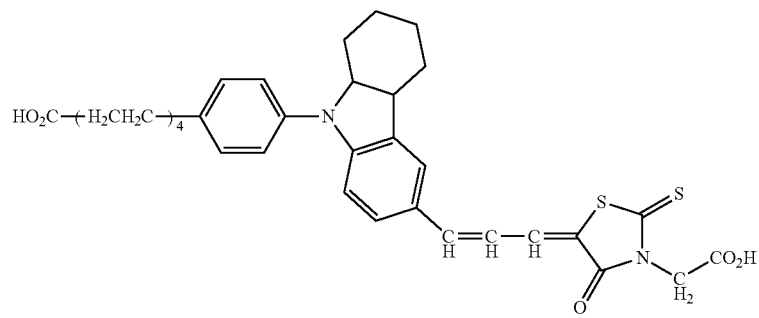
A-17
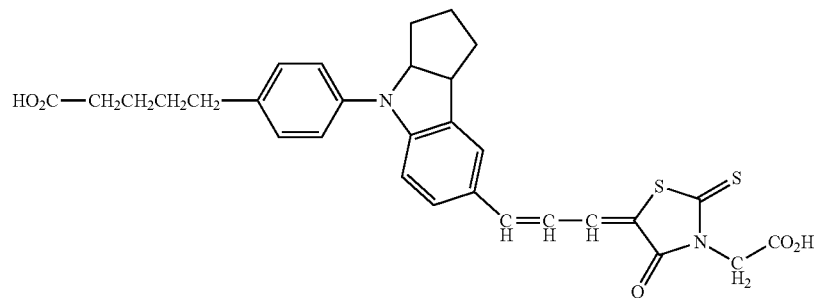
A-18

-continued
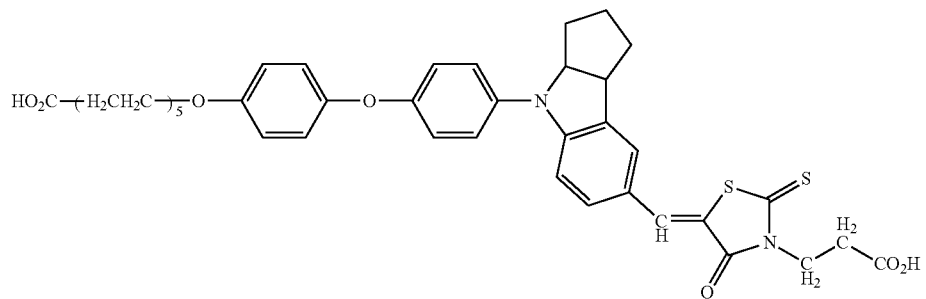
A-19
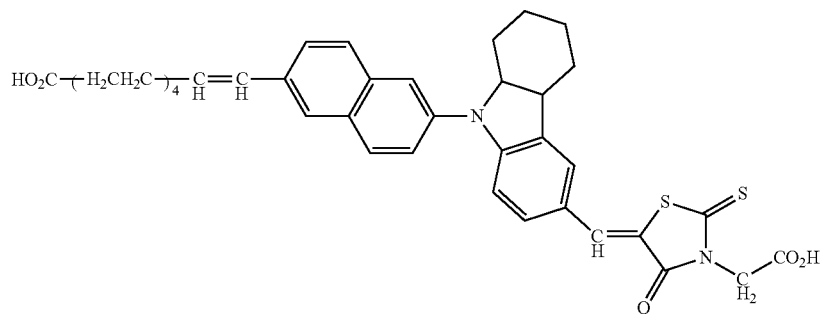
A-20
The compound of the general formula [II] in this invention specifically includes the following compounds, while it shall not be limited thereto.
[CF21]
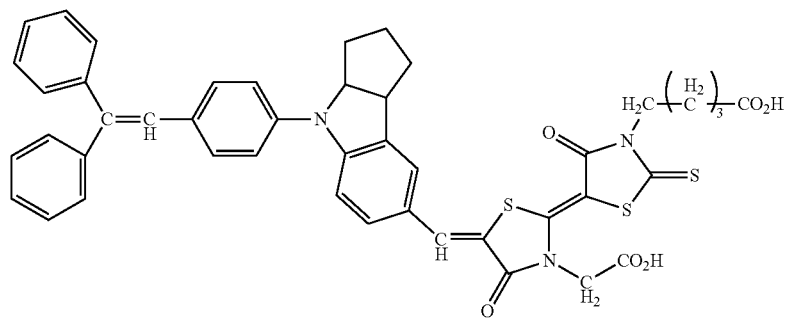
B-1
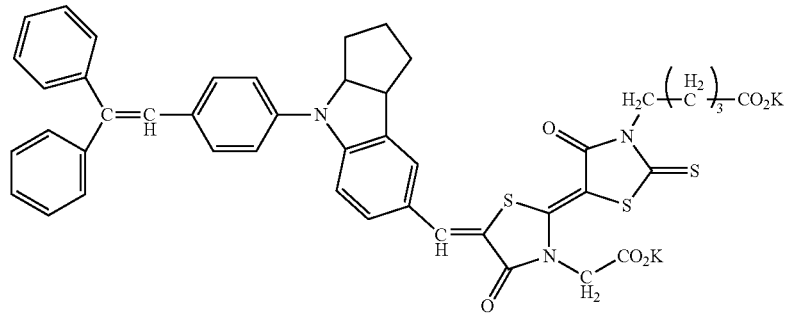
B-2

-continued
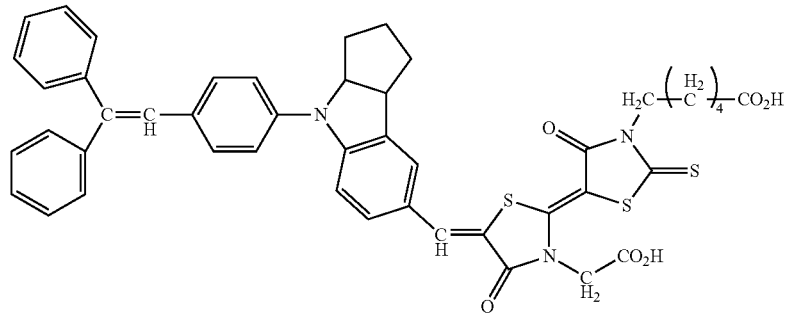
B-3
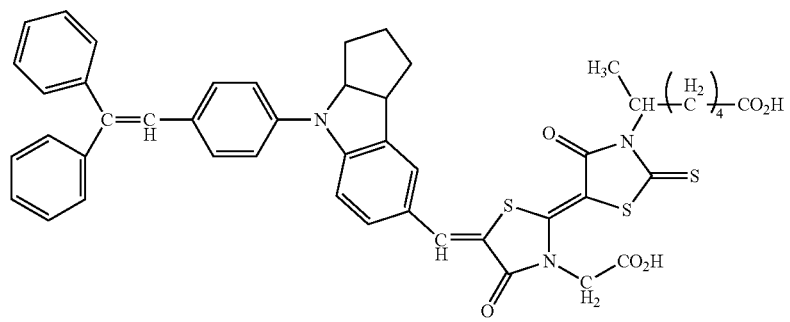
B-4
[CF22]
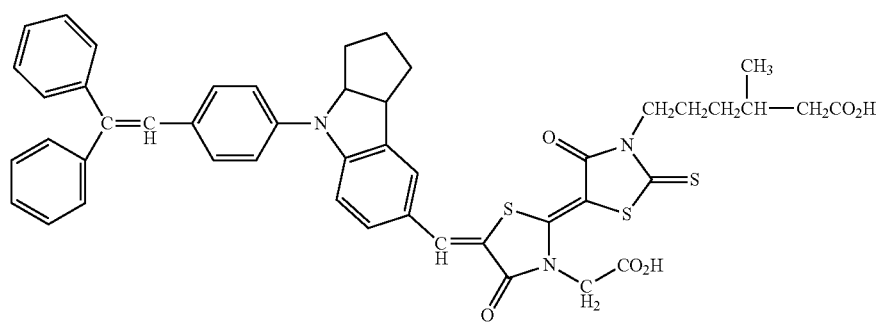
B-5
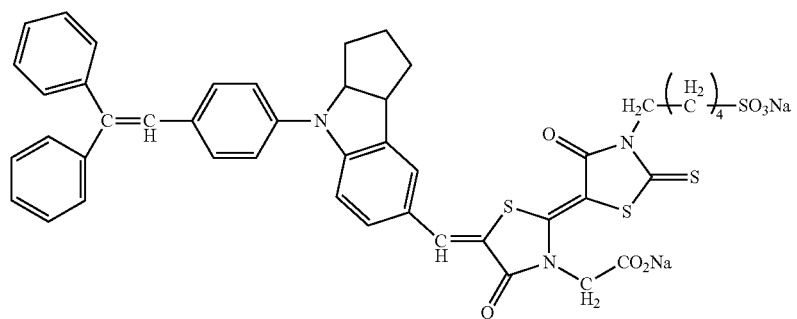
B-6

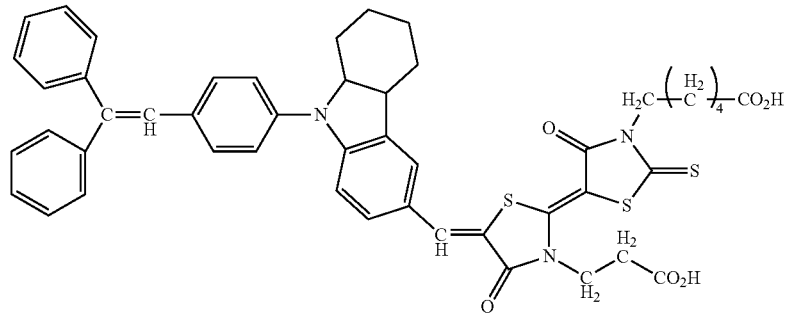
B-7
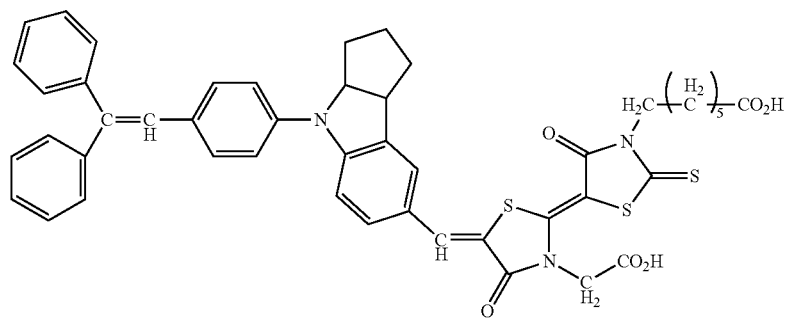
B-8
[CF23]
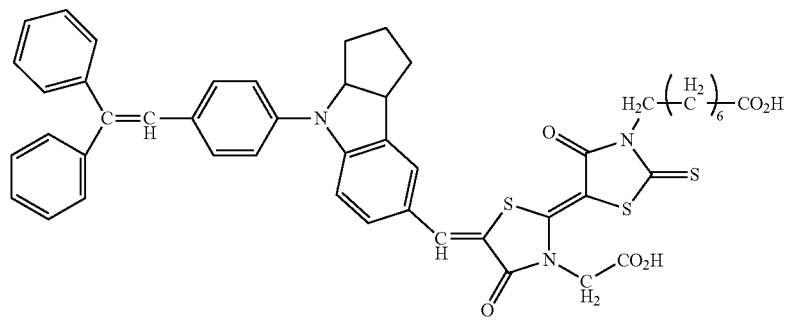
B-9
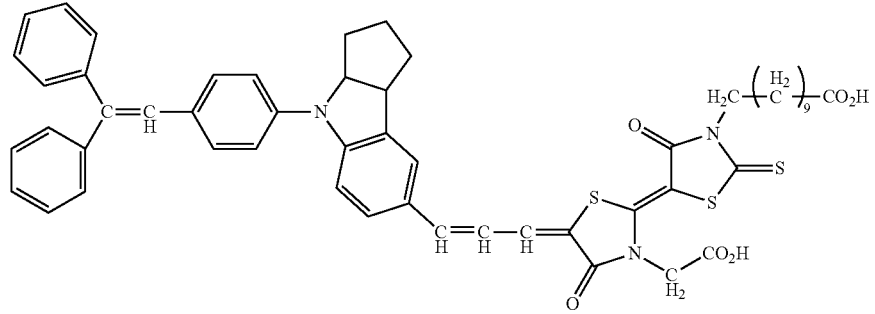
B-10

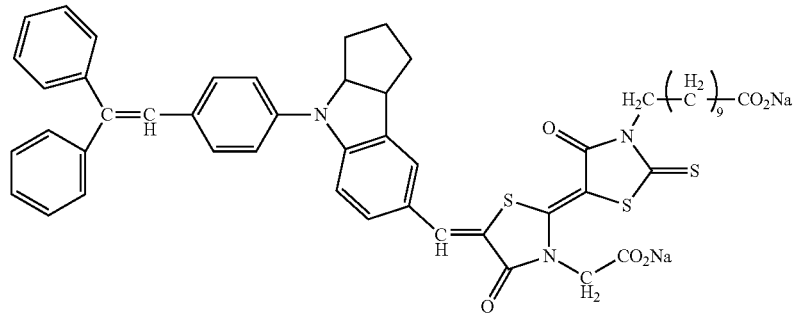
B-11
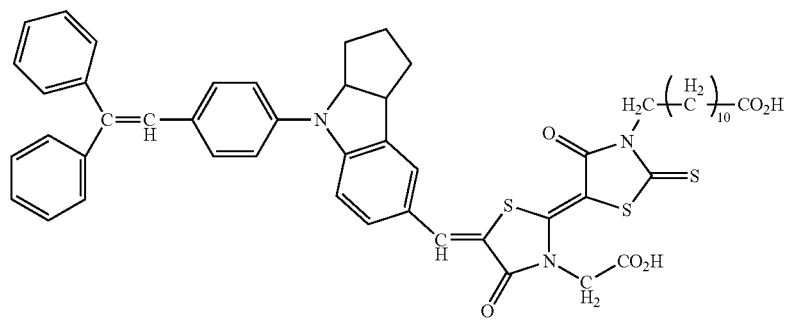
B-12
[CF24]
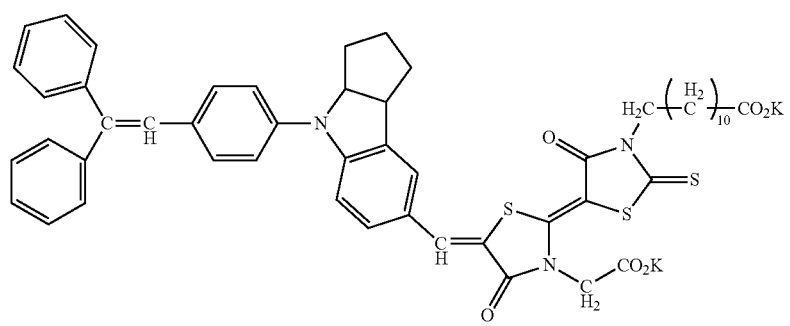
B-13
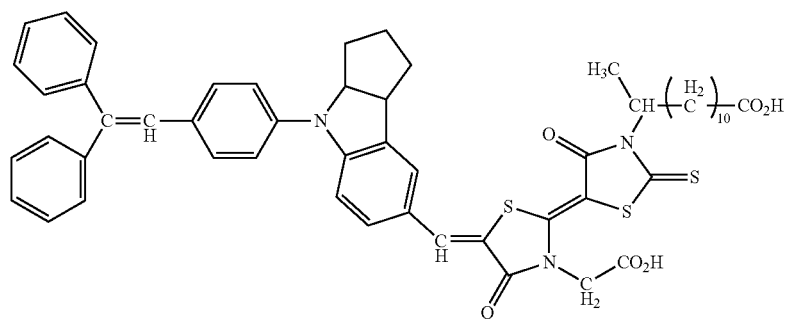
B-14

-continued
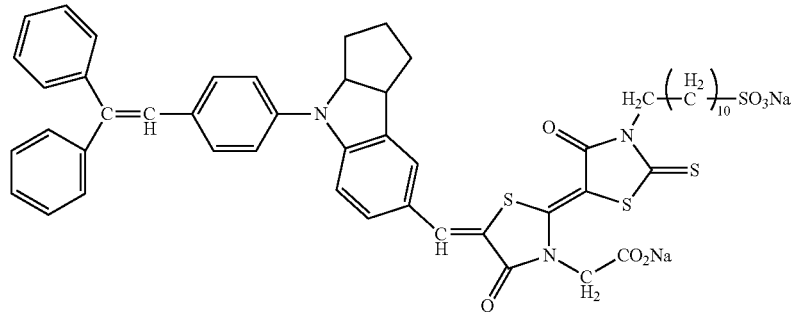
B-15
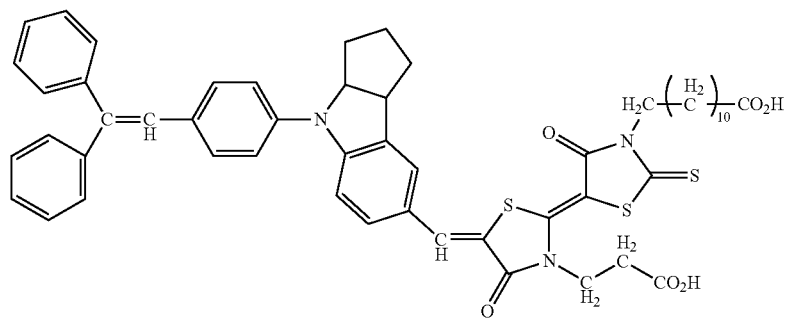
B-16
[CF25]
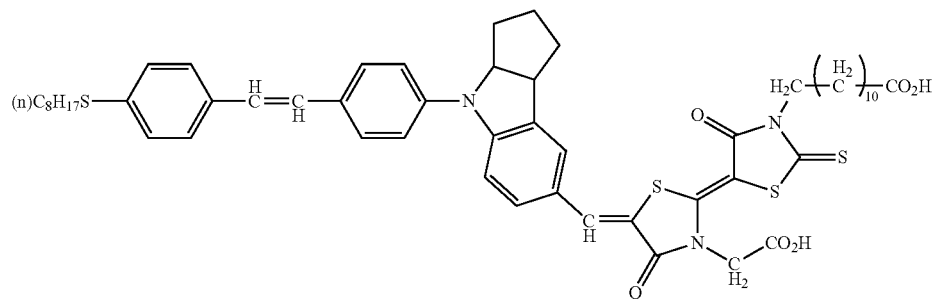
B-17
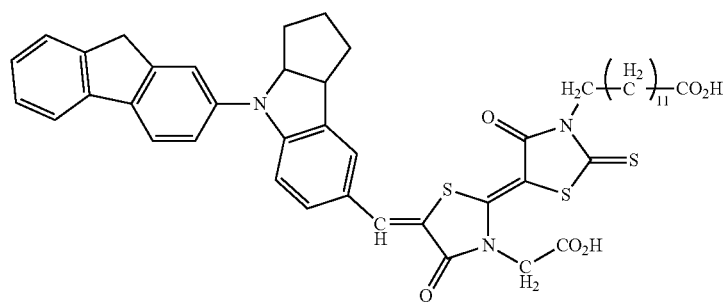
B-18

-continued
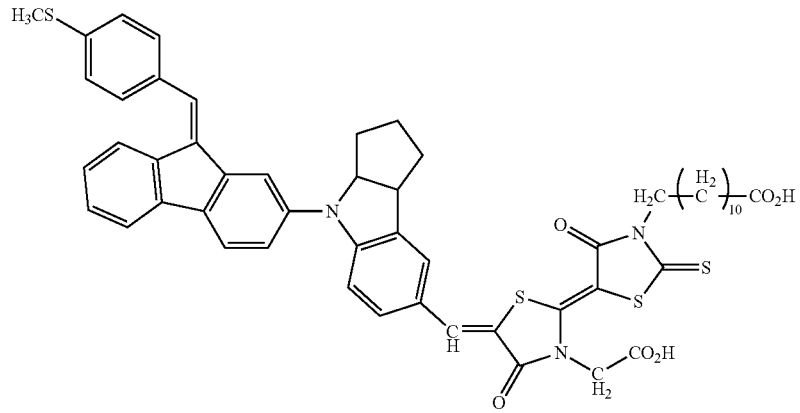
B-19
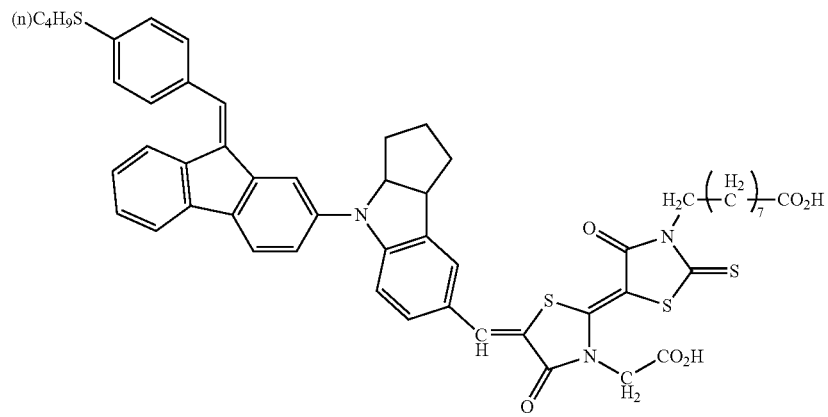
B-20
[CF26]
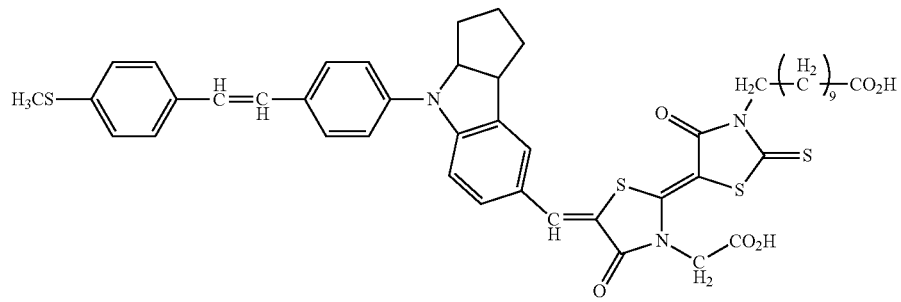
B-21
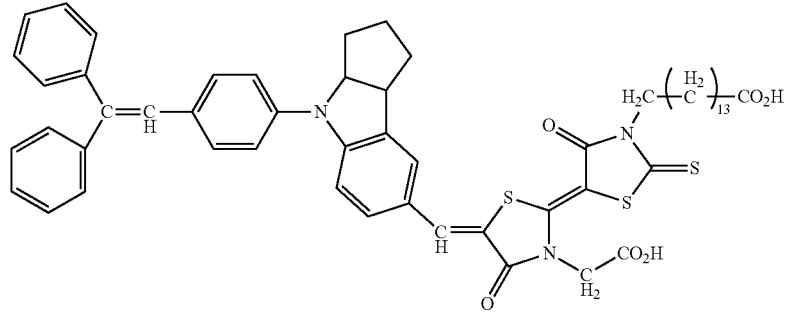
B-22

-continued
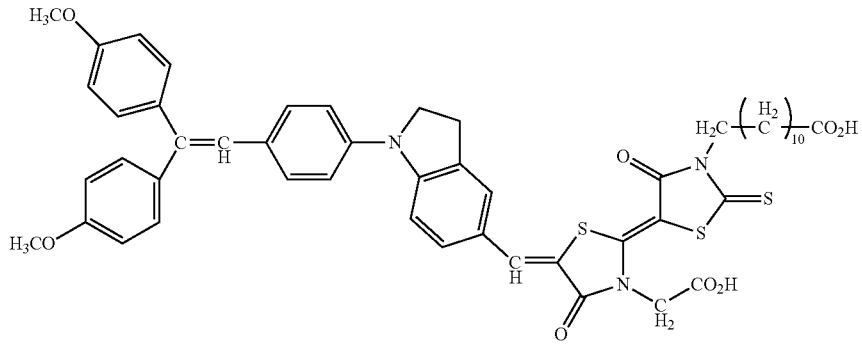
B-23
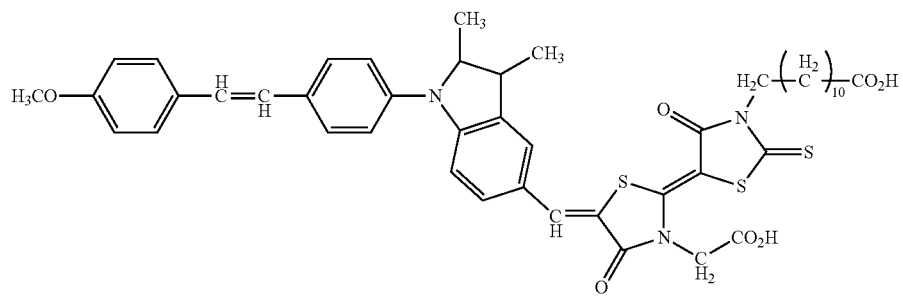
B-24
[CF27]
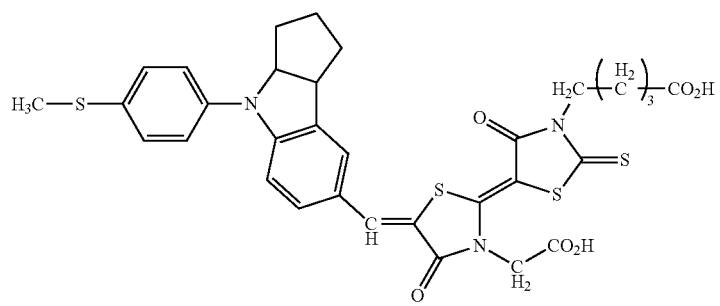
B-25
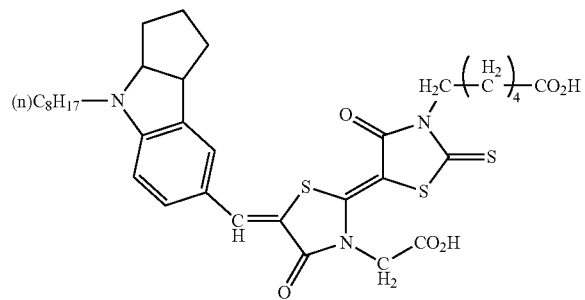
B-26
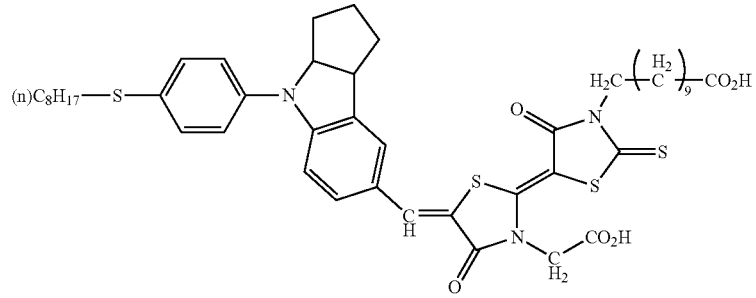
B-27

-continued
B-28
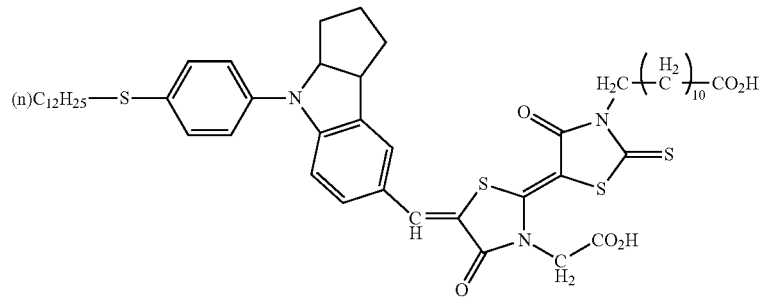
[CF28]
B-29
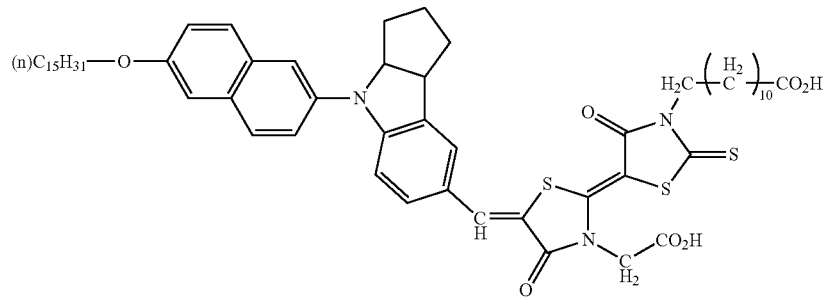
B-30
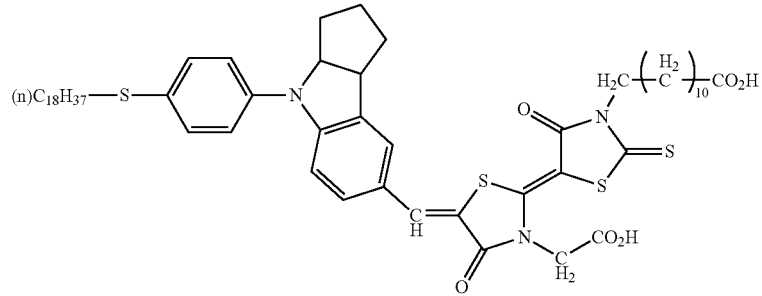
B-31
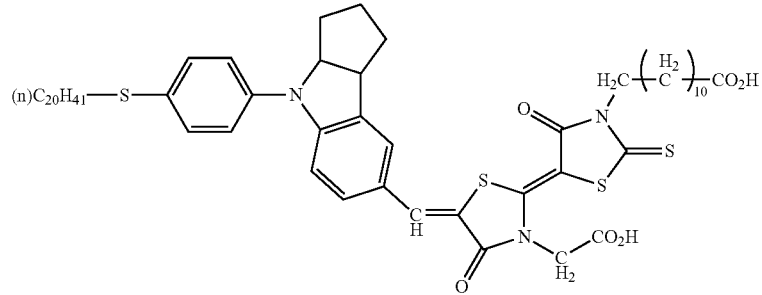
B-32
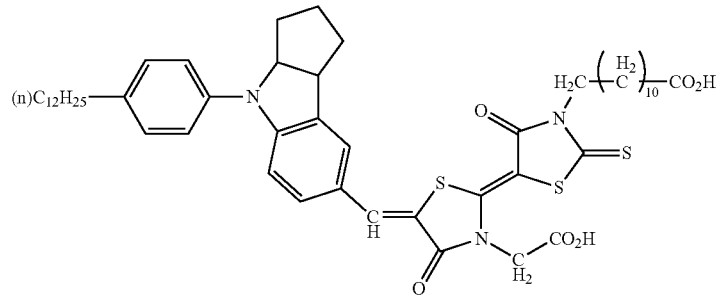

[CF29]
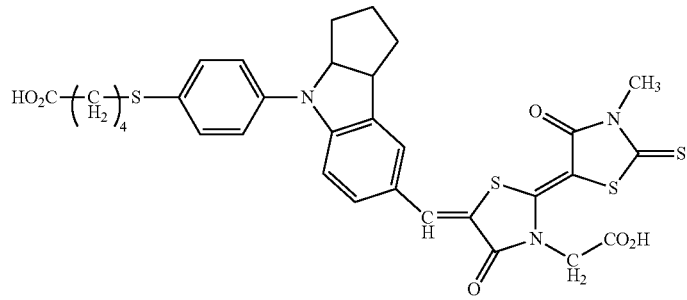
B-33
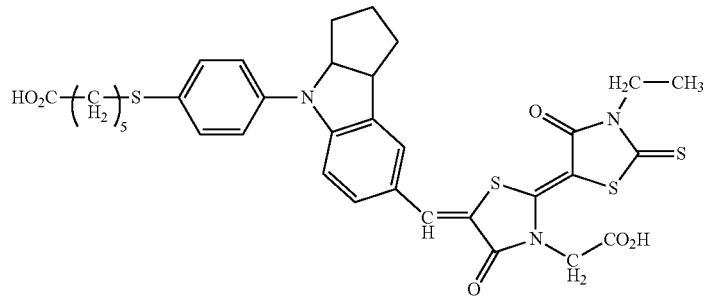
B-34
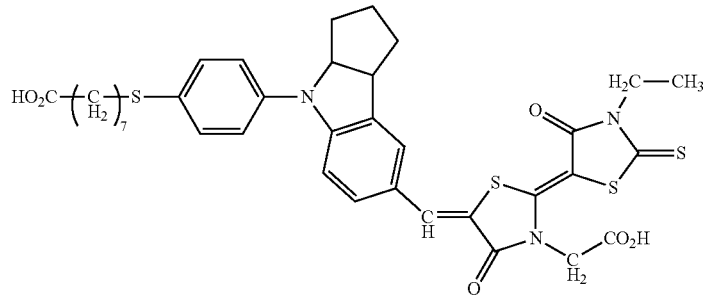
B-35
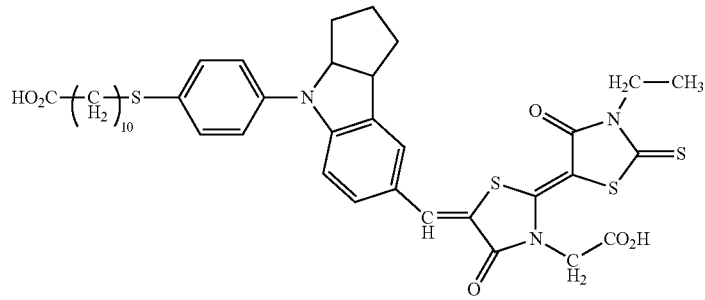
B-36
[CF30]
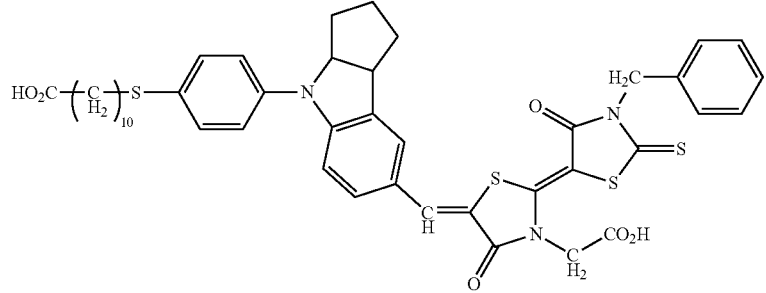
B-37

-continued
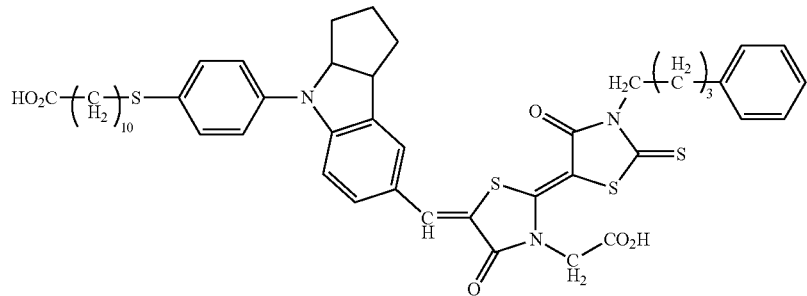
B-38
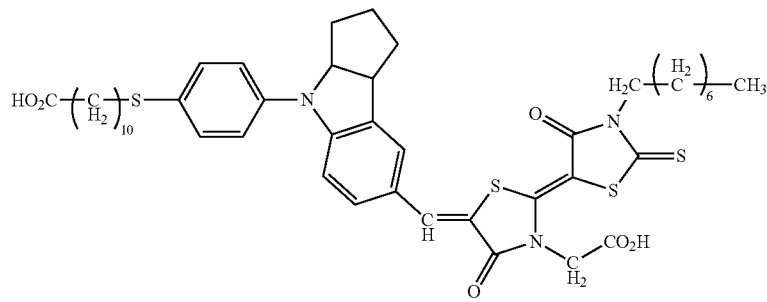
B-39
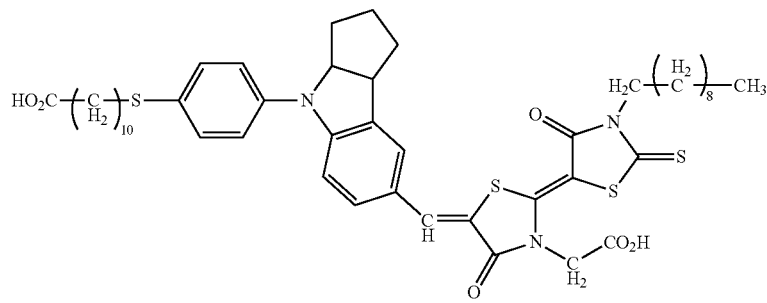
B-40
[CF31]
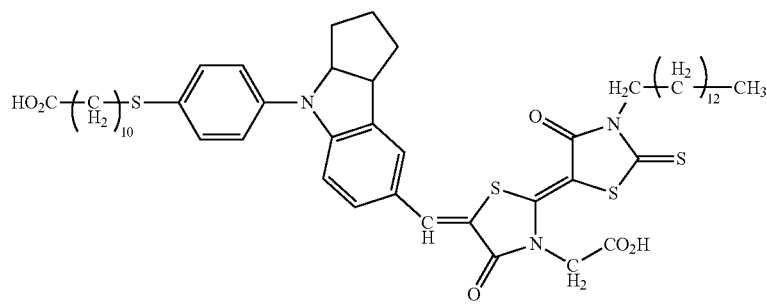
B-41
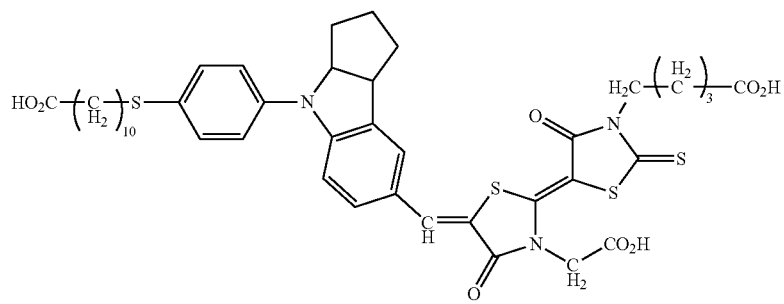
B-42

-continued
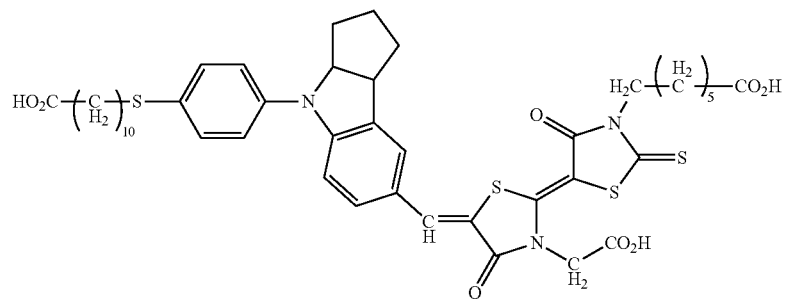
B-43
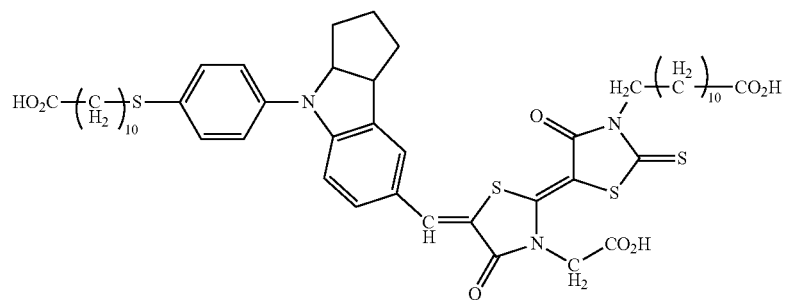
B-44
[CF32]
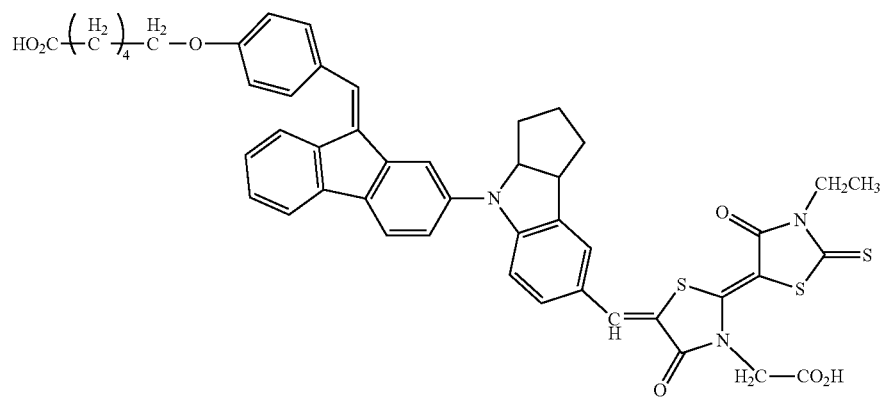
B-45
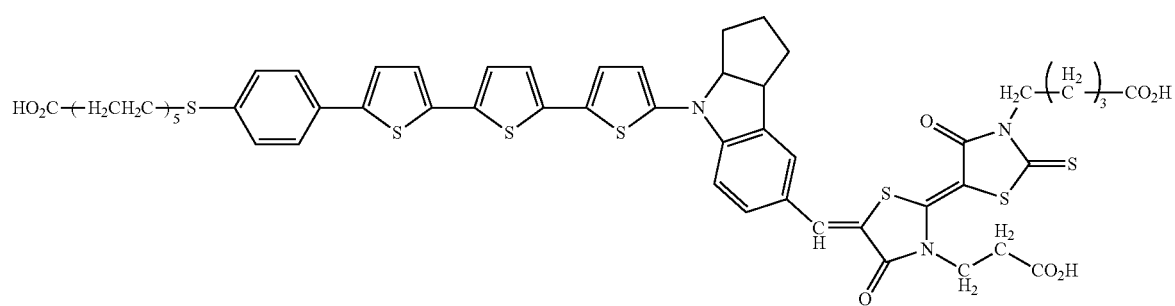
B-46

-continued
B-47
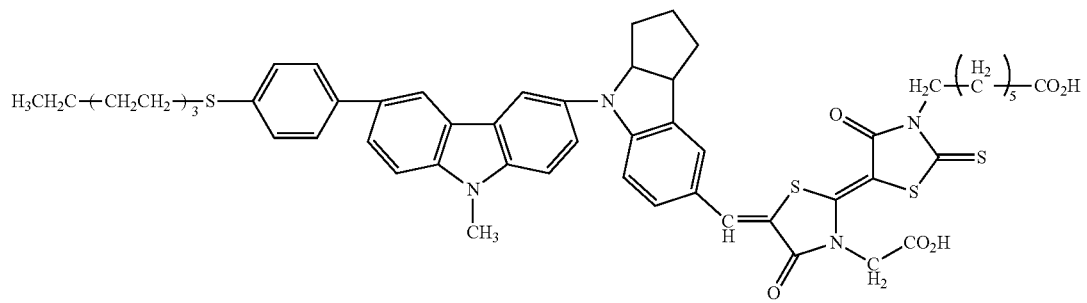
B-48
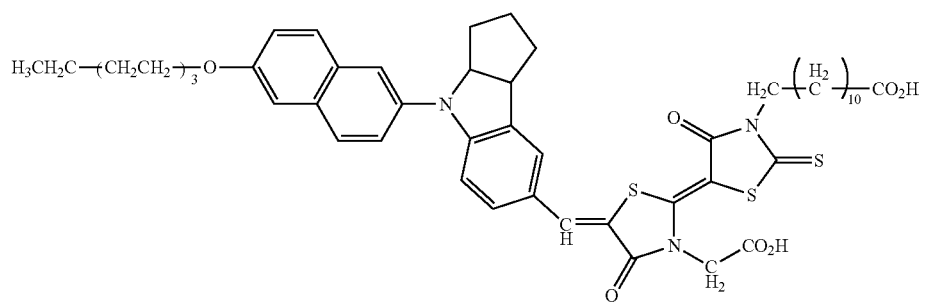
[CF33]
B-49
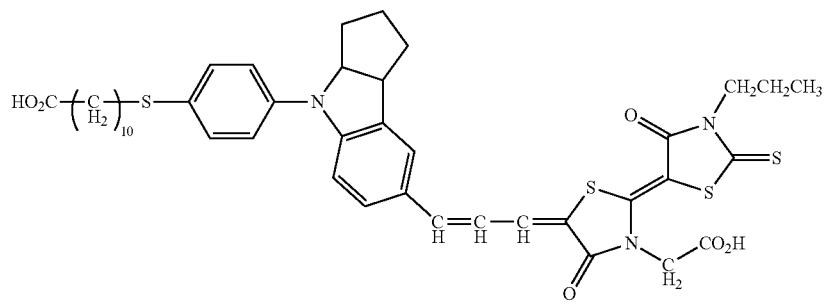
B-50
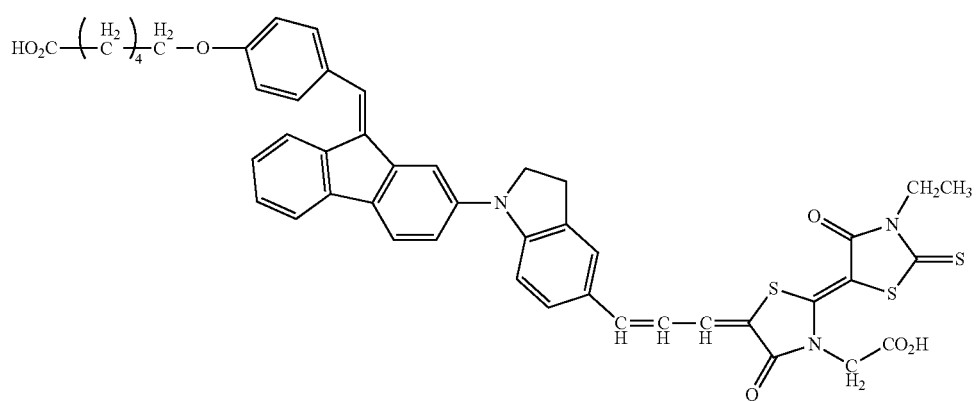
B-51
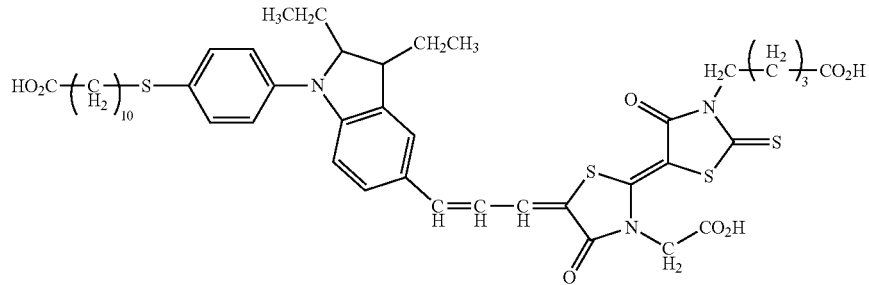

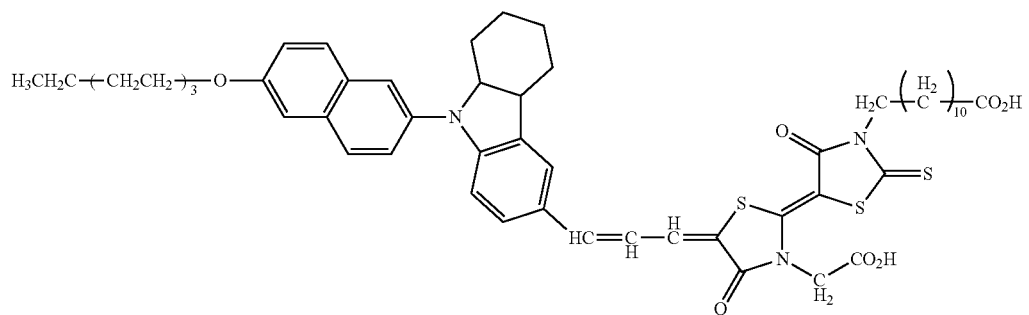
B-52
The compound of the general formula [III] in this invention specifically includes the following compounds, while it shall not be limited thereto.
[CF34]
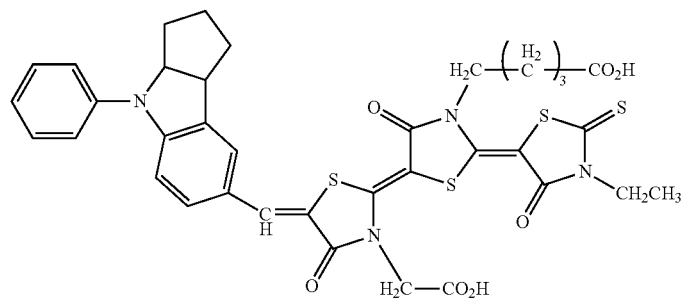
C-1
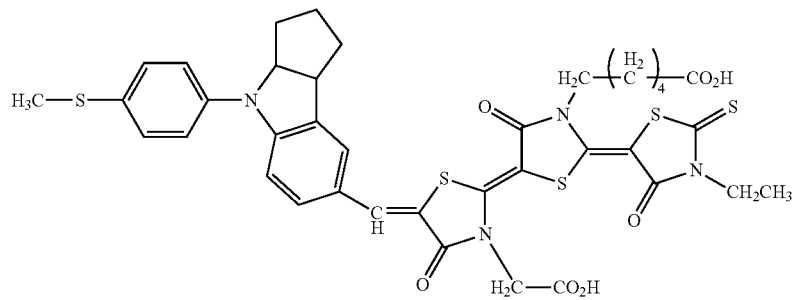
C-2
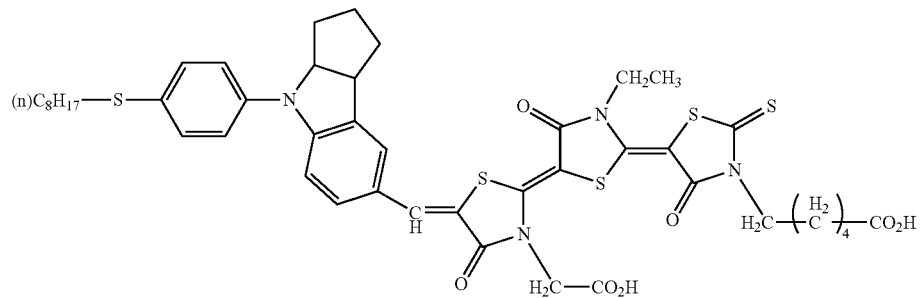
C-3

-continued
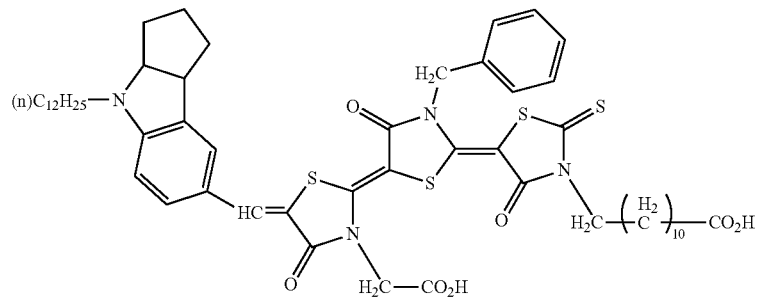
C-4
[CF35]
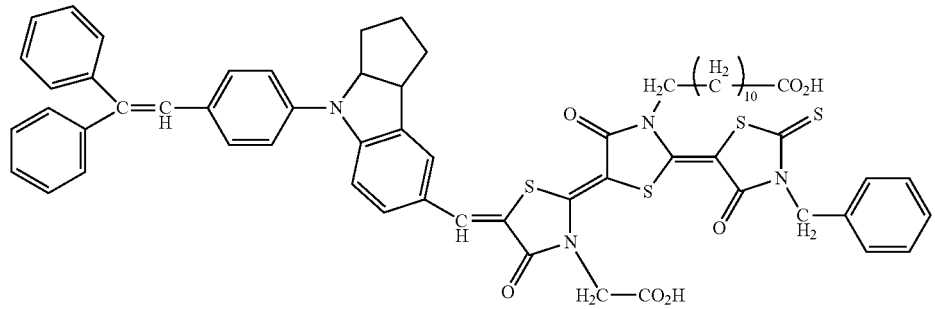
C-5
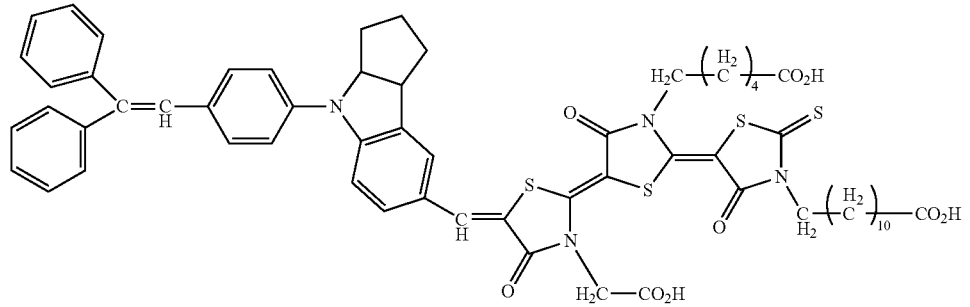
C-6
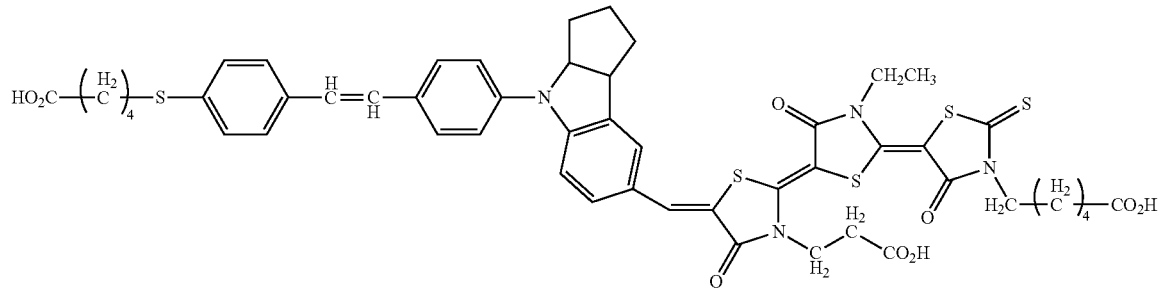
C-7
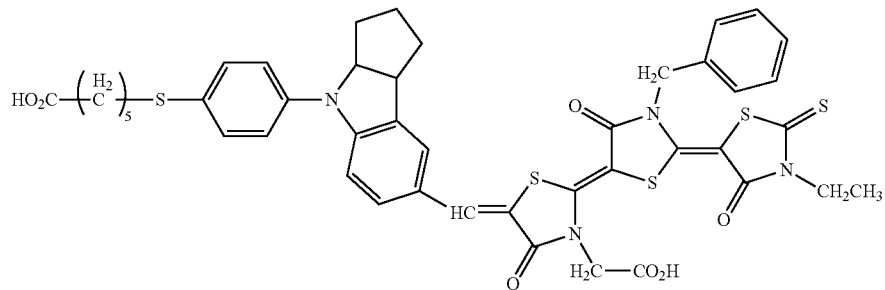
C-8

[CF36]
C-9
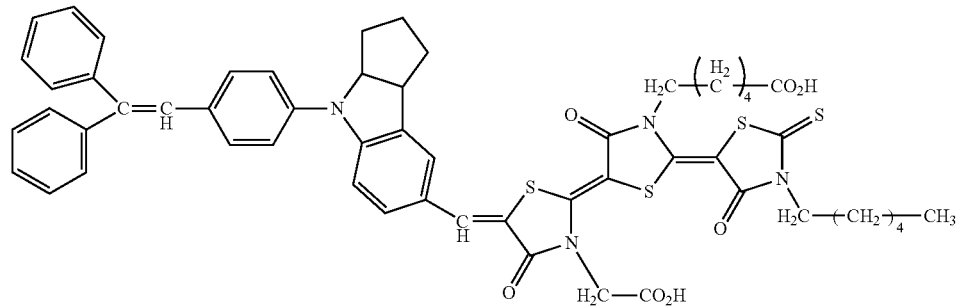
C-10
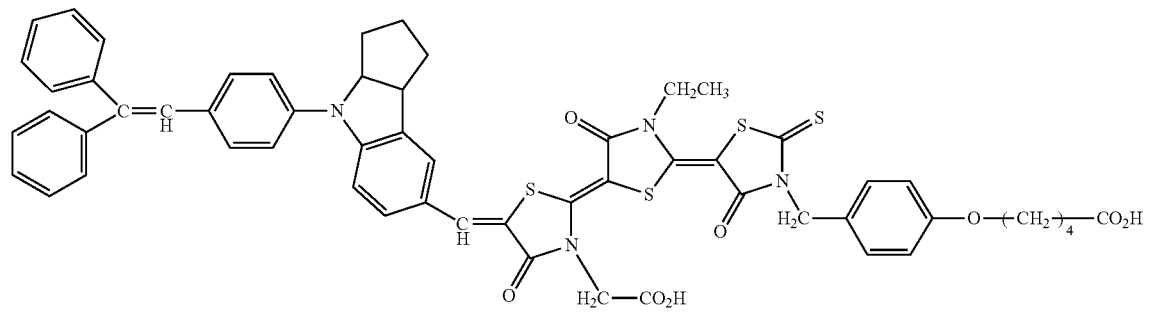
C-11
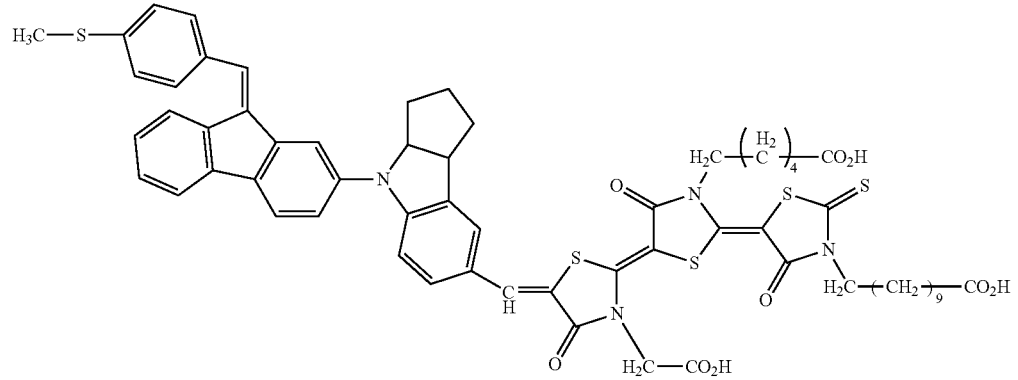
C-12
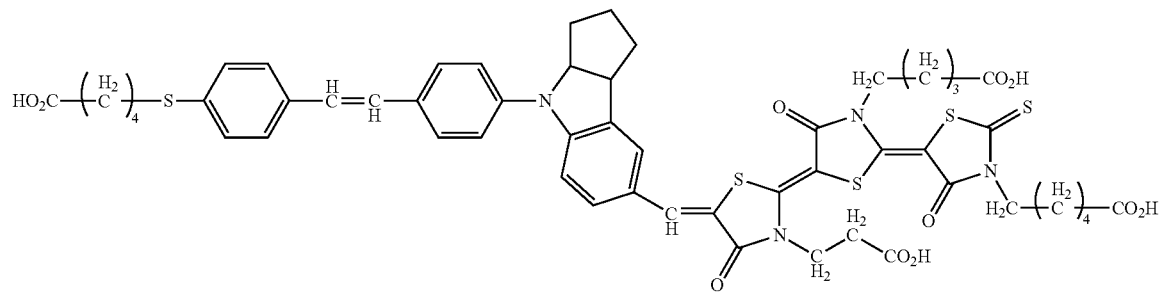

[CF37]
-continued
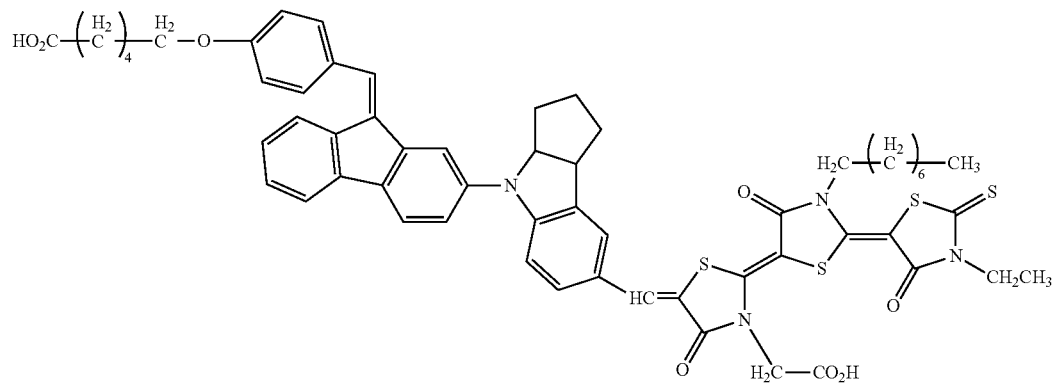
C-13
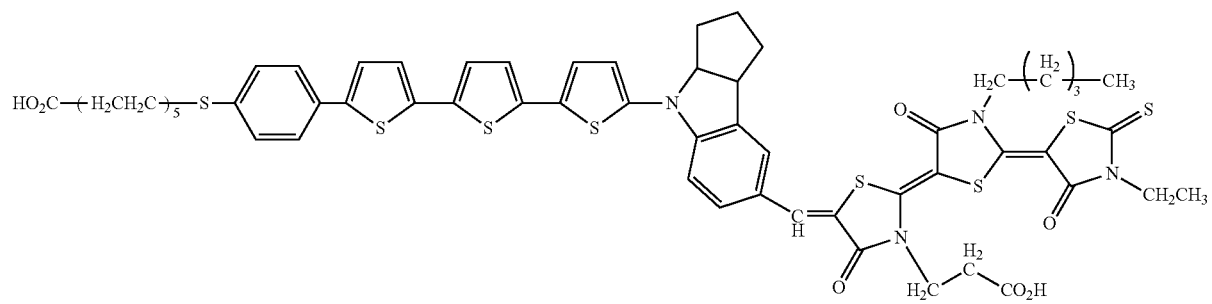
C-14
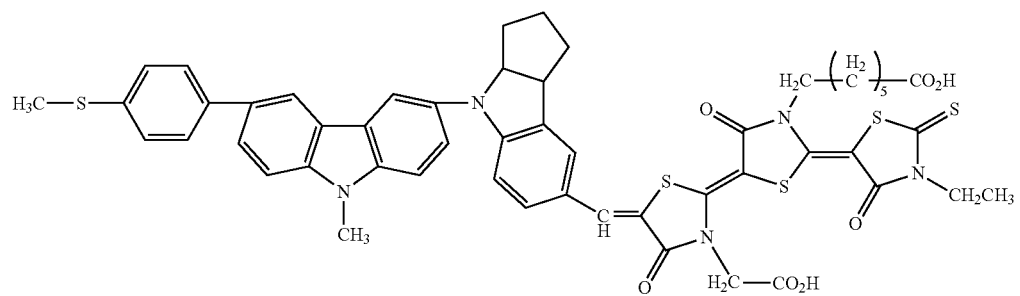
C-15
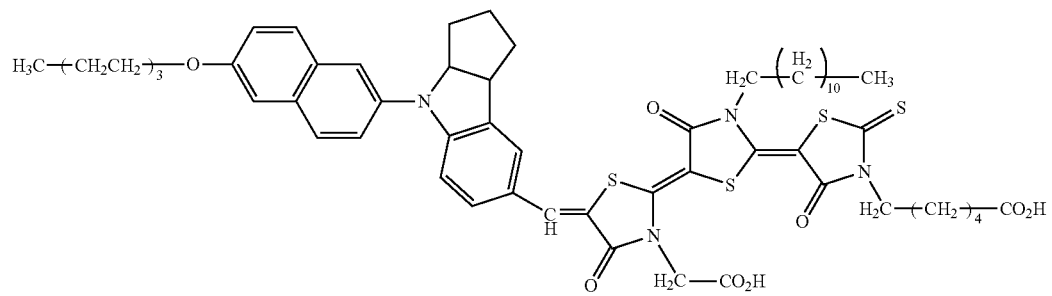
C-16

[CF38]
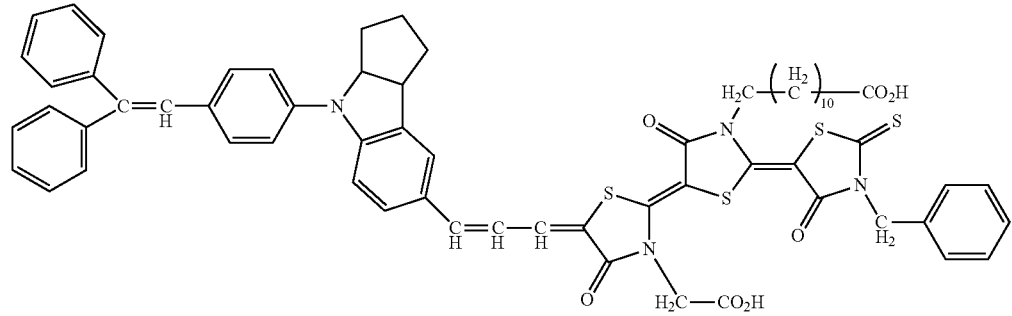
C-17
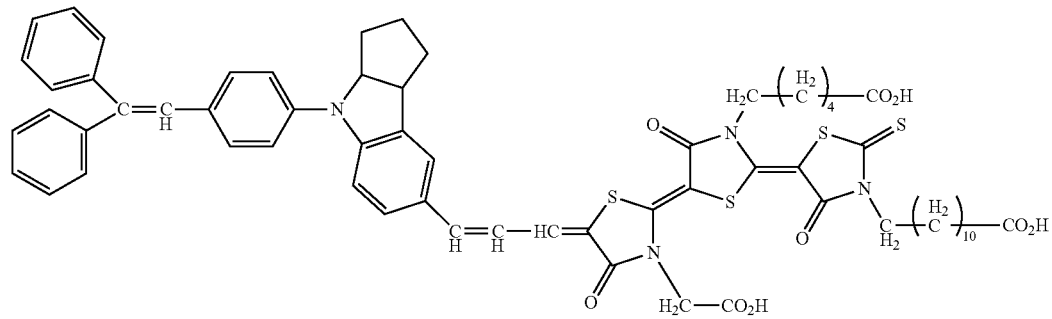
C-18
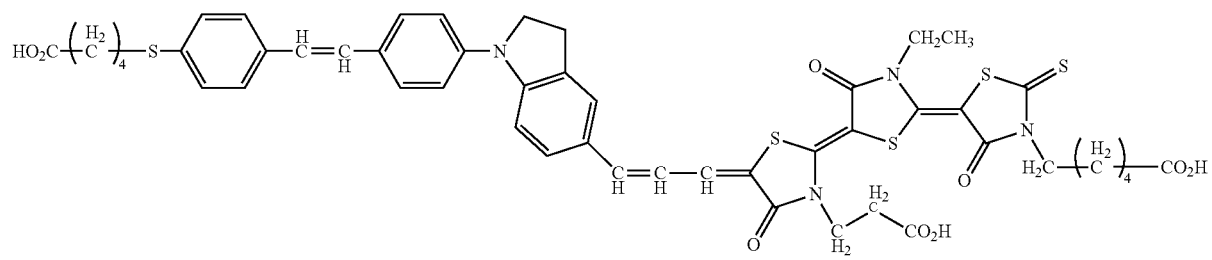
C-19
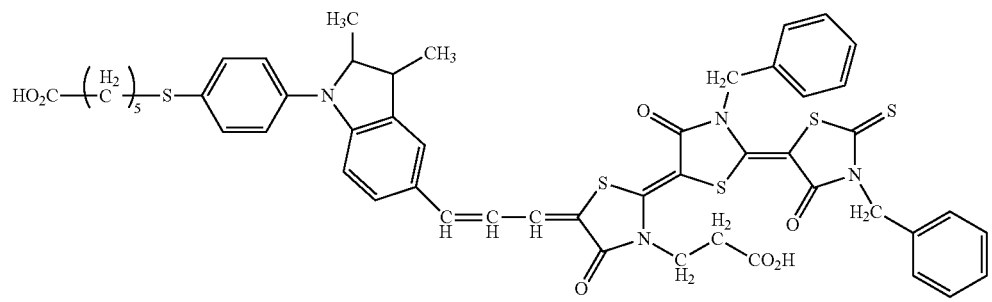
C-20
The compound of the general formula [IV] in this invention specifically includes the following compounds, while it shall not be limited thereto.

[CF39]
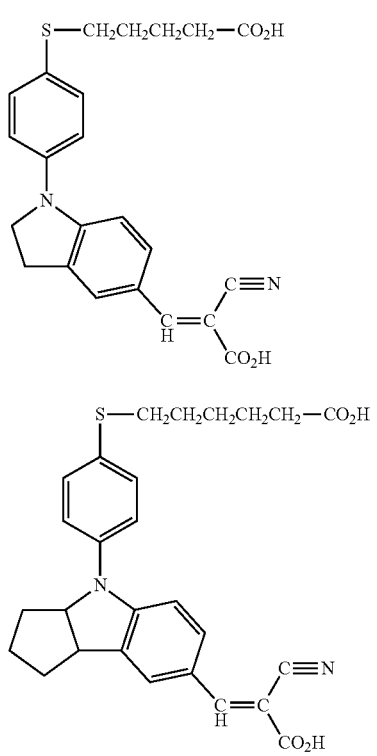
D-1
D-2
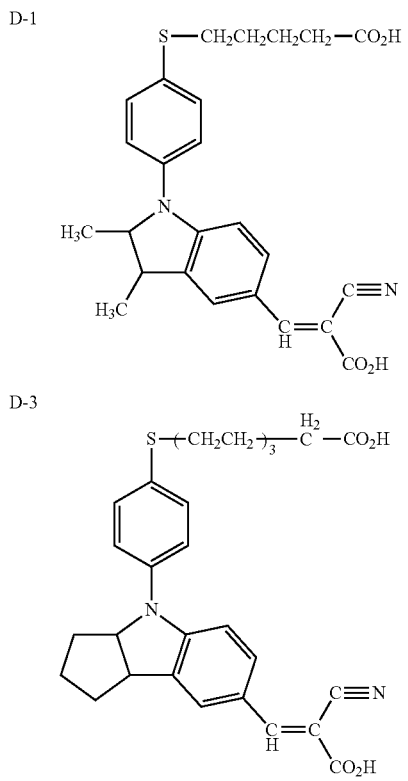
D-3
[CF40]
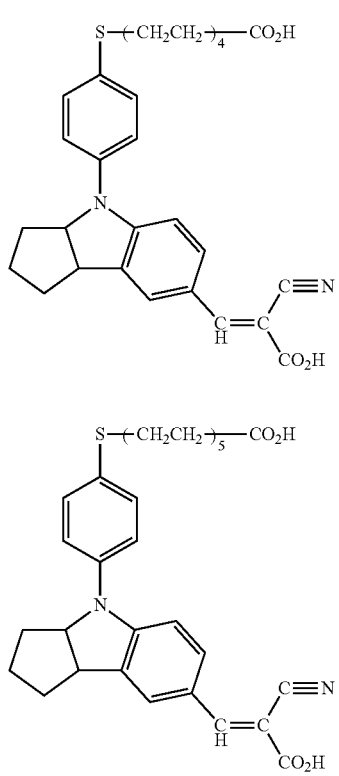
D-4
D-5
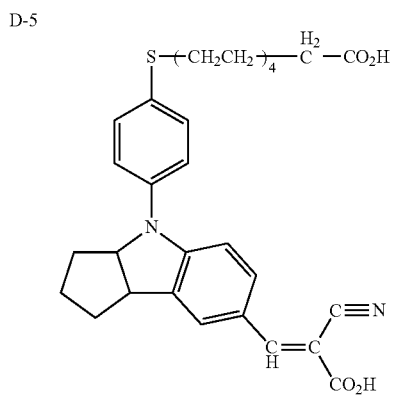
D-6
D-7
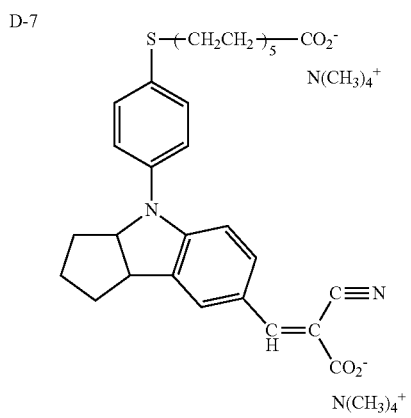
D-8

[CF41]
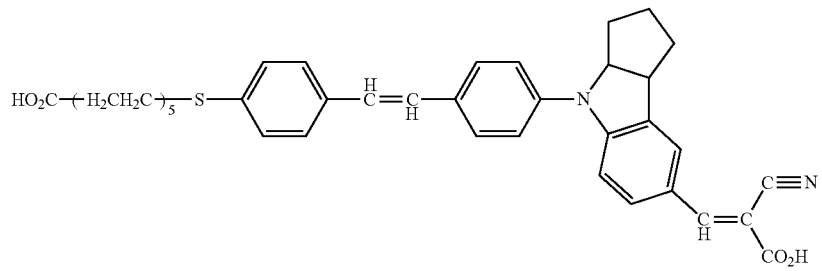
D-9
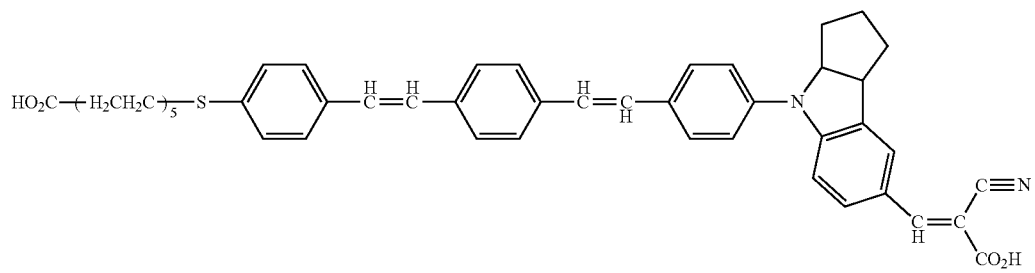
D-10
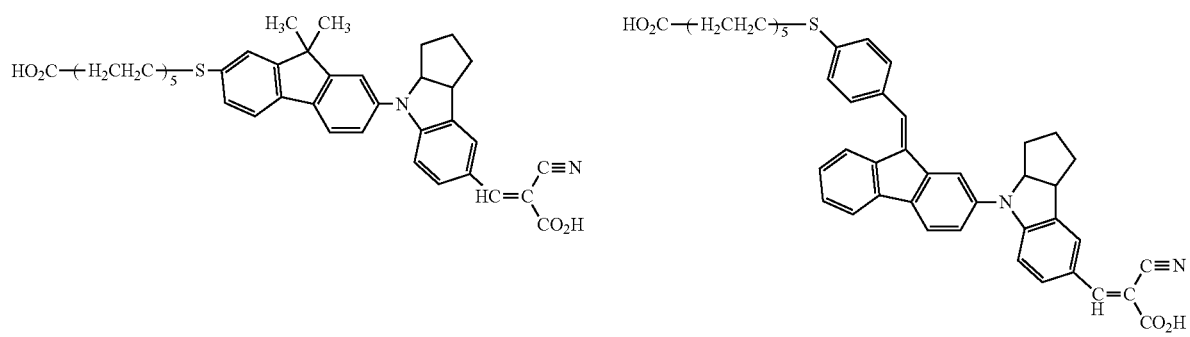
D-11 D-12
[CF42]
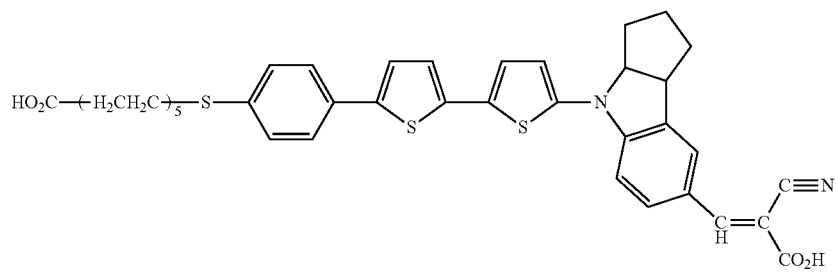
D-13
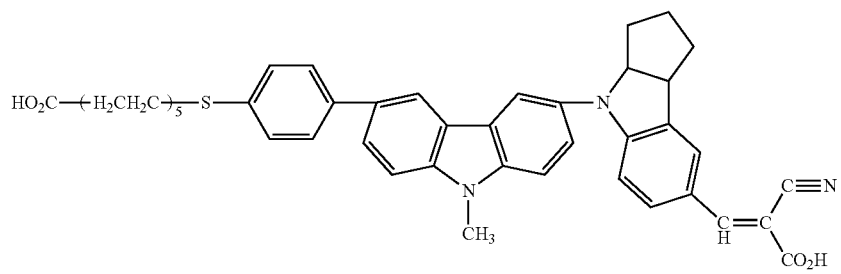
D-14

-continued
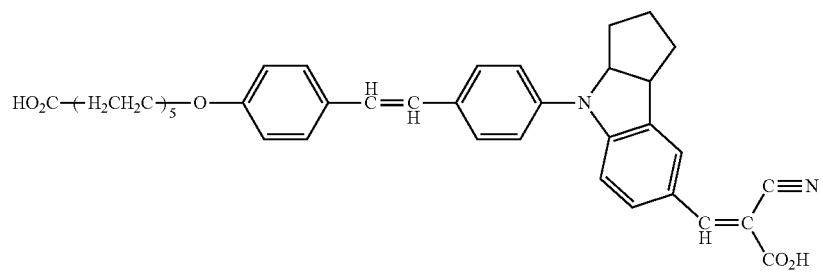
D-15
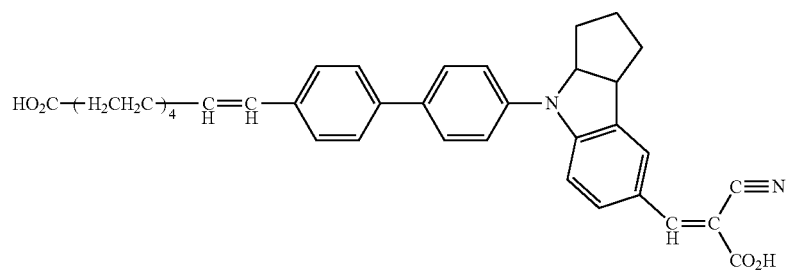
D-16
[CF43]
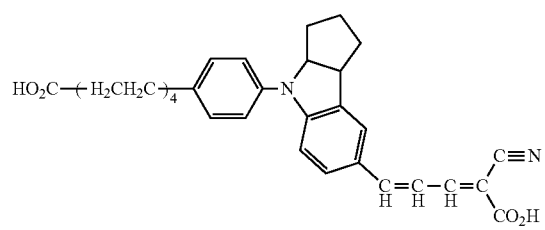
D-17
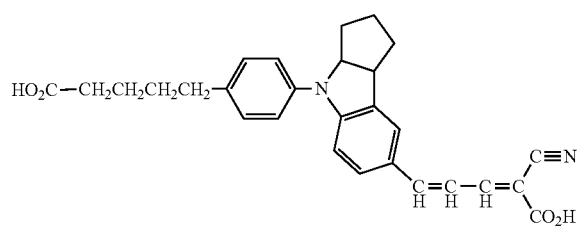
D-18
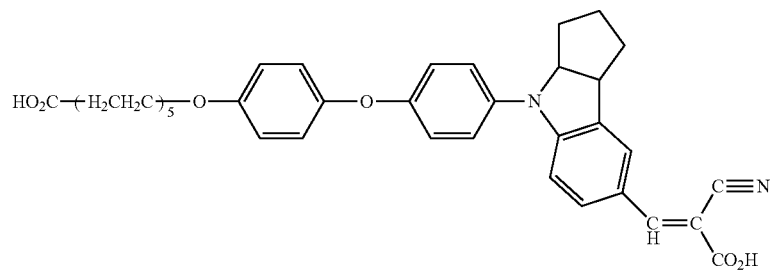
D-19
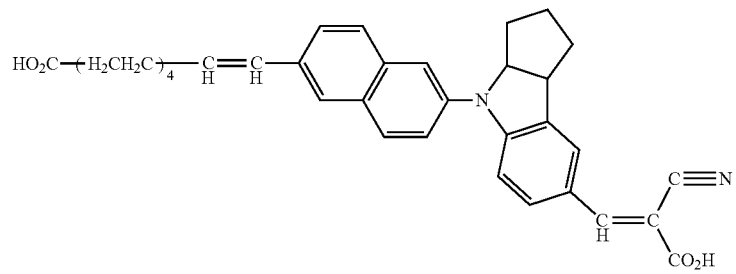
D-20

[CF44]

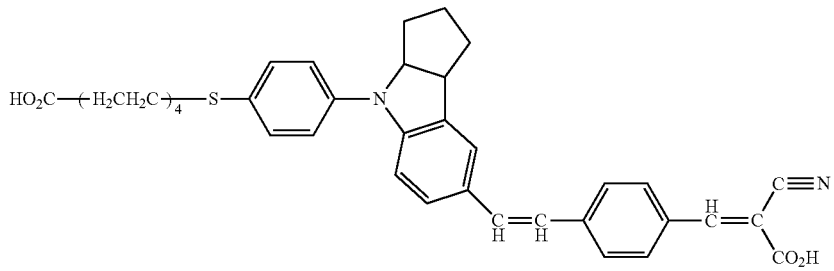

D-21

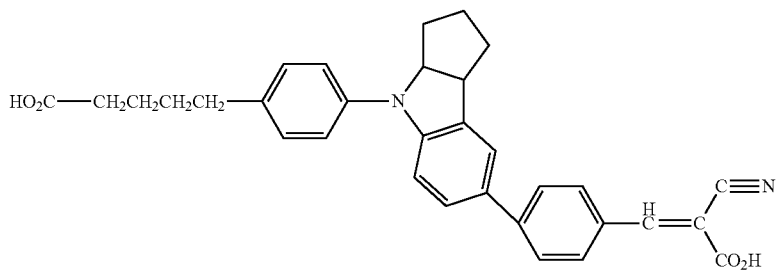

D-22

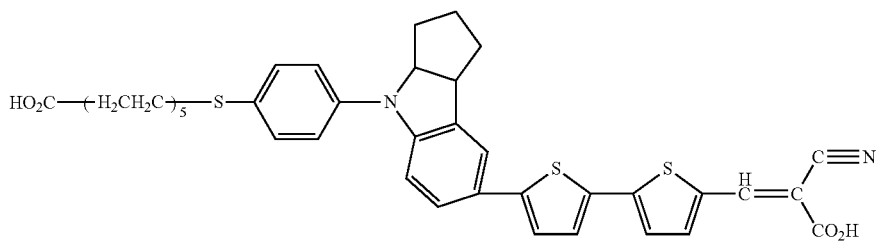

D-23

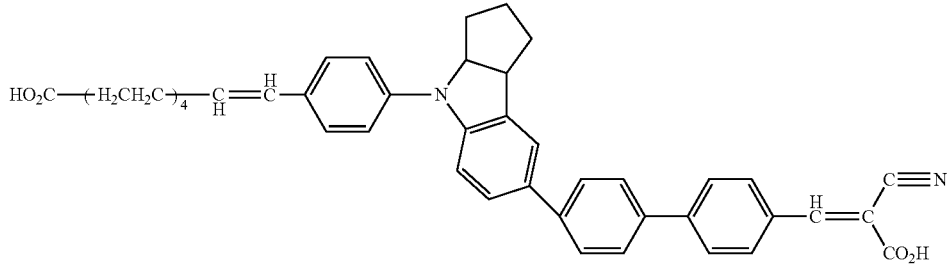

D-24

These compounds can be synthesized by consulting synthesis methods described, for example, in JP8-269345A, Japanese Translation Version No. 2004/011555 of PCT application, etc.

The dye-sensitized solar cell comprises an electrically conductive supporting material, a dye-sensitized semiconductor layer (semiconductor electrode) formed on the electrically conductive supporting material surface, a charge transfer layer and a counter electrode. The semiconductor layer may have the constitution of a single-layer structure or stacked-layers, and the constitution is designed depending upon purposes. In boundaries in this element, such as a boundary between the electrically conductive layer of the electrically conductive supporting material and the semiconductor layer, a boundary between the semiconductor layer and the transfer layer, etc., a component constituting one layers and a component constituting the other layer may be diffused into, or may be mixed with, each other.

The electrically conductive supporting material can be selected from a metal substrate of which the substrate itself has electric conductivity or a glass or plastic supporting material of which the surface has an electrically conductive layer containing an electrically conductive agent. In the latter case, the electrically conductive agent includes metals such as platinum, gold, silver, copper, aluminum, etc., carbon, an indium-tin composite oxide (to be abbreviated as "ITO" hereinafter), a metal oxide such as tin oxide doped with fluorine (to be abbreviated as "FTO" hereinafter), etc. The electrically conductive supporting material preferably has light transparency sufficient for transmitting 10% or more of light, more preferably transmitting 50% or more. Above all, it is particularly preferable an electrically conductive glass is obtained by depositing an electrically conductive layer formed of ITO or FTO on a glass.

A metal lead wire may be used for the purpose of decreasing the resistance of the transparent electrically conductive substrate. The material for the metal lead wire includes metals such as aluminum copper, silver, gold, platinum, nickel, etc. The metal lead wire is provided on a transparent electrically conductive supporting material by vapor deposition, sputtering or press-contacting, and ITO or FTO is formed thereon, or the metal lead wire is provided on a transparent substrate having an electrically conductive surface.

The semiconductor includes element semiconductors such as silicon and germanium, compound semiconductors typified by chalcogenides and compounds having a perovskite structure each. The chalcogenide of metal preferably includes oxides of titanium, tin, zinc, iron, tungsten, zirconium, hafnium, strontium, indium, cerium, yttrium, lanthanum, vanadium, niobium and tantalum, sulfides of cadmium, zinc, lead, silver, antimony and bismuth, selenide of lead, and telluride of cadmium. The other compound semiconductor preferably includes phosphorus compounds of zinc, gallium, indium, cadmium, etc., gallium arsenide, copper-indium-selenide, copper-indium-sulfide, etc. The compounds having a perovskite structure each includes strontium titanate, calcium titanate, sodium titanate, barium titanate, potassium niobate, etc.

The semiconductor for use in this invention may be a single crystal or may be a polycrystal. From the viewpoint of photoelectric conversion efficiency, a single crystal is preferred. From the viewpoint of a production cost and raw material availability, a polycrystal is preferred. The grain size of the semiconductor is preferably 2 nm or more and 1 µm or less.

The method for forming the semiconductor layer on the electrically conductive supporting material includes a method in which a dispersion or colloid solution of semiconductor fine particles is applied onto the electrically conductive supporting material and a sol-gel method. The method for preparing the dispersion includes a sol-gel method, a method in which a semiconductor is mechanically pulverized in a mortar, a method in which it is dispersed while pulverizing it with a mill, and a method in which a semiconductor is precipitated as fine particles during the synthesis of the semiconductor and is used as it is.

When a dispersion is prepared by mechanical pulverization or pulverization with a mill, it is prepared by dispersing at least semiconductor fine particles alone or a mixture of semiconductor fine particles with a resin in water or an organic solvent.

The resin that is used includes polymers or copolymers of vinyl compounds such as styrene, vinyl acetate, acrylic ester, methacrylic ester, etc., a silicone resin, a phenoxy resin, a polysulfone resin, a polyvinyl butyral resin, a polyvinyl formal resin, a polyester resin, a cellulose ester resin, a cellulose ether resin, a urethane resin, a phenolic resin, an epoxy resin, a polycarbonate resin, a polyallylate resin, a polyamide resin, a polyimide resin, etc.

The medium for dispersing the semiconductor fine particles includes water, alcohol media such as methanol, ethanol, isopropyl alcohol, etc., ketone media such as acetone, methyl ethyl ketone, methyl isobutyl ketone, etc., ester media such as ethyl formate, ethyl acetate, n-butyl acetate, etc., ether media such as diethyl ether, dimethoxyethane, tetrahydrofuran, dioxolane, dioxane, etc., amide media such as N,N-dimethylformamide, N,N-dimethylacetamide, N-methyl-2-pyrrolidone, etc., halogenated hydrocarbon media such as dichloromethane, chloroform, bromoform, methyl iodide, dichloroethane, trichloroethane, trichloroethylene, chlorobenzene, o-dichlorobenzene, fluorobenzene, bromobenzene, iodobenzene, 1-chloronapthalene, etc., and hydrocarbon media such as n-pentane, n-hexane, n-octane, 1,5-hexadiene, cyclohexane, methylcyclohexane, cyclohexadiene, benzene, toluene, o-xylene, m-xylene, p-xylene, ethylbenzene, cumene, etc. These may be used singly or as mixed media of two or more of them.

The method for applying the dispersion includes a roll method, a dip method, an air knife method, a blade method, a wire bar method, a slide hopper method, an extrusion method, a curtain method, a spin method, and a spray method.

The semiconductor layer may be a single layer or stacked layers. When it is formed of stacked layers, dispersions of semiconductor particles different in particle diameter may be applied to form stack layers, or different semiconductors or application layers different in composition of resin and additive may be applied to form stacked layers. When a film thickness is insufficient when application is carried out once, applications for forming stacked layers are effective means.

Generally, with an increase in the thickness of the semiconductor, the amount of the dye held therein per a unit projection area increases, and hence the light capture ratio increases. However, the diffusion distance of generated electrons increases, and hence recombinations of charges increase. Therefore, the film thickness of the semiconductor layers is preferably 0.1 to 100 µm, more preferably 1 to 30 µm.

After the semiconductor fine particles are applied onto the electrically conductive supporting material, the applied semiconductor fine particles may be heat-treated or may not be heat-treated. For improving electronic contact of the fine particles and film strength and improving the adhesion between the fine particles and the supporting material, it is preferred to carry out the heat treatment. Further, irradiation with microwave, press-treatment or irradiation with electron beam may be carried out. One of these treatments may be carried out singly, or two or more treatments may be carried out. In the heat treatment, the heating temperature is preferably 40 to 700° C., more preferably 80 to 600° C., and the heating time period is preferably 5 minutes to 50 hours, more preferably 10 minutes to 20 hours. In the irradiation with microwave, microwave may be applied to the semiconductor layer formation side of the semiconductor electrode, or may be applied to the reverse side thereof. The irradiation time period is not specially limited, while the irradiation is preferably completed within 1 hour. The press-treatment is preferably carried out at $9.8 \times 10^6$ N/m$^2$ or more, more preferably carried out at $9.8 \times 10^7$ N/m$^2$ or more. The pressing time period is not specially limited, while it is preferably completed within 1 hour.

The semiconductor fine particles are preferably fine particles having larger surface areas for adsorbing a larger amount of the dye. The surface area of the semiconductor fine particles in a state where the semiconductor layer is application-formed on the supporting material is preferably 10 times, more preferably 100 times, as large as the projection area.

The dye of the general formula [I], [II], [III] or [IV] for dye-sensitized solar cells in this invention may be used singly, or may be used in combination of two or more of them. For the purpose of reducing the amount of ruthenium (Ru) that is used in the dye-sensitized solar cell using ruthenium (Ru), further, the dye(s) of this invention and a Ru complex may be used in combination. The dye(s) of this invention may used in combination with other melocyanine dye, cyanine dye, a 9-phenylxanthene-containing dye, a coumarin-containing dye, a phthalocyanine-containing dye, a naphthalocyanine-containing dye, etc.

The method of causing the semiconductor layer to adsorb the dye includes a method in which a working electrode containing semiconductor fine particles is immersed in a dye solution or dye dispersion and a method in which a dye solution or dispersion is applied to the semiconductor layer to cause the semiconductor layer to adsorb the dye. In the former case, a dip method, a roller method, an airknife method, etc., can be used, and in the latter case, a wire bar method, a slide hopper method, an extrusion method, a curtain method, a spin method, a spray method, etc., can be used.

A condensation agent may be used together when the dye is adsorbed. The condensation agent may be any one of an agent that is supposed to work as a catalyst for physically or chemically bonding the dye to an inorganic substance surface and an agent that stoichiometrically works to shift a chemical equilibrium advantageously. Further, a thiol or a hydroxy compound may be added as a condensation auxiliary.

The medium for dissolving or dispersing the dye includes water, alcohol media such as methanol, ethanol, isopropyl alcohol, etc., ketone media such as acetone, methyl ethyl ketone, methyl isobutyl ketone, etc., ester media such as ethyl formate, ethyl acetate, n-butyl acetate, etc., ether media such as diethyl ether, dimethoxyethane, tetrahydrofuran, dioxolane, dioxane, etc., nitrile media such as acetonitrile, propionitrile, etc., amide media such as N,N-dimethylformamide, N,N-dimethylacetamide, N-methyl-2-pyrrolidone, etc., halogenated hydrocarbon media such as dichloromethane, chloroform, bromoform, methyl iodide, dichloroethane, trichloroethane, trichloroethylene, chlorobenzene, o-dichlorobenzene, fluorobenzene, bromobenzene, iodobenzene, 1-chloronapthalene, etc., and hydrocarbon media such as n-pentane, n-hexane, n-octane, 1,5-hexadiene, cyclohexane, methylcyclohexane, cyclohexadiene, benzene, toluene, o-xylene, m-xylene, p-xylene, ethylbenzene, cumene, etc. These may be used singly or as mixed media of two or more of them.

The temperature for causing the dye to be adsorbed is preferably −50° C. or higher but 200° C. or lower. Further, the adsorption may be carried out with stirring. As a method for stirring, there may be employed a stirrer, a ball mill, a paint conditioner, a sand mill, an attriter, a disperser or ultrasonic dispersion, while the method shall not be limited thereto. The time period that the adsorption requires is preferably 5 seconds or more but 1,000 hours or less, more preferably 10 seconds or more but 500 hours or less, still more preferably 1 minute or more but 150 hours or less.

When the semiconductor layer is caused to adsorb the dye, a steroid-containing compound may be used in combination for co-adsorption.

Specific examples of the steroid-containing compound are as shown as E1-E10. The amount of the steroid-containing compound per 1 part by mass of the dye is preferably 0.01 to 1,000 parts by mass, more preferably 0.1 to 100 parts by mass.

[CF45]

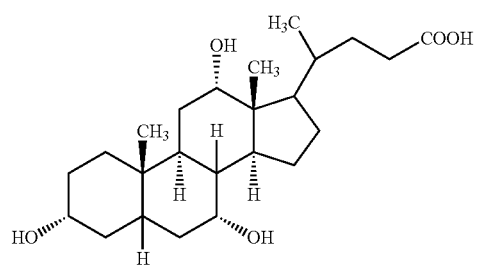

E1

-continued

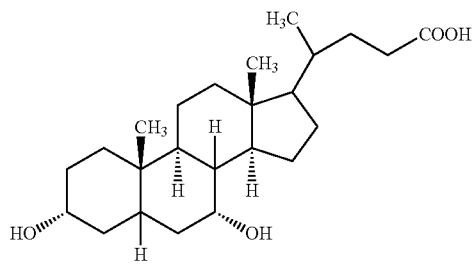

E2

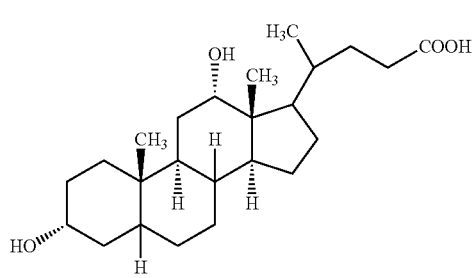

E3

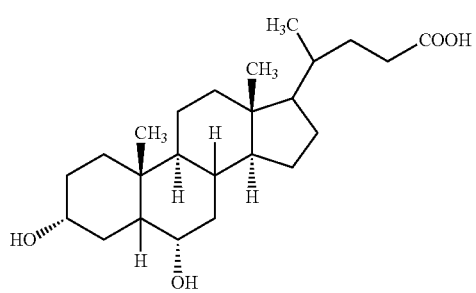

E4

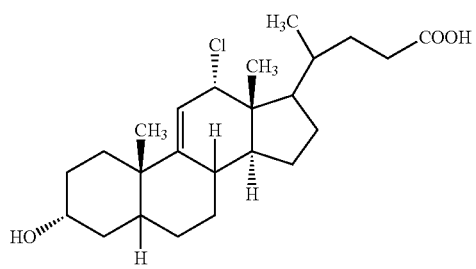

E5

[CF46]

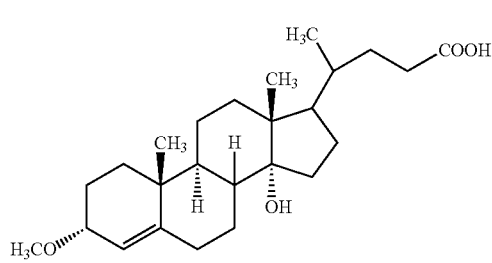

E6

-continued

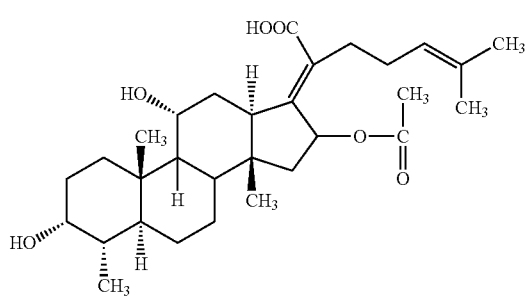
E7

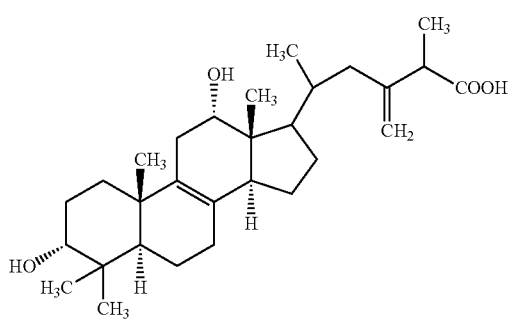
E8

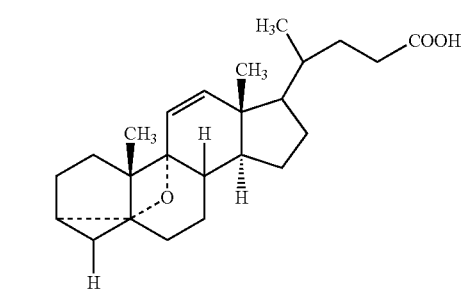
E9

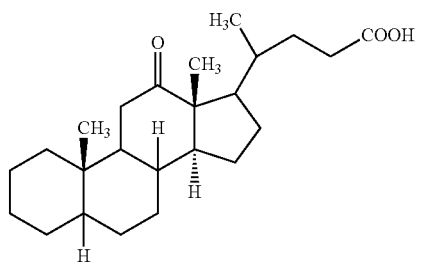
E10

After the dye is adsorbed or the dye and the above steroid-containing compound are co-adsorbed, an intermediate product may be immersed in an organic solvent containing a basic compound such as t-butylpyridine, 2-picoline, 2,6-lutidine, etc., or an acidic compound such as phosphoric acid, phosphoric ester, alkyl phosphate, acetic acid, propionic acid, etc.

For the charge-transporting layer, there can be used an electrolytic solution prepared by dissolving an oxidation-reduction pair in an organic solvent, a gel electrolyte prepared by impregnating a polymer matrix with a solution of an oxidation-reduction pair in an organic solvent, a molten salt containing an oxidation-reduction pair, a solid electrolyte, an inorganic hole-transporting substance, an organic hole-transporting substance, etc.

The electrolytic solution is preferably composed of an electrolyte, a solvent and an additive. The electrolyte preferably includes combinations of metal iodide-iodine such as lithium iodide, sodium iodide, potassium iodide, cesium iodide, calcium iodide, etc., combinations of iodide of quaternary ammonium compounds such as tetralkylammonium iodide, pyridinium iodide, imidazolium iodide, etc., combinations of a metal bromide-bromine such as lithium bromide, sodium bromide, potassium bromide, cesium bromide, calcium bromide, etc., combinations of bromide of quaternary ammonium compounds such as tetraalkylammonium bromide, pyridinium bromide, etc., metal complexes such as ferrocyanate-ferricyanate, ferrocene-ferricynium ion, etc., sulfur compounds such as polysodium sulfide, alkylthiol-alkyl disulfide, etc., viologen dye, hydroquinone-quinone, etc. The above electrolytes may be used singly or may be used in combination of two or more of them. Further, an electrolyte that is a salt in a molten state at room temperature may be also used. When a molten salt is used, no solvent may be used in particular.

The electrolyte concentration in the electrolytic solution is preferably 0.05 to 20 M, more preferably 0.1 to 15 M. The solvent for use with the electrolyte preferably includes carbonate solvents such as ethylene carbonate, propylene carbonate, etc., heterocyclic compounds such as 3-methyl-2-oxazolidine, etc., ether solvents such as dioxane, diethyl ether, ethylene glycol dialkyl ether, etc., alcohol solvents such as methanol, ethanol, polypropylene glycol monoalkyl ether, etc., nitrile solvents such as acetonitrile, benzonitrile, etc., and aprotic polar solvents such as dimethylsulfoxide, sulfolane, etc. Further, basic compounds such as t-butyl pyridine, 2-picoline, 2,6-lutidine, etc., may be used in combination with the above solvent.

The electrolyte can be gelated by the technique of adding a polymer, adding an oil gelation agent, polymerization including polyfunctional monomers, a crosslinking reaction of a polymer, etc. When it is gelated by adding a polymer, the polymer is preferably selected from polyacrylonitrile, polyvinylidene fluoride, etc. When it is gelated by adding an oil gelation agent, the gelation agent is preferably selected from dibenzylidene-D-sorbitol, a cholesterol derivative, an amino acid derivative, an alkylamide derivative of trans-(1R,2R)-1,2-dyclohexanediamine, an alkylurea derivative, N-octyl-D-gluconamidebenzoate, a double head amino acid derivative, a quaternary ammonium derivative, etc.

When polymerization is carried out with polyfunctional monomers, the monomers preferably include divinyl benzene, ethylene glycol dimethacrylate, ethylene glycol diacrylate, diethylene glycol dimethacrylate, triethylene glycol dimethacrylate, pentaerythritol acrylate, trimethylolpropane triacrylate, etc. Further, contain monofunctional monomers including esters and amides derived from acrylic acid or α-alkylacrylic acid such as acrylamide, methyl acrylate, etc., esters derived from maleic acid or fumaric acid such as dimethyl maleate, diethyl fumarate, etc., dienes such as butadiene, cyclopentadiene, etc., aromatic vinyl compounds such as styrene, p-chlorostyrene, sodium styrenesulfonate, etc., vinyl esters, acrylonitrile, methacrylonitrile, a vinyl compound having a nitrogen-containing heterocyclic ring, a vinyl compound having a quaternary ammonium salt, N-vinylformamide, vinylsulfonic acid, vinylidene fluoride, vinyl alkyl ethers, N-phenylmaleimide, etc. The amount of the polyfunctional monomer based on the total amount of the monomers is preferably 0.5 to 70% by mass, more preferably 1.0 to 50% by mass.

The above monomers can be polymerized by radical polymerization. The monomer that can be used in this invention for a gel electrolyte can be radical-polymerized by applying heat, light, an electron beam or electrochemistry. The polymerization initiator that is used for forming a crosslinked polymer is preferably selected from azo initiators such as 2,2'-azobisisobutyronitrile, 2,2'-azobis(2,4-dimethylvaleronitrile), dimethyl-2,2'-azobis(2-methyl)propionate, etc., peroxide initiators such as benzoyl peroxide, etc., and the like. The amount of the polymerization initiator based on the total amount of the monomers is preferably 0.01 to 20% by mass, more preferably 0.1 to 10% by mass.

When the electrolyte is gelated by the crosslinking reaction of a polymer, it is preferred to use a polymer having a reactive group necessary for a crosslinking reaction and a crosslinking agent in combination. Examples of the reactive group necessary for the crosslinking reaction preferably include nitrogen-containing heterocyclic rings such as pyridine, imidazole, thiazole, oxazole, triazole, morpholine, piperidine, piperazine, etc. The crosslinking agent preferably includes trifunctional or higher agents capable of performing an electrophilic reaction with a nitrogen atom, such as alkyl halide, aralkyl halide, sulfonic ester, acid anhydride, acid chloride, isocyanate, etc.

When an inorganic hole-transporting substance is used in place of the electrolyte, copper iodide, copper thiocyanide, etc., can be introduced into an electrode by a method such as a casting method, an application method, a spin coating method, an immersion method, electric plating, etc.

Further, an organic charge-transporting substance can be also used in place of the electrolyte. The charge-transporting substance includes a hole-transporting substance and an electron-transporting substance. Examples of the former include oxadiazoles disclosed in JP 34-5466B, etc., triphenylmethanes disclosed in JP 45-555B, etc., pyrazolines disclosed in JP 52-4188B, etc., hydrazones disclosed in JP 55-42380B, etc., oxadiazoles disclosed in JP 56-123544A, tetraarylbenzidines disclosed in 54-58445A, and stilbenes disclosed in JP 58-65440A or JP 60-98437A. Of these, hydrazones disclosed in JP 60-24553A, JP 2-96767A, JP 2-183260A and JP 2-226160A, and stilbenes disclosed in JP 2-51162A and JP 3-75660A are particularly preferred as a charge-transporting substance that can be used in this invention. These may be used singly or as a mixture of two or more of them.

The electron-transporting substance includes chloranil, tetracyanoethylene, tetracyanoquinodimethane, 2,4,7-trinitro-9-fluorenone, 2,4,5,7-tetranitro-9-fluorenone, 2,4,5,7-tetranitroxanthone, 2,4,8-trinitrothioxanthone, 1,3,7-trinitrodibenzothiophene, 1,3,7-trinitrobenzothiophene-5,5-dioxide, etc. These electron-transporting substances may be used singly or as a mixture of two or more of them.

For improving the charge transfer efficiency in the charge-transporting layer, an electron-attracting compound of some kind may be added to the charge-transporting layer. Examples of the electron-attracting compound above include quinones such as 2,3-dichloro-1,4-naphthoquinone, 1-nitroanthraquinone, 1-chloro-5-nitroanthraquinone, 2-chloroanthraquinone, phenanthrenequinone, etc., aldehydes such as 4-nitrobenzaldehyde, ketones such as 9-benzoylanthracene, indanedione, 3,5-dinitrobenzophenone, 3,3',5,5'-tetranitrobenzophenone, etc., acid anhydrides such as phthalic anhydride, 4-chloronaphthalic anhydride, etc., cyano compounds such as terephtalalmalononitrile, 9-anthrylmehylidenemalononitrile, 4-nitrobenzalmalononitrile, 4-(p-nitrobenzoyloxy)benzalmalononitrile, etc., phthalides such as 3-benzalphthalide, 3-(α-cyano-p-nitrobenzal)phthalide, 3-(α-cyano-p-nitrobenzal)-4,5,6,7-tetrachlorophthalide, etc., and the like.

When the charge-transporting layer is formed from a charge-transporting material, a resin may be used in combination. When the resin is used in combination, the resin is selected from a polystyrene resin, a polyvinyl acetal resin, a polysulfone resin, a polycarbonate resin, a polyester resin, a polyphenylene oxide resin, a polyallylate resin, an acrylic resin, a methacrylic resin, a phenoxy resin, etc. Of these, a polystyrene resin, a polyvinyl acetal resin, a polycarbonate resin, a polyester resin and a polyallylate resin are preferred. These resins may be used singly or as a mixture of two or more of them as a copolymer.

The method of forming the charge-transporting layer largely includes two methods. In one method, a counter electrode is first stacked on the semiconductor layer having the dye adsorbed, and the charge-transporting layer in the form of a liquid is inserted in a space between them. In the other method, the charge-transporting layer is provided on the semiconductor layer having the dye adsorbed. In the latter method, the counter electrode is newly provided on the charge-transporting layer.

In the former method, the method of inserting the charge-transporting layer includes an atmospheric-pressure process using capillarity in immersion and a vacuum process in which a gaseous phase is replaced with a liquid phase by employing a pressure lower than atmospheric pressure. In the latter case, it is required to provide the counter electrode while the charge-transporting layer in a wet state is not dried, so that the leak of liquid in an edge portion is prevented. In a gel electrolyte, there is also a method in which it is applied by a wet method and then solidified by the method of polymerization, etc. In this case, the counter electrode may be provided after it is dried and cured. As a method of imparting not only an electrolytic solution but also a solution of an organic charge-transporting material or a gel electrolyte, there are an immersion method, a roller method, a dip method, an airknife method, an extrusion method, a slide hopper method, a wire-bar method, a spin method, a spray method, a cast method, various printing methods, etc., like the semiconductor layer or the dye is imparted.

The counter electrode can be used on a supporting material having an electrically conductive layer on a surface like the above substrate having an electrically conductive layer on a surface, while the supporting material is not necessarily required when the electrically conductive layer itself fully has strength and the property of tight sealing. Specific examples of the material for the counter electrode include metals such as platinum, gold, silver, copper, aluminum, rhodium, indium, etc., a carbon-containing compound, and electrically conductive metal oxides such as ITO, FTO, etc. The thickness of the counter electrode is not specially limited.

For light reaching the semiconductor layer, at least one of the substrate having electric conductivity on a surface holding the semiconductor layer and the counter electrode is required to be transparent. In the photoelectric conversion element of this invention, preferably, the substrate having electric conductivity on a surface holding the semiconductor fine particles is transparent, and there is employed a method in which sunlight is caused to enter from the side of the electrically conductive substrate holding the semiconductor layer. In this case, the counter electrode is formed from a material that reflects light, and a glass or plastic prepared by the vapor-deposition of a metal or electrically conductive oxide or a metal thin film is preferred.

The counter electrode is provided as described above, and there are two cases, one in which it is provided on the charge-transporting layer and the other in which it is provided on the semiconductor layer. In each case, the counter electrode can be formed on the charge-transporting layer or the semiconductor layer by the method of application, laminating, vapor deposition, stacking, etc., as required depending upon the materials of the counter electrode and the kinds of the charge transfer layer. When the charge-transporting layer is a solid, the counter electrode can be formed directly thereon by the method of applying, vapor deposition, chemical vapor deposition (CVD), etc., of the above electrically conductive material.

EXAMPLES

This invention will be explained further in detail hereinafter with reference to Examples, while this invention shall not be limited by these Examples.

Synthesis Example 1

Synthesis of Dye A-7

1.0 Gram of an intermediate A, 0.4 g of an intermediate B, 0.05 g of ammonium acetate and 20 ml of acetic acid were mixed, and the mixture was heated at a bath temperature of 120° C. for 7 hours. Then, the reaction mixture was cooled to room temperature, and a precipitated solid was recovered by filtering and washed with 50 ml of acetic acid and then with 50 ml of water, and it was further washed with 20 ml of methanol and then dried to give 1.1 g of a crude product. This crude product was purified by silica gel column chromatography (eluent solvents: chloroform/methanol=10/1 (volume ratio)) to give 0.9 g of Dye A-7.

Absorption maximum (N,N-dimethylformamide solution): 485 nm

Synthesis Example 2

Synthesis of Dye A-3

1.7 Grams of an intermediate C, 0.8 g of an intermediate B, 0.05 g of ammonium acetate and 40 ml of acetic acid were mixed, and the mixture was heated at a bath temperature of 120° C. for 7 hours. Then, the reaction mixture was cooled to room temperature, and a precipitated solid was recovered by filtering and washed with 50 ml of acetic acid and then with 50 ml of water, and it was further washed with 20 ml of methanol and then dried to give 2.0 g of a crude product. This crude product was purified by silica gel column chromatography (eluent solvents: chloroform/methanol=10/1 (volume ratio)) to give 1.6 g of Dye A-3.

Absorption maximum (methanol solution): 490 nm

[CF47]

Intermediate A $HO_2C-(H_2CH_2C)_5-S-$ ...

Intermediate B

Intermediate C $HO_2C-H_2CH_2CH_2CH_2CH_2C-S-$ ...

Synthesis Example 3

Synthesis of Dye B-3

2.2 Grams of an intermediate D, 2.3 g of an intermediate E, 0.1 g of ammonium acetate and 200 ml of acetic acid were mixed, and the mixture was heated at a bath temperature of 120° C. for 6 hours. Then, the reaction mixture was cooled to room temperature, and a precipitated solid was recovered by filtering and washed with 80 ml of acetic acid and then with 160 ml of water, and it was further washed with 140 ml of methanol and then dried to give 2.0 g of a crude product. This crude product was purified by silica gel column chromatography (eluent solvents: chloroform/methanol=3/1 (volume ratio)) to give 1.6 g of Dye B-3.

Absorption maximum (N,N-dimethylformamide solution): 530 nm

Synthesis Example 4

Synthesis of Dye B-12

2.2 Grams of an intermediate D, 2.8 g of an intermediate F, 0.1 g of ammonium acetate and 200 ml of acetic acid were mixed, and the mixture was heated at a bath temperature of 120° C. for 6 hours. Then, the reaction mixture was cooled to room temperature, and a precipitated solid was recovered by filtering and washed with 80 ml of acetic acid and then with 160 ml of water, and it was further washed with 140 ml of methanol and then dried to give 1.9 g of a crude product. This crude product was purified by silica gel column chromatography (eluent solvents: chloroform/methanol=3/1 (volume ratio)) to give 1.5 g of Dye B-12.

Absorption maximum (N,N-dimethylformamide solution): 530 nm

[CF48]

Intermediate D

Synthesis Example 5

Synthesis of Dye B-39

2.0 Grams of an intermediate A, 1.7 g of an intermediate G, 0.1 g of ammonium acetate and 200 ml of acetic acid were mixed, and the mixture was heated at a bath temperature of 120° C. for 5 hours. Then, the reaction mixture was cooled to room temperature, and a precipitated solid was recovered by filtering and washed with 80 ml of acetic acid and then with 160 ml of water, and it was further washed with 140 ml of methanol and then dried to give 2.0 g of a crude product. This crude product was purified by silica gel column chromatography (eluent solvents: chloroform/methanol=10/1 (volume ratio)) to give 1.7 g of Dye B-39.

Absorption maximum (N,N-dimethylformamide solution): 524 nm

Synthesis Example 6

Synthesis of Dye B-41

2.0 Grams of an intermediate A, 2.4 g of an intermediate H, 0.1 g of ammonium acetate and 200 ml of acetic acid were mixed, and the mixture was heated at a bath temperature of 120° C. for 6 hours. Then, the reaction mixture was cooled to room temperature, and a precipitated solid was recovered by filtering and washed with 80 ml of acetic acid and then with 160 ml of water, and it was further washed with 140 ml of methanol and then dried to give 2.0 g of a crude product. This crude product was purified by silica gel column chromatography (eluent solvents: chloroform/methanol=10/1 (volume ratio)) to give 1.8 g of Dye B-41.

Absorption maximum (N,N-dimethylformamide solution): 524 nm

Synthesis Example 7

Synthesis of Dye C-8

2.0 Grams of an intermediate C, 2.2 g of an intermediate I, 0.1 g of ammonium acetate and 400 ml of acetic acid were mixed, and the mixture was heated at a bath temperature of 120° C. for 10 hours. Then, the reaction mixture was cooled to room temperature, and a precipitated solid was recovered by filtering and washed with 80 ml of acetic acid and then with 160 ml of water, and it was further washed with 80 ml of methanol and then dried to give 3.1 g of a crude product. This crude product was purified by silica gel column chromatography (eluent solvents: chloroform/methanol=3/1 (volume ratio)) to give 2.3 g of Dye C-8.

Absorption maximum (N,N-dimethylformamide solution): 553 nm

Synthesis Example 8

Synthesis of Dye D-7

2.0 Grams of an intermediate A, 1.1 g of cyanoacetic acid, 0.8 g of piperidine and 80 ml of acetonitrile were mixed, and the mixture was refluxed under heat at a bath temperature of 90° C. for 5 hours. Then, the reaction mixture was cooled to room temperature, the solvent was cast away by decantation, and a precipitated oily product was taken out. The oily product was dissolved in 200 ml of chloroform and washed with 20 ml of 1 mol/1 of hydrochloric acid. A chloroform solution was separated and recovered, washed with 50 ml of water three times and dried over anhydrous magnesium sulfate, and chloroform was distilled off under reduced pressure with a rotary evaporator to give 1.8 g of a crude product. This crude product was purified by silica gel column chromatography (eluent solvents: chloroform/methanol=3/1 (volume ratio)) to give 1.6 g of Dye D-7.

Absorption maximum (methanol solution): 415 nm

Synthesis Example 9

Synthesis of Dye D-3

1.8 Grams of an intermediate C, 1.1 g of cyanoacetic acid, 0.8 g of piperidine and 80 ml of acetonitrile were mixed, and the mixture was refluxed under heat at a bath temperature of 90° C. for 5 hours. Then, the reaction mixture was cooled to room temperature, the solvent was cast away by decantation, and a precipitated oily product was taken out. The oily product was dissolved in 200 ml of chloroform and washed with 20 ml of 1 mol/l of hydrochloric acid. A chloroform solution was separated and recovered, washed with 50 ml of water three times and dried over anhydrous magnesium sulfate, and chloroform was distilled off under reduced pressure with a rotary evaporator to give 1.7 g of a crude product. This crude product was purified by silica gel column chromatography (eluent solvents: chloroform/methanol=3/1 (volume ratio)) to give 1.5 g of Dye D-3.

Absorption maximum (methanol solution): 442 nm

Example 1

<Making of Dye-Sensitized Solar Cell>

2 Grams of titanium oxide (trade name: P-25, supplied by NIPPON AEROSIL CO., LTD.), 0.2 g of acetylacetone and 0.3 g of a surfactant (trade name: Triton X-100, supplied by Sigma-Aldrich Co.) were dispersed with a paint conditioner (supplied by Red Devil Inc.) together with 6.5 g of water for 6 hours. Further, to 4.0 g of this dispersion were added 0.2 ml of concentrated nitric acid, 0.4 ml of ethanol and 1.2 g of polyethylene glycol (#20,000), to prepare a paste. The paste was applied to an FTO glass substrate so as to form a layer having a thickness of 10 and the applied paste was dried at room temperature and heated at 100° C. for 1 hour and further at 550° C. for 1 hour to give a semiconductor electrode.

Dye A-7 was dissolved in tetrahydrofuran to prepare a dye solution having a concentration of 0.3 mM. The above-prepared semiconductor electrode was immersed and so kept in the dye solution at room temperature for 5 hours to carry out adsorption treatment, thereby to make a dye-adsorbed semiconductor electrode (work electrode). As a counter electrode, an electrode obtained by sputtering platinum on a titanium plate was used. These two electrodes were arranged such that they faced each other, and an electrolytic solution was injected between them to make a dye-sensitized solar cell. As an electrolytic solution, there was used a solution of 0.1 M of lithium iodide, 0.05 M of iodine, 0.5 M of 1,2-dimethyl-3-n-propylimidazolium iodide and 0.05 M of 4-t-butylpyridine in 3-methoxypropionitrile.

<Evaluation 1: Photoelectric Conversion Efficiency>

Artificial sunlight (AM1.5G, irradiation intensity 100 mW/cm$^2$) generated from a solar simulator (apparatus name: YSS-40S, supplied by Yamashita Dense Corporation) as a light source was applied to the dye-sensitized solar cell from the work electrode side, and the dye-sensitized solar cell was evaluated for photoelectric conversion efficiency with an electrochemical measuring apparatus (apparatus name: SI-1280B, supplied by Solartron). Table 3 shows the result.

<Evaluation 2: Durability>

After a dye-sensitized solar cell was stored in a 65° C. environment for 14 days, it was evaluated for photoelectric conversion efficiency. Further, a stability ratio of the photoelectric conversion efficiency was determined. The stability ratio of the photoelectric conversion efficiency was calculated as a percentage of the photoelectric conversion efficiency after storage to the photoelectric conversion efficiency before storage. Table 4 shows the result.

<Evaluation 3: Adsorption Stability>

Dye A-7 was dissolved in tetrahydrofuran to prepare a dye solution having a concentration of 0.3 mM. A semiconductor electrode was immersed in the dye solution at room temperature for 8 hours to carry out adsorption treatment, and a dye-adsorbed semiconductor electrode (work electrode) was thus made. The dye-adsorbed semiconductor electrode was immersed in 3-methoxypropionitrile that was a solvent for the electrolyte, and stored at room temperature for 30 days in a dark and being hermetically sealed. After the storage, a state on the surface of the electrode in which the dye was held on the semiconductor was visually observed. Table 5 shows the result.

◯: No elution of a dye is observed.

Δ: The elution of a dye is partly observed.

Examples 2-20

Dye-sensitized solar cells were made in the same manner as in Example 1 except that Dye A-7 was replaced with dyes shown in Table 3, and they were evaluated. Tables 3 to 5 show the results.

Comparative Examples 1-6

Dye-sensitized solar cells were made in the same manner as in Example 1 except that Dye A-7 was replaced with comparative dyes F-1 to F-6, and they were evaluated. Tables 3 to 5 show the results.

[CF51]

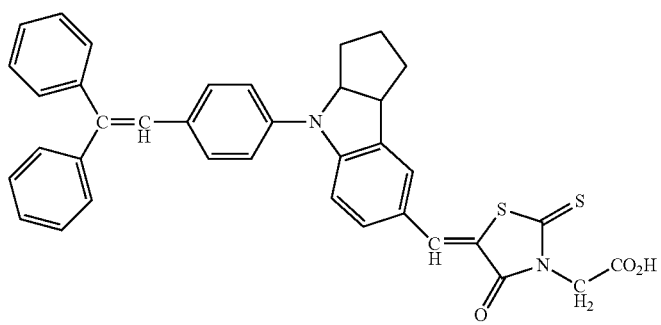

F-1

-continued
F-2
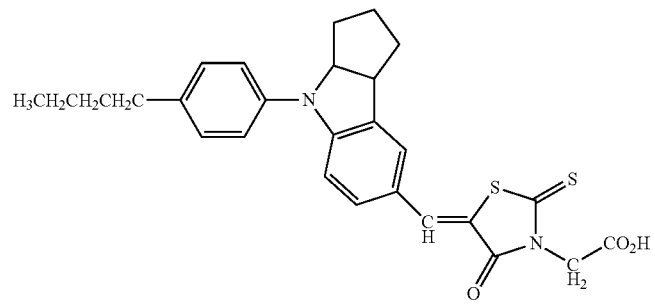
F-3
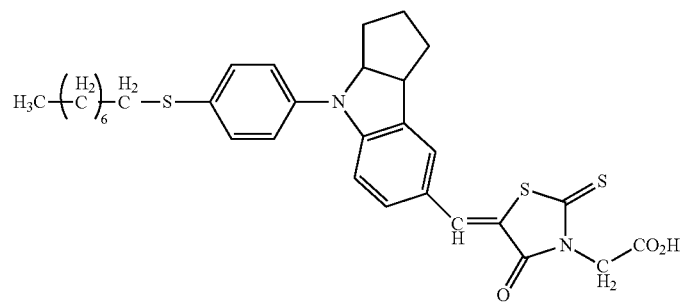
F-4
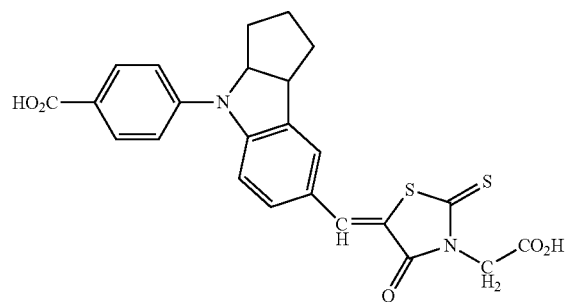
F-5
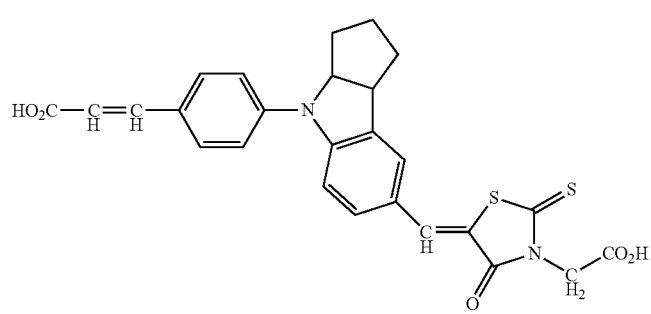
F-6
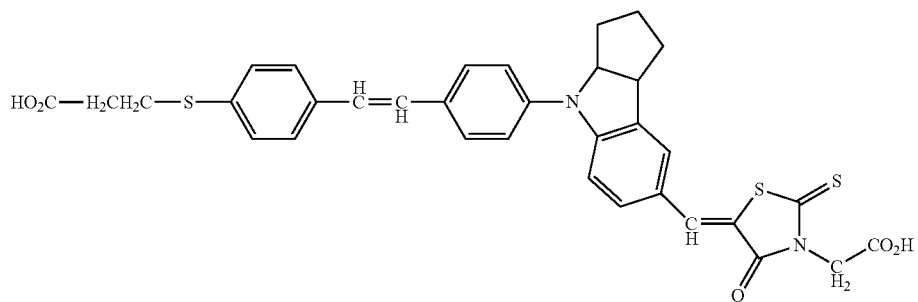

TABLE 3

| | Dye | Open circuit voltage V | Short circuit current density mA/cm² | Fill factor | Photoelectric conversion efficiency % |
|---|---|---|---|---|---|
| Ex. 1 | A-7 | 0.68 | 11.0 | 0.71 | 5.31 |
| Ex. 2 | A-1 | 0.67 | 10.9 | 0.68 | 4.97 |
| Ex. 3 | A-2 | 0.67 | 10.5 | 0.71 | 4.99 |
| Ex. 4 | A-3 | 0.68 | 11.1 | 0.68 | 5.13 |
| Ex. 5 | A-4 | 0.69 | 11.4 | 0.68 | 5.35 |
| Ex. 6 | A-5 | 0.69 | 11.1 | 0.69 | 5.28 |
| Ex. 7 | A-6 | 0.69 | 11.7 | 0.70 | 5.65 |
| Ex. 8 | A-8 | 0.69 | 10.0 | 0.68 | 4.69 |
| Ex. 9 | A-9 | 0.70 | 12.0 | 0.69 | 5.80 |
| Ex. 10 | A-10 | 0.71 | 12.5 | 0.68 | 6.04 |
| Ex. 11 | A-11 | 0.69 | 12.2 | 0.67 | 5.64 |
| Ex. 12 | A-12 | 0.70 | 12.3 | 0.65 | 5.60 |
| Ex. 13 | A-13 | 0.68 | 10.8 | 0.65 | 4.77 |
| Ex. 14 | A-14 | 0.67 | 10.2 | 0.63 | 4.31 |
| Ex. 15 | A-15 | 0.67 | 10.1 | 0.67 | 4.53 |
| Ex. 16 | A-16 | 0.69 | 11.6 | 0.69 | 5.52 |
| Ex. 17 | A-17 | 0.70 | 10.3 | 0.65 | 4.69 |
| Ex. 18 | A-18 | 0.70 | 10.1 | 0.64 | 4.52 |
| Ex. 19 | A-19 | 0.68 | 11.2 | 0.64 | 4.87 |
| Ex. 20 | A-20 | 0.70 | 10.3 | 0.63 | 4.54 |
| CEx. 1 | F-1 | 0.64 | 11.3 | 0.68 | 4.92 |
| CEx. 2 | F-2 | 0.65 | 10.5 | 0.67 | 4.57 |
| CEx. 3 | F-3 | 0.67 | 10.1 | 0.67 | 4.53 |
| CEx. 4 | F-4 | 0.61 | 9.50 | 0.64 | 3.71 |
| CEx. 5 | F-5 | 0.62 | 9.60 | 0.64 | 3.81 |
| CEx. 6 | F-6 | 0.64 | 10.5 | 0.67 | 4.50 |

Ex. = Example, CEx. = Comparative Example

TABLE 4

| | Dye | Open circuit voltage V | Short circuit current density mA/cm² | Fill factor | Photoelectric conversion efficiency % | Stability ratio of photoelectric conversion efficiency % |
|---|---|---|---|---|---|---|
| Ex. 1 | A-7 | 0.68 | 10.8 | 0.70 | 5.15 | 97 |
| Ex. 2 | A-1 | 0.67 | 10.6 | 0.68 | 4.82 | 97 |
| Ex. 3 | A-2 | 0.67 | 10.3 | 0.70 | 4.84 | 97 |
| Ex. 4 | A-3 | 0.68 | 10.8 | 0.68 | 4.98 | 97 |
| Ex. 5 | A-4 | 0.69 | 11.1 | 0.67 | 5.14 | 96 |
| Ex. 6 | A-5 | 0.69 | 10.6 | 0.69 | 5.07 | 96 |
| Ex. 7 | A-6 | 0.69 | 11.5 | 0.69 | 5.48 | 97 |
| Ex. 8 | A-8 | 0.69 | 9.70 | 0.68 | 4.55 | 97 |
| Ex. 9 | A-9 | 0.70 | 11.8 | 0.68 | 5.63 | 97 |
| Ex. 10 | A-10 | 0.71 | 12.3 | 0.67 | 5.86 | 97 |
| Ex. 11 | A-11 | 0.69 | 11.8 | 0.67 | 5.47 | 97 |
| Ex. 12 | A-12 | 0.70 | 12.1 | 0.64 | 5.43 | 97 |
| Ex. 13 | A-13 | 0.68 | 10.4 | 0.65 | 4.58 | 96 |
| Ex. 14 | A-14 | 0.67 | 10.1 | 0.62 | 4.18 | 97 |
| Ex. 15 | A-15 | 0.67 | 9.69 | 0.67 | 4.35 | 96 |
| Ex. 16 | A-16 | 0.69 | 11.3 | 0.68 | 5.30 | 96 |
| Ex. 17 | A-17 | 0.70 | 10.2 | 0.64 | 4.55 | 97 |
| Ex. 18 | A-18 | 0.70 | 9.78 | 0.64 | 4.38 | 97 |
| Ex. 19 | A-19 | 0.68 | 10.8 | 0.64 | 4.68 | 96 |
| Ex. 20 | A-20 | 0.70 | 9.89 | 0.63 | 4.36 | 96 |
| CEx. 1 | F-1 | 0.62 | 8.28 | 0.67 | 3.44 | 70 |
| CEx. 2 | F-2 | 0.65 | 7.04 | 0.66 | 3.02 | 66 |
| CEx. 3 | F-3 | 0.67 | 6.55 | 0.67 | 2.94 | 65 |
| CEx. 4 | F-4 | 0.61 | 7.40 | 0.64 | 2.89 | 78 |
| CEx. 5 | F-5 | 0.62 | 7.81 | 0.63 | 3.05 | 80 |
| CEx. 6 | F-6 | 0.64 | 8.64 | 0.66 | 3.65 | 81 |

Ex. = Example, CEx. = Comparative Example

TABLE 5

| | Dye | Adsorption stability |
|---|---|---|
| Example 1 | A-7 | ○ |
| Example 2 | A-1 | ○ |
| Example 3 | A-2 | ○ |
| Example 4 | A-3 | ○ |
| Example 5 | A-4 | ○ |
| Example 6 | A-5 | ○ |
| Example 7 | A-6 | ○ |
| Example 8 | A-8 | ○ |
| Example 9 | A-9 | ○ |
| Example 1 | A-10 | ○ |
| Example 11 | A-11 | ○ |
| Example 12 | A-12 | ○ |
| Example 13 | A-13 | ○ |
| Example 14 | A-14 | ○ |
| Example 15 | A-15 | ○ |
| Example 16 | A-16 | ○ |
| Example 17 | A-17 | ○ |
| Example 18 | A-18 | ○ |
| Example 19 | A-19 | ○ |
| Example 21 | A-20 | ○ |
| CEx. 1 | F-1 | Δ |
| CEx. 2 | F-2 | Δ |
| CEx. 3 | F-3 | Δ |
| CEx. 4 | F-4 | ○ |
| CEx. 5 | F-5 | ○ |
| CEx. 6 | F-6 | ○ |

CEx. = Comparative Example

In Table 3, it is seen that the dyes of this invention each having the first acidic group in an electron acceptor unit and the second acidic group in an electron donor unit exhibit excellent photoelectric conversion efficiency. Further, it is seen that of the dyes of Comparative Examples, the dyes each having the first acidic group in the electron acceptor unit and having no second acidic group (F-1, F-2 and F-3) and the dye having the first acidic group in the electron acceptor unit and having an acidic group possessing a pKa of less than 6 bonded through an alkylene group having 2 carbon atoms in the electron donor unit (F-6) exhibit excellent photoelectric conversion efficiency. On the other hand, it is seen that the dyes each having the first acidic group in the electron acceptor unit and having an acidic group bonded directly to the sp² carbon atom constituting the π electron conjugated system of the electron donor unit (F-4, F-5) have low photoelectric conversion efficiency.

In Table 4, it is seen that the dyes of this invention have higher stability ratio of photoelectric conversion efficiency after storage at the 65° C. environment for 14 days than the dyes of Comparative Examples and hence have excellent durability.

In Table 5, it is seen that the dyes of this invention are also excellent in the stability of adsorption to the semiconductor electrode. Further, it is seen that of the dyes of Comparative Examples, F-1, F-2 and F-3 are poor in the stability of adsorption to the semiconductor electrode as compared with the dyes of this invention. Of the dyes of Comparative Examples, F-4, F-5 and F-6 are excellent in the adsorption stability.

When these results are summarized, it is seen that the dye of this invention has all of high photoelectric conversion efficiency, excellent durability and good adsorption stability.

Example 21

A dye-sensitized solar cell was made in the same manner as in Example 1 except that the concentration of 4-t-butylpyridine in an electrolytic solution was changed to 0.5 M, and it was evaluated for photoelectric conversion efficiency. Table 6 shows the result. The open circuit voltage changed by +0.05 V, the short circuit current density changed by −0.1 mA/cm², and the fill factor changed by +0.02, and as a result, the photoelectric conversion efficiency was improved by +0.50%.

Examples 22-40

Dye-sensitized solar cells were made in the same manner as in Examples 2 to 20 except that the concentration of 4-t-butylpyridine in an electrolytic solution was changed to 0.5 M, and they were evaluated for photoelectric conversion efficiency. Table 6 shows the results. Table 6 also shows differences in open circuit voltage and photoelectric conversion efficiency from Examples 2 to 20.

Comparative Examples 7-12

Dye-sensitized solar cells were made in the same manner as in Comparative Examples 1 to 6 except that the concentration of 4-t-butylpyridine in an electrolytic solution was changed to 0.5 M, and they were evaluated for photoelectric conversion efficiency. Table 6 shows the results. Table 6 also shows differences in open circuit voltage and photoelectric conversion efficiency from Comparative Examples 1 to 6.

TABLE 6

| | Dye | Open circuit voltage V | Short circuit current density mA/cm² | Fill factor | Photoelectric conversion efficiency % | Difference in open circuit voltage V | Difference in photoelectric conversion efficiency % |
|---|---|---|---|---|---|---|---|
| Ex. 21 | A-7 | 0.73 | 10.9 | 0.73 | 5.81 | +0.05 | +0.50 |
| Ex. 22 | A-1 | 0.73 | 10.8 | 0.70 | 5.52 | +0.06 | +0.55 |
| Ex. 23 | A-2 | 0.72 | 10.5 | 0.72 | 5.44 | +0.05 | +0.45 |
| Ex. 24 | A-3 | 0.74 | 11.0 | 0.70 | 5.70 | +0.06 | +0.57 |
| Ex. 25 | A-4 | 0.74 | 11.3 | 0.69 | 5.77 | +0.05 | +0.42 |
| Ex. 26 | A-5 | 0.74 | 11.1 | 0.71 | 5.83 | +0.05 | +0.55 |
| Ex. 27 | A-6 | 0.74 | 11.7 | 0.72 | 6.23 | +0.05 | +0.58 |
| Ex. 28 | A-8 | 0.75 | 10.0 | 0.70 | 5.25 | +0.06 | +0.56 |
| Ex. 29 | A-9 | 0.75 | 11.9 | 0.70 | 6.25 | +0.05 | +0.45 |
| Ex. 30 | A-10 | 0.77 | 12.4 | 0.70 | 6.68 | +0.06 | +0.64 |
| Ex. 31 | A-11 | 0.74 | 12.2 | 0.69 | 6.23 | +0.05 | +0.59 |
| Ex. 32 | A-12 | 0.74 | 12.3 | 0.66 | 6.01 | +0.04 | +0.41 |
| Ex. 33 | A-13 | 0.73 | 10.7 | 0.70 | 5.47 | +0.05 | +0.70 |
| Ex. 34 | A-14 | 0.71 | 10.1 | 0.68 | 4.88 | +0.04 | +0.57 |
| Ex. 35 | A-15 | 0.71 | 10.1 | 0.69 | 4.95 | +0.04 | +0.42 |
| Ex. 36 | A-16 | 0.74 | 11.5 | 0.70 | 5.96 | +0.05 | +0.44 |
| Ex. 37 | A-17 | 0.75 | 10.2 | 0.66 | 5.05 | +0.05 | +0.36 |
| Ex. 38 | A-18 | 0.74 | 10.0 | 0.65 | 4.81 | +0.04 | +0.29 |
| Ex. 39 | A-19 | 0.73 | 11.0 | 0.65 | 5.22 | +0.05 | +0.35 |
| Ex. 40 | A-20 | 0.75 | 10.1 | 0.64 | 4.85 | +0.05 | +0.31 |
| CEx. 7 | F-1 | 0.68 | 9.49 | 0.66 | 4.26 | +0.04 | −0.67 |
| CEx. 8 | F-2 | 0.69 | 9.20 | 0.66 | 4.19 | +0.04 | −0.37 |
| CEx. 9 | F-3 | 0.72 | 7.99 | 0.65 | 3.74 | +0.05 | −0.79 |
| CEx. 10 | F-4 | 0.64 | 9.10 | 0.64 | 3.73 | +0.03 | +0.02 |
| CEx. 11 | F-5 | 0.66 | 9.09 | 0.64 | 3.84 | +0.04 | +0.03 |
| CEx. 12 | F-6 | 0.68 | 9.90 | 0.67 | 4.51 | +0.04 | +0.01 |

Ex. = Example, CEx. = Comparative Example

In the technical field of dye-sensitized solar cells, it is known that the open circuit voltage is improved by increasing the concentration of 4-t-butylpyridine in an electrolytic solution. However, with an increase in the concentration of 4-t-butylpyridine, dye comes to be free from the semiconductor electrode to gradually decrease the short circuit current density. It is hence known that when the amount of 4-t-butylpyridine added is too large, the total photoelectric conversion efficiency is adversely decreased. As is clear in Table 6, it is seen that when the concentration of 4-t-butylpyridine in an electrolytic solution is increased, the open circuit voltage is improved while nearly maintaining the short circuit current density since the dye of this invention is excellent in adsorption stability, and as a result, the total photoelectric conversion efficiency is improved. On the other hand, when the dyes of Comparative Examples are used, the open circuit voltage is improved with an increase in the concentration of 4-t-butylpyridine in an electrolytic solution, but the short circuit current density is greatly decreased, and it is seen that as a result, the photoelectric conversion efficiency is decreased or only increased to a slight extent.

Example 41

<Making of Dye-Sensitized Solar Cell>

2 Grams of titanium oxide (trade name: P-25, supplied by NIPPON AEROSIL CO., LTD.), 0.2 g of acetylacetone and 0.3 g of a surfactant (trade name: Triton X-100, supplied by Sigma-Aldrich Co.) were dispersed with a paint conditioner (supplied by Red Devil Inc.) together with 6.5 g of water for 6 hours. Further, to 4.0 g of this dispersion were added 0.2 ml of concentrated nitric acid, 0.4 ml of ethanol and 1.2 g of polyethylene glycol (#20,000), to prepare a paste. The paste was applied to an FTO glass substrate so as to form a layer having a thickness of 12 82 m, and the applied paste was dried at room temperature and heated at 100° C. for 1 hour and further at 550° C. for 1 hour to give a semiconductor electrode.

Dye B-3 was dissolved in THF to prepare a dye solution having a concentration of 0.3 mM. A steroid compound El was dissolved in the dye solution such that the dye solution had a steroid compound concentration of 0.6 mM. The above-prepared semiconductor electrode was immersed and so kept in the dye solution at room temperature for 8 hours to carry out adsorption treatment, thereby to make a dye-adsorbed semiconductor electrode (work electrode). As a counter electrode, an electrode obtained by sputtering platinum on a titanium plate was used. These two electrodes were arranged such that they faced each other, and an electrolytic solution was injected between them to make a dye-sensitized solar cell. As an electrolytic solution, there was used a solution of 0.1 M of lithium iodide, 0.05 M of iodine, 0.5 M of 1,2-dimethyl-3-n-propylimidazolium iodide and 0.05 M of 4-t-butylpyridine in 3-methoxypropionitrile.

<Evaluations 1-3>

The evaluations 1 to 3 were carried out, and Tables 7 to 9 show the results.

Examples 42-64

Dye-sensitized solar cells were made in the same manner as in Example 41 except that Dye B-3 was changed to dyes shown in Table 7, and they were evaluated. Tables 7 to 9 show the results.

Comparative Examples 13-17

Dye-sensitized solar cells were made in the same manner as in Example 41 except that Dye B-3 was changed to comparative dyes F-7 to F-11, and they were evaluated. Tables 7 to 9 show the results.

[CF52]
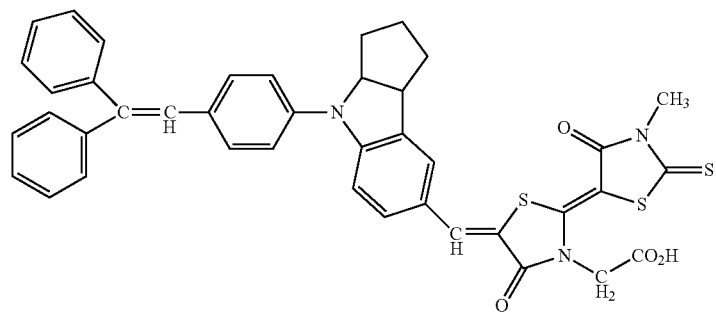
F-7
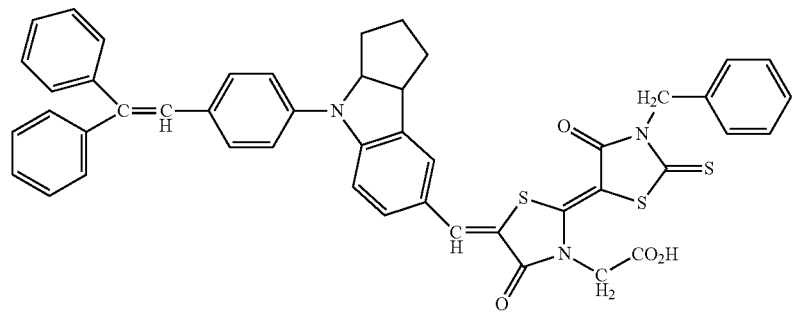
F-8
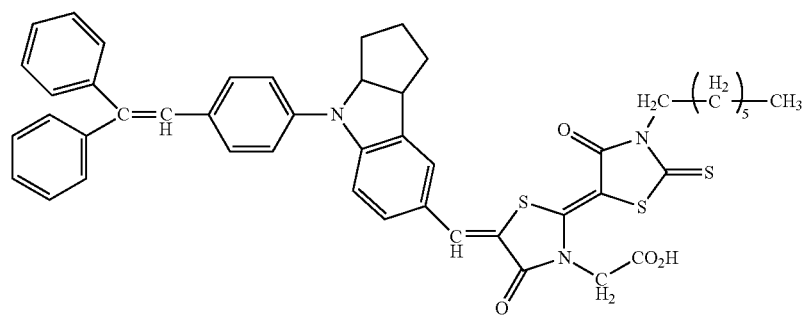
F-9
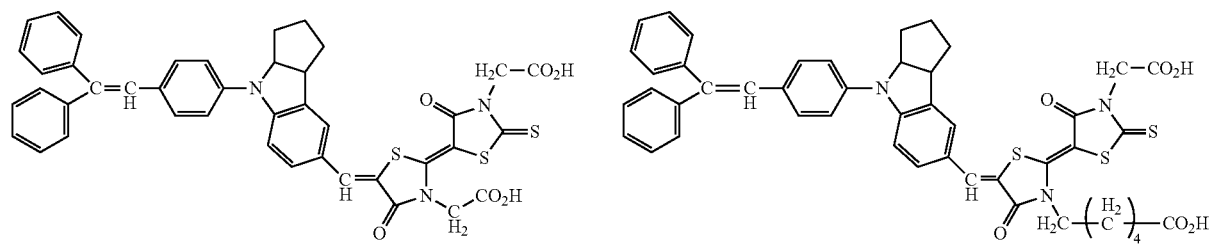
F-10    F-11
| | Dye | Open circuit voltage V | Short circuit current density mA/cm$^2$ | Fill factor | Photoelectric conversion efficiency % |
|---|---|---|---|---|---|
| Ex. 41 | B-3 | 0.69 | 13.0 | 0.69 | 6.20 |
| Ex. 42 | B-1 | 0.69 | 12.9 | 0.68 | 6.08 |
| Ex. 43 | B-2 | 0.64 | 13.0 | 0.71 | 5.91 |
| Ex. 44 | B-4 | 0.69 | 13.1 | 0.68 | 6.15 |
| Ex. 45 | B-5 | 0.69 | 12.9 | 0.68 | 6.05 |
| Ex. 46 | B-6 | 0.65 | 13.1 | 0.69 | 5.88 |
| Ex. 47 | B-7 | 0.66 | 12.7 | 0.70 | 5.87 |
| Ex. 48 | B-8 | 0.69 | 13.0 | 0.68 | 6.10 |
| Ex. 49 | B-9 | 0.70 | 13.0 | 0.69 | 6.28 |
| Ex. 50 | B-10 | 0.67 | 12.8 | 0.68 | 5.83 |
| Ex. 51 | B-11 | 0.67 | 13.2 | 0.67 | 5.93 |
| Ex. 52 | B-12 | 0.73 | 14.2 | 0.65 | 6.74 |
| Ex. 53 | B-13 | 0.66 | 13.0 | 0.69 | 5.92 |
| Ex. 54 | B-14 | 0.69 | 13.5 | 0.66 | 6.15 |
| Ex. 55 | B-15 | 0.67 | 13.1 | 0.67 | 5.88 |
| Ex. 56 | B-16 | 0.66 | 12.7 | 0.69 | 5.78 |

TABLE 7-continued

| | Dye | Open circuit voltage V | Short circuit current density mA/cm² | Fill factor | Photoelectric conversion efficiency % |
|---|---|---|---|---|---|
| Ex. 57 | B-17 | 0.73 | 14.3 | 0.65 | 6.78 |
| Ex. 58 | B-18 | 0.75 | 14.1 | 0.64 | 6.75 |
| Ex. 59 | B-19 | 0.74 | 14.2 | 0.64 | 6.75 |
| Ex. 60 | B-20 | 0.74 | 14.1 | 0.63 | 6.58 |
| Ex. 61 | B-21 | 0.73 | 14.2 | 0.66 | 6.84 |
| Ex. 62 | B-22 | 0.69 | 13.0 | 0.68 | 6.10 |
| Ex. 63 | B-23 | 0.68 | 12.9 | 0.68 | 5.96 |
| Ex. 64 | B-24 | 0.68 | 13.0 | 0.68 | 6.01 |
| CEx. 13 | F-7 | 0.67 | 13.3 | 0.66 | 5.91 |
| CEx. 14 | F-8 | 0.69 | 14.0 | 0.64 | 6.18 |
| CEx. 15 | F-9 | 0.71 | 14.1 | 0.64 | 6.41 |
| CEx. 16 | F-10 | 0.67 | 11.9 | 0.68 | 5.42 |
| CEx. 17 | F-11 | 0.63 | 8.85 | 0.71 | 3.99 |

Ex. = Example, CEx. = Comparative Example

TABLE 8

| | Dye | Open circuit voltage V | Short circuit current density mA/cm² | Fill factor | Photo-electric conversion efficiency % | Stability ratio of photo-electric conversion efficiency % |
|---|---|---|---|---|---|---|
| Ex. 41 | B-3 | 0.68 | 13.0 | 0.68 | 6.01 | 97 |
| Ex. 42 | B-1 | 0.68 | 12.8 | 0.68 | 5.90 | 97 |
| Ex. 43 | B-2 | 0.63 | 13.0 | 0.70 | 5.73 | 97 |
| Ex. 44 | B-4 | 0.68 | 12.9 | 0.68 | 5.96 | 97 |
| Ex. 45 | B-5 | 0.68 | 12.8 | 0.67 | 5.83 | 96 |
| Ex. 46 | B-6 | 0.65 | 12.6 | 0.69 | 5.65 | 96 |
| Ex. 47 | B-7 | 0.66 | 12.5 | 0.69 | 5.69 | 97 |
| Ex. 48 | B-8 | 0.68 | 12.8 | 0.68 | 5.92 | 97 |
| Ex. 49 | B-9 | 0.70 | 12.8 | 0.68 | 6.09 | 97 |
| Ex. 50 | B-10 | 0.67 | 12.6 | 0.67 | 5.66 | 97 |
| Ex. 51 | B-11 | 0.67 | 12.8 | 0.67 | 5.75 | 97 |
| Ex. 52 | B-12 | 0.72 | 14.2 | 0.64 | 6.54 | 97 |
| Ex. 53 | B-13 | 0.65 | 12.7 | 0.69 | 5.70 | 96 |
| Ex. 54 | B-14 | 0.68 | 14.1 | 0.66 | 6.34 | 97 |
| Ex. 55 | B-15 | 0.66 | 12.8 | 0.67 | 5.66 | 96 |
| Ex. 56 | B-16 | 0.66 | 12.4 | 0.68 | 5.55 | 96 |
| Ex. 57 | B-17 | 0.73 | 14.0 | 0.64 | 6.58 | 97 |
| Ex. 58 | B-18 | 0.73 | 14.0 | 0.64 | 6.55 | 97 |
| Ex. 59 | B-19 | 0.71 | 14.1 | 0.64 | 6.48 | 96 |
| Ex. 60 | B-20 | 0.71 | 14.0 | 0.64 | 6.31 | 96 |
| Ex. 61 | B-21 | 0.73 | 14.2 | 0.64 | 6.63 | 97 |
| Ex. 62 | B-22 | 0.69 | 12.8 | 0.67 | 5.92 | 97 |
| Ex. 63 | B-23 | 0.67 | 12.7 | 0.67 | 5.72 | 96 |
| Ex. 64 | B-24 | 0.67 | 12.9 | 0.67 | 5.79 | 96 |
| CEx. 13 | F-7 | 0.62 | 12.3 | 0.62 | 4.73 | 80 |
| CEx. 14 | F-8 | 0.65 | 12.9 | 0.62 | 5.19 | 84 |
| CEx. 15 | F-9 | 0.67 | 13.1 | 0.62 | 5.45 | 85 |
| CEx. 16 | F-10 | 0.66 | 11.7 | 0.67 | 5.15 | 95 |
| CEx. 17 | F-11 | 0.60 | 8.84 | 0.70 | 3.75 | 94 |

Ex. = Example, CEx. = Comparative Example

TABLE 9

| | Dye | Adsorption stability |
|---|---|---|
| Ex. 41 | B-3 | ◯ |
| Ex. 42 | B-1 | ◯ |
| Ex. 43 | B-2 | ◯ |
| Ex. 44 | B-4 | ◯ |
| Ex. 45 | B-5 | ◯ |
| Ex. 46 | B-6 | ◯ |
| Ex. 47 | B-7 | ◯ |
| Ex. 48 | B-8 | ◯ |
| Ex. 49 | B-9 | ◯ |
| Ex. 50 | B-10 | ◯ |
| Ex. 51 | B-11 | ◯ |
| Ex. 52 | B-12 | ◯ |
| Ex. 53 | B-13 | ◯ |
| Ex. 54 | B-14 | ◯ |
| Ex. 55 | B-15 | ◯ |
| Ex. 56 | B-16 | ◯ |
| Ex. 57 | B-17 | ◯ |
| Ex. 58 | B-18 | ◯ |
| Ex. 59 | B-19 | ◯ |
| Ex. 60 | B-20 | ◯ |
| Ex. 61 | B-21 | ◯ |
| Ex. 62 | B-22 | ◯ |
| Ex. 63 | B-23 | ◯ |
| Ex. 64 | B-24 | ◯ |
| CEx. 13 | F-7 | Δ |
| CEx. 14 | F-8 | Δ |
| CEx. 15 | F-9 | Δ |
| CEx. 16 | F-10 | ◯ |
| CEx. 17 | F-11 | ◯ |

Ex. = Example, CEx. = Comparative Example

Examples 65-92

Dye-sensitized solar cells were made in the same manner as in Example 41 except that Dye B-3 was changed to dyes shown in Table 10 and that the steroid compound E1 was changed to E2, and they were evaluated. Tables 10 to 12 show the results.

Comparative Examples 18-23

Dye-sensitized solar cells were made in the same manner as in Example 41 except that Dye B-3 was changed to comparative dyes F-12 to F-17 and that the steroid compound E1 was changed to E2, and they were evaluated. Tables 10 to 12 show the results.

[CF53]

F-12

-continued
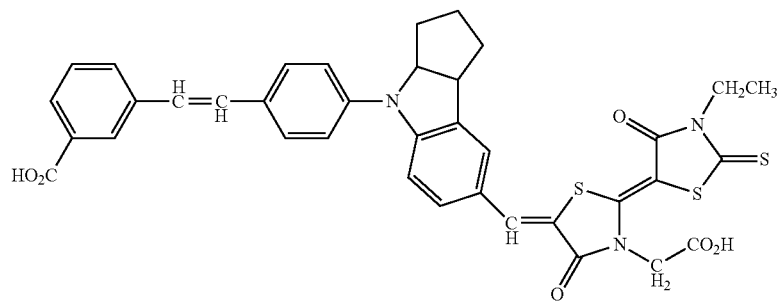
F-13
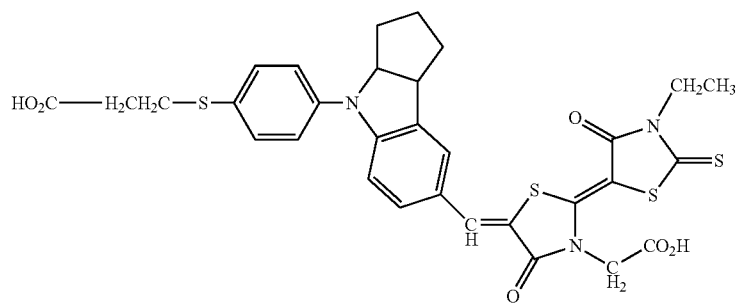
F-14
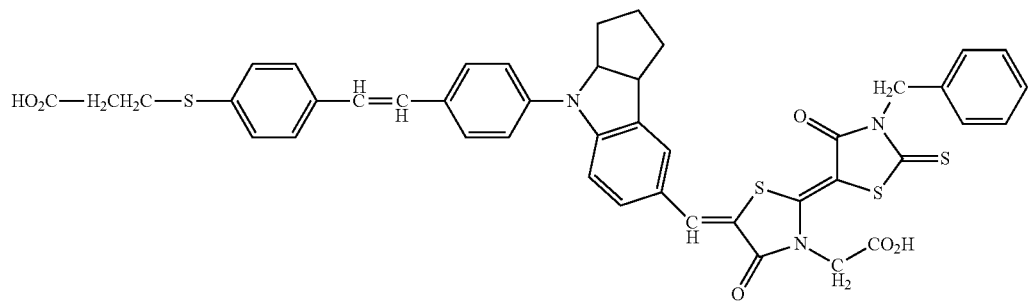
F-15
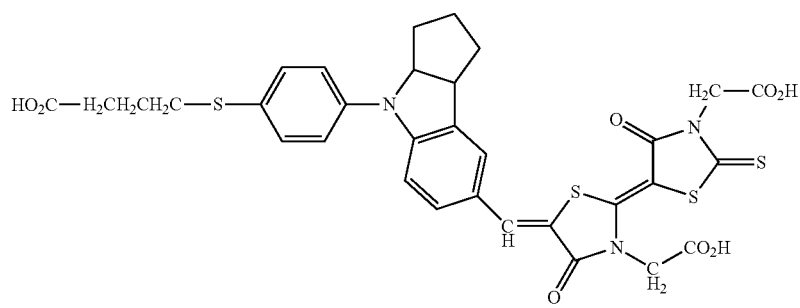
F-16
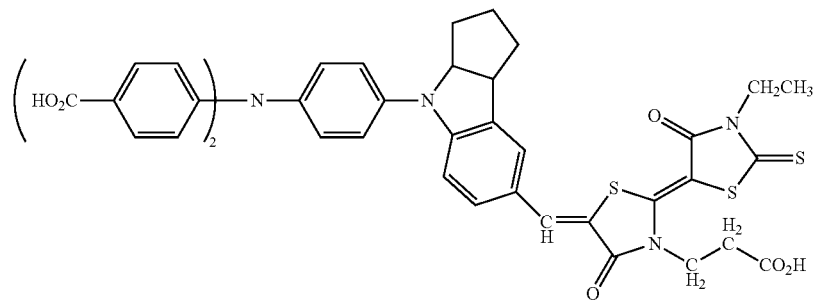
F-17

TABLE 10

| | Dye | Open circuit voltage V | Short circuit current density mA/cm² | Fill factor | Photoelectric conversion efficiency % |
|---|---|---|---|---|---|
| Ex. 65 | B-25 | 0.70 | 12.7 | 0.68 | 6.05 |
| Ex. 66 | B-26 | 0.72 | 12.8 | 0.68 | 6.27 |
| Ex. 67 | B-27 | 0.72 | 12.9 | 0.68 | 6.32 |
| Ex. 68 | B-28 | 0.71 | 13.0 | 0.68 | 6.28 |
| Ex. 69 | B-29 | 0.65 | 12.3 | 0.69 | 5.52 |
| Ex. 70 | B-30 | 0.71 | 13.1 | 0.70 | 6.51 |
| Ex. 71 | B-31 | 0.71 | 13.0 | 0.69 | 6.37 |
| Ex. 72 | B-32 | 0.71 | 13.1 | 0.69 | 6.42 |
| Ex. 73 | B-33 | 0.67 | 12.5 | 0.68 | 5.70 |
| Ex. 74 | B-34 | 0.67 | 12.6 | 0.68 | 5.74 |
| Ex. 75 | B-35 | 0.70 | 12.7 | 0.68 | 6.05 |
| Ex. 76 | B-36 | 0.71 | 12.8 | 0.69 | 6.27 |
| Ex. 77 | B-37 | 0.71 | 12.8 | 0.69 | 6.27 |
| Ex. 78 | B-38 | 0.71 | 12.9 | 0.68 | 6.23 |
| Ex. 79 | B-39 | 0.72 | 13.0 | 0.68 | 6.36 |
| Ex. 80 | B-40 | 0.72 | 13.1 | 0.68 | 6.41 |
| Ex. 81 | B-41 | 0.73 | 13.1 | 0.68 | 6.50 |
| Ex. 82 | B-42 | 0.72 | 12.7 | 0.67 | 6.13 |
| Ex. 83 | B-43 | 0.72 | 12.8 | 0.68 | 6.27 |
| Ex. 84 | B-44 | 0.70 | 12.5 | 0.67 | 5.86 |
| Ex. 85 | B-45 | 0.69 | 12.4 | 0.68 | 5.82 |
| Ex. 86 | B-46 | 0.68 | 12.3 | 0.66 | 5.52 |
| Ex. 87 | B-47 | 0.67 | 12.3 | 0.65 | 5.36 |
| Ex. 88 | B-48 | 0.65 | 12.3 | 0.66 | 5.28 |
| Ex. 89 | B-49 | 0.69 | 11.9 | 0.69 | 5.67 |
| Ex. 90 | B-50 | 0.70 | 11.8 | 0.69 | 5.70 |
| Ex. 91 | B-51 | 0.71 | 12.2 | 0.68 | 5.89 |
| Ex. 92 | B-52 | 0.69 | 12.5 | 0.67 | 5.78 |
| CEx. 18 | F-12 | 0.65 | 10.7 | 0.62 | 4.31 |
| CEx. 19 | F-13 | 0.66 | 11.2 | 0.61 | 4.51 |
| CEx. 20 | F-14 | 0.67 | 11.1 | 0.62 | 4.61 |
| CEx. 21 | F-15 | 0.68 | 11.0 | 0.61 | 4.56 |
| CEx. 22 | F-16 | 0.67 | 11.4 | 0.61 | 4.66 |
| CEx. 23 | F-17 | 0.63 | 10.2 | 0.62 | 3.98 |

Ex. = Example, CEx. = Comparative Example

TABLE 11

| | Dye | Open circuit voltage V | Short circuit current density mA/cm² | Fill factor | Photoelectric conversion efficiency % | Stability ratio of photoelectric conversion efficiency % |
|---|---|---|---|---|---|---|
| Ex. 65 | B-25 | 0.69 | 12.5 | 0.68 | 5.87 | 97 |
| Ex. 66 | B-26 | 0.71 | 12.6 | 0.68 | 6.08 | 97 |
| Ex. 67 | B-27 | 0.71 | 12.6 | 0.68 | 6.07 | 96 |
| Ex. 68 | B-28 | 0.71 | 12.6 | 0.68 | 6.09 | 97 |
| Ex. 69 | B-29 | 0.65 | 11.3 | 0.68 | 4.99 | 96 |
| Ex. 70 | B-30 | 0.71 | 12.8 | 0.69 | 6.25 | 96 |
| Ex. 71 | B-31 | 0.71 | 12.6 | 0.69 | 6.18 | 97 |
| Ex. 72 | B-32 | 0.70 | 13.1 | 0.68 | 6.23 | 97 |
| Ex. 73 | B-33 | 0.67 | 12.1 | 0.68 | 5.53 | 97 |
| Ex. 74 | B-34 | 0.66 | 12.6 | 0.67 | 5.57 | 97 |
| Ex. 75 | B-35 | 0.69 | 12.7 | 0.67 | 5.87 | 97 |
| Ex. 76 | B-36 | 0.71 | 12.6 | 0.68 | 6.08 | 97 |
| Ex. 77 | B-37 | 0.70 | 12.5 | 0.69 | 6.02 | 96 |
| Ex. 78 | B-38 | 0.70 | 12.9 | 0.67 | 6.04 | 97 |
| Ex. 79 | B-39 | 0.71 | 12.8 | 0.67 | 6.11 | 96 |
| Ex. 80 | B-40 | 0.71 | 12.9 | 0.68 | 6.22 | 97 |
| Ex. 81 | B-41 | 0.72 | 13.1 | 0.67 | 6.31 | 97 |
| Ex. 82 | B-42 | 0.72 | 12.3 | 0.67 | 5.95 | 97 |
| Ex. 83 | B-43 | 0.71 | 12.5 | 0.68 | 6.02 | 96 |
| Ex. 84 | B-44 | 0.70 | 12.0 | 0.67 | 5.63 | 96 |
| Ex. 85 | B-45 | 0.68 | 12.4 | 0.67 | 5.65 | 97 |
| Ex. 86 | B-46 | 0.68 | 11.9 | 0.66 | 5.35 | 97 |
| Ex. 87 | B-47 | 0.67 | 11.9 | 0.65 | 5.20 | 97 |
| Ex. 88 | B-48 | 0.65 | 11.8 | 0.66 | 5.07 | 96 |
| Ex. 89 | B-49 | 0.68 | 11.9 | 0.68 | 5.50 | 97 |
| Ex. 90 | B-50 | 0.69 | 11.8 | 0.68 | 5.53 | 97 |
| Ex. 91 | B-51 | 0.70 | 12.0 | 0.68 | 5.71 | 97 |
| Ex. 92 | B-52 | 0.68 | 12.3 | 0.67 | 5.61 | 97 |
| CEx. 18 | F-12 | 0.64 | 8.91 | 0.57 | 3.25 | 75 |
| CEx. 19 | F-13 | 0.65 | 8.41 | 0.60 | 3.28 | 73 |
| CEx. 20 | F-14 | 0.67 | 9.31 | 0.59 | 3.68 | 80 |
| CEx. 21 | F-15 | 0.68 | 8.70 | 0.60 | 3.55 | 78 |
| CEx. 22 | F-16 | 0.67 | 9.70 | 0.60 | 3.90 | 84 |
| CEx. 23 | F-17 | 0.61 | 8.80 | 0.60 | 3.22 | 81 |

Ex. = Example, CEx. = Comparative Example

TABLE 12

| | Dye | Adsorption stability |
|---|---|---|
| Ex. 65 | B-25 | ○ |
| Ex. 66 | B-26 | ○ |
| Ex. 67 | B-27 | ○ |
| Ex. 68 | B-28 | ○ |
| Ex. 69 | B-29 | ○ |
| Ex. 70 | B-30 | ○ |
| Ex. 71 | B-31 | ○ |
| Ex. 72 | B-32 | ○ |
| Ex. 73 | B-33 | ○ |
| Ex. 74 | B-34 | ○ |
| Ex. 75 | B-35 | ○ |
| Ex. 76 | B-36 | ○ |
| Ex. 77 | B-37 | ○ |
| Ex. 78 | B-38 | ○ |
| Ex. 79 | B-39 | ○ |
| Ex. 80 | B-40 | ○ |
| Ex. 81 | B-41 | ○ |
| Ex. 82 | B-42 | ○ |
| Ex. 83 | B-43 | ○ |
| Ex. 84 | B-44 | ○ |
| Ex. 85 | B-45 | ○ |
| Ex. 86 | B-46 | ○ |
| Ex. 87 | B-47 | ○ |
| Ex. 88 | B-48 | ○ |
| Ex. 89 | B-49 | ○ |
| Ex. 90 | B-50 | ○ |
| Ex. 91 | B-51 | ○ |
| Ex. 92 | B-52 | ○ |
| CEx. 18 | F-12 | ○ |
| CEx. 19 | F-13 | ○ |
| CEx. 20 | F-14 | ○ |
| CEx. 21 | F-15 | ○ |
| CEx. 22 | F-16 | ○ |
| CEx. 23 | F-17 | ○ |

Ex. = Example, CEx. = Comparative Example

In Tables 7 and 10, it is seen that the dyes of this invention each having the first acidic group and the second acidic group arranged in predetermined sites of the molecule thereof exhibit excellent photoelectric conversion efficiency. Of the dyes of Comparative Examples, the dyes having the first acidic group in the electron acceptor unit and having no second acidic group (F-7, F-8 and F-9) exhibit excellent photoelectric conversion efficiency. On the other hand, it is seen that the dye having the first acidic group in the electron acceptor unit and having an acidic group possessing a pKa of less than 6 bonded through an alkylene group having 1 carbon atom (F-10), the dye having the first acidic group and the second acidic group arranged in positions reversed to those of the dye B-3 (F-11), the dyes each having the first acidic group in the electron acceptor unit and the acidic group bonded directly to the sp² carbon atom constituting the π electron conjugated system of the electron donor unit (F-12 and F-13), the dyes each having the first acidic group in the electron acceptor unit and having the acidic group possessing a pKa of less than 6 bonded through an alkylene group having 2 or 3 carbon atoms in the electron donor unit (F-14 and F-15), the dye having the first acidic group and an acidic group possessing a pKa of less than 6 bonded through an alkylene group having 1 carbon atom in the electron acceptor unit and having the acidic group possessing a pKa of less than 6 bonded through an alkylene group having 2-3 carbon atoms in the electron donor unit (F-16), and the dye having the first acidic group in the electron acceptor unit, having an aromatic amino group as a substituent on the electron donor unit and having the acidic group possessing a pKa of less than 6 bonded directly to the sp² carbon atom of the aromatic amino group (F-17) have low photoelectric conversion efficiency.

In Tables 8 and 11, the dyes of this invention have higher stability ratios of photoelectric conversion efficiency after storage in a 65° C. environment for 14 days than the dyes of Comparative Examples and hence have excellent durability.

In Tables 9 and 12, it is seen that the dyes of this invention are excellent in the stability of adsorption to a semiconductor electrode. Of the dyes of Comparative Examples, it is seen that the dyes F-7, F-8 and F-9 are poor in the stability of adsorption to a semiconductor electrode as compared with the dyes of this invention. The dyes F-10 to F-17 are excellent in the stability of adsorption to a semiconductor electrode.

To summarize these results, it is seen that the dyes of this invention have all of high photoelectric conversion efficiency, excellent durability and good adsorption stability.

Example 93

A dye-sensitized solar cell was made in the same manner as in Example 41 except that the concentration of 4-t-butylpyridine in the electrolytic solution was changed to 0.5 M, and evaluated for photoelectric conversion efficiency. Table 13 shows the results. As compared with Example 41, the open circuit voltage changed by +0.06 V, the short circuit current density changed by −0.1 mA/cm², and the fill factor changed by +0.03, and as a result, the photoelectric conversion efficiency was improved by +0.80%.

Examples 94-144

Dye-sensitized solar cells were made in the same manner as in Examples 42 to 92 except that the concentration of 4-t-butylpyridine in an electrolytic solution was changed to 0.5 M, and they were evaluated for photoelectric conversion efficiency. Tables 13 and 14 show the results. Tables 13 and 14 also show differences in open circuit voltage and photoelectric conversion efficiency from Examples 42 to 92.

Comparative Examples 24-34

Dye-sensitized solar cells were made in the same manner as in Comparative Examples 13 to 23 except that the concentration of 4-t-butylpyridine in an electrolytic solution was changed to 0.5 M, and they were evaluated for photoelectric conversion efficiency. Tables 13 and 14 show the results. Tables 13 and 14 also show differences in open circuit voltage and photoelectric conversion efficiency from Comparative Examples 13 to 23.

TABLE 13

| | Dye | Open circuit voltage V | Short circuit current density mA/cm² | Fill factor | Photoelectric conversion efficiency % | Difference in open circuit voltage V | Difference in photoelectric conversion efficiency % |
|---|---|---|---|---|---|---|---|
| Ex. 93 | B-3 | 0.75 | 12.9 | 0.72 | 7.00 | +0.06 | +0.80 |
| Ex. 94 | B-1 | 0.75 | 12.8 | 0.70 | 6.72 | +0.06 | +0.64 |
| Ex. 95 | B-2 | 0.69 | 12.9 | 0.72 | 6.41 | +0.05 | +0.50 |
| Ex. 96 | B-4 | 0.74 | 13.0 | 0.70 | 6.73 | +0.05 | +0.58 |
| Ex. 97 | B-5 | 0.74 | 12.9 | 0.69 | 6.59 | +0.05 | +0.54 |
| Ex. 98 | B-6 | 0.71 | 13.0 | 0.71 | 6.55 | +0.06 | +0.67 |
| Ex. 99 | B-7 | 0.72 | 12.6 | 0.72 | 6.53 | +0.06 | +0.66 |
| Ex. 100 | B-8 | 0.75 | 12.9 | 0.70 | 6.77 | +0.06 | +0.67 |
| Ex. 101 | B-9 | 0.75 | 13.0 | 0.70 | 6.82 | +0.05 | +0.54 |
| Ex. 102 | B-10 | 0.73 | 12.8 | 0.70 | 6.54 | +0.06 | +0.71 |
| Ex. 103 | B-11 | 0.72 | 13.1 | 0.69 | 6.51 | +0.05 | +0.58 |
| Ex. 104 | B-12 | 0.77 | 14.1 | 0.66 | 7.17 | +0.04 | +0.43 |
| Ex. 105 | B-13 | 0.71 | 12.9 | 0.70 | 6.41 | +0.05 | +0.49 |
| Ex. 106 | B-14 | 0.75 | 13.3 | 0.68 | 6.78 | +0.06 | +0.63 |
| Ex. 107 | B-15 | 0.72 | 13.0 | 0.69 | 6.46 | +0.05 | +0.58 |
| Ex. 108 | B-16 | 0.71 | 12.6 | 0.70 | 6.26 | +0.05 | +0.48 |
| Ex. 109 | B-17 | 0.78 | 14.1 | 0.66 | 7.26 | +0.05 | +0.48 |
| Ex. 110 | B-18 | 0.79 | 14.0 | 0.65 | 7.19 | +0.04 | +0.44 |
| Ex. 111 | B-19 | 0.79 | 14.1 | 0.65 | 7.24 | +0.05 | +0.49 |
| Ex. 112 | B-20 | 0.78 | 14.0 | 0.64 | 6.99 | +0.04 | +0.41 |
| Ex. 113 | B-21 | 0.78 | 14.0 | 0.67 | 7.32 | +0.05 | +0.48 |
| Ex. 114 | B-22 | 0.74 | 12.9 | 0.70 | 6.68 | +0.05 | +0.58 |
| Ex. 115 | B-23 | 0.73 | 12.8 | 0.70 | 6.54 | +0.05 | +0.58 |
| Ex. 116 | B-24 | 0.72 | 13.0 | 0.70 | 6.55 | +0.04 | +0.54 |
| CEx. 24 | F-7 | 0.70 | 10.1 | 0.66 | 4.67 | +0.03 | −1.24 |
| CEx. 25 | F-8 | 0.73 | 10.0 | 0.66 | 4.82 | +0.04 | −1.36 |
| CEx. 26 | F-9 | 0.76 | 10.3 | 0.65 | 5.09 | +0.05 | −1.32 |
| CEx. 27 | F-10 | 0.70 | 10.0 | 0.69 | 4.83 | +0.03 | −0.59 |
| CEx. 28 | F-11 | 0.68 | 8.00 | 0.71 | 3.86 | +0.05 | −0.13 |

Ex. = Example, CEx. = Comparative Example

TABLE 14

| | Dye | Open circuit voltage V | Short circuit current density mA/cm² | Fill factor | Photoelectric conversion efficiency % | Difference in open circuit voltage V | Difference in photoelectric conversion efficiency % |
|---|---|---|---|---|---|---|---|
| Ex. 117 | B-25 | 0.74 | 12.7 | 0.70 | 6.58 | +0.04 | +0.53 |
| Ex. 118 | B-26 | 0.77 | 12.7 | 0.70 | 6.85 | +0.05 | +0.58 |
| Ex. 119 | B-27 | 0.77 | 12.8 | 0.70 | 6.90 | +0.05 | +0.58 |
| Ex. 120 | B-28 | 0.76 | 12.9 | 0.69 | 6.76 | +0.05 | +0.48 |
| Ex. 121 | B-29 | 0.71 | 12.2 | 0.70 | 6.06 | +0.06 | +0.54 |
| Ex. 122 | B-30 | 0.76 | 13.0 | 0.71 | 7.01 | +0.05 | +0.50 |
| Ex. 123 | B-31 | 0.76 | 12.9 | 0.70 | 6.86 | +0.05 | +0.49 |
| Ex. 124 | B-32 | 0.75 | 13.0 | 0.70 | 6.83 | +0.04 | +0.41 |
| Ex. 125 | B-33 | 0.72 | 12.4 | 0.69 | 6.16 | +0.05 | +0.46 |
| Ex. 126 | B-34 | 0.72 | 12.5 | 0.69 | 6.21 | +0.05 | +0.47 |
| Ex. 127 | B-35 | 0.75 | 12.6 | 0.69 | 6.52 | +0.05 | +0.47 |
| Ex. 128 | B-36 | 0.76 | 12.7 | 0.71 | 6.85 | +0.05 | +0.58 |
| Ex. 129 | B-37 | 0.75 | 12.7 | 0.70 | 6.67 | +0.04 | +0.40 |
| Ex. 130 | B-38 | 0.76 | 12.8 | 0.69 | 6.71 | +0.05 | +0.48 |
| Ex. 131 | B-39 | 0.77 | 12.9 | 0.69 | 6.85 | +0.05 | +0.49 |
| Ex. 132 | B-40 | 0.77 | 13.0 | 0.69 | 6.91 | +0.05 | +0.50 |
| Ex. 133 | B-41 | 0.78 | 13.0 | 0.69 | 7.00 | +0.05 | +0.50 |
| Ex. 134 | B-42 | 0.77 | 12.6 | 0.68 | 6.60 | +0.05 | +0.47 |
| Ex. 135 | B-43 | 0.77 | 12.7 | 0.69 | 6.75 | +0.05 | +0.48 |
| Ex. 136 | B-44 | 0.75 | 12.4 | 0.68 | 6.32 | +0.05 | +0.46 |
| Ex. 137 | B-45 | 0.74 | 12.3 | 0.70 | 6.37 | +0.05 | +0.55 |
| Ex. 138 | B-46 | 0.73 | 12.2 | 0.67 | 5.97 | +0.05 | +0.45 |
| Ex. 139 | B-47 | 0.72 | 12.2 | 0.67 | 5.89 | +0.05 | +0.53 |
| Ex. 140 | B-48 | 0.70 | 12.2 | 0.67 | 5.72 | +0.05 | +0.44 |
| Ex. 141 | B-49 | 0.74 | 11.8 | 0.70 | 6.11 | +0.05 | +0.44 |
| Ex. 142 | B-50 | 0.75 | 11.8 | 0.70 | 6.20 | +0.05 | +0.50 |
| Ex. 143 | B-51 | 0.76 | 12.1 | 0.69 | 6.35 | +0.05 | +0.46 |
| Ex. 144 | B-52 | 0.74 | 12.4 | 0.68 | 6.24 | +0.05 | +0.46 |
| CEx. 29 | F-12 | 0.68 | 9.50 | 0.63 | 4.07 | +0.03 | −0.24 |
| CEx. 30 | F-13 | 0.70 | 9.91 | 0.63 | 4.37 | +0.04 | −0.14 |

TABLE 14-continued

| Dye | Open circuit voltage V | Short circuit current density mA/cm² | Fill factor | Photo-electric conversion efficiency % | Difference in open circuit voltage V | Difference in photo-electric conversion efficiency % |
|---|---|---|---|---|---|---|
| CEx. 31 F-14 | 0.71 | 10.0 | 0.63 | 4.47 | +0.04 | −0.14 |
| CEx. 32 F-15 | 0.72 | 10.0 | 0.62 | 4.46 | +0.04 | −0.10 |
| CEx. 33 F-16 | 0.70 | 10.2 | 0.62 | 4.43 | +0.03 | −0.23 |
| CEx. 34 F-17 | 0.65 | 9.21 | 0.63 | 3.77 | +0.02 | −0.21 |

Ex. = Example, CEx. = Comparative Example

As is clear in Tables 13 and 14, it is seen that when the concentration of 4-t-butylpyridine in an electrolytic solution is increased, the open circuit voltage is improved while nearly maintaining the short circuit current density since the dye of this invention is excellent in the stability of adsorption to a semiconductor electrode, and as a result, the total photoelectric conversion efficiency is improved. On the other hand, when the dyes of Comparative Examples are used, the open circuit voltage is improved with an increase in the concentration of 4-t-butylpyridine in an electrolytic solution, but the short circuit current density is greatly decreased, and it is seen that as a result, the photoelectric conversion efficiency is decreased.

Example 145

<Making of Dye-Sensitized Solar Cell>

2 Grams of titanium oxide (trade name: P-25, supplied by NIPPON AEROSIL CO., LTD.), 0.2 g of acetylacetone and 0.3 g of a surfactant (trade name: Triton X-100, supplied by Sigma-Aldrich Co.) were dispersed with paint conditioner (supplied by Red Devil Inc.) together with 6.5 g of water for 6 hours. Further, to 4.0 g of this dispersion were added 0.2 ml of concentrated nitric acid, 0.4 ml of ethanol and 1.2 g of polyethylene glycol (#20,000), to prepare a paste. The paste was applied to an FTO glass substrate so as to form a layer having a thickness of 10 μm, and the applied paste was dried at room temperature and heated at 100° C. for 1 hour and further at 550° C. for 1 hour to give a semiconductor electrode.

Dye C-8 was dissolved in tetrahydrofuran to prepare a dye solution having a concentration of 0.3 mM. The steroid compound El was dissolved in the dye solution such that the dye solution had a steroid compound concentration of 0.6 mM. Then, the above-prepared semiconductor electrode was immersed and so kept in the dye solution at room temperature for 5 hours to carry out adsorption treatment, thereby to make a dye-adsorbed semiconductor electrode (work electrode). As a counter electrode, an electrode obtained by sputtering platinum on a titanium plate was used. These two electrodes were arranged such that they faced each other, and an electrolytic solution was injected between them to make a dye-sensitized solar cell. As an electrolytic solution, there was used a solution of 0.1 M of lithium iodide, 0.05 M of iodine, 0.5 M of 1,2-dimethyl-3-n-propylimidazolium iodide and 0.05 M of 4-t-butylpyridine in 3-methoxypropionitrile.

<Evaluations 1-3>

The evaluations 1 to 3 were carried out, and Tables 15 to 17 show the results.

Examples 146-164

Dye-sensitized solar cells were made in the same manner as in Example 145 except that Dye C-8 was changed to dyes shown in Table 15, and they were evaluated. Tables 15 to 17 show the results.

Comparative Examples 35-39

Dye-sensitized solar cells were made in the same manner as in Example 145 except that Dye C-8 was changed to comparative dyes F-18 to F-22, and they were evaluated. Tables 15 to 17 show the results.

[CF54]

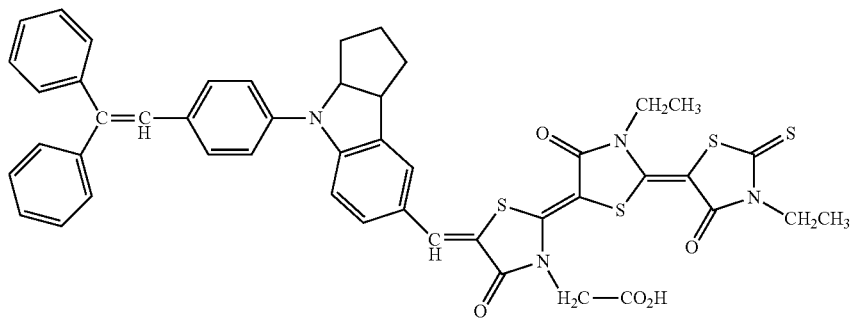

F-18

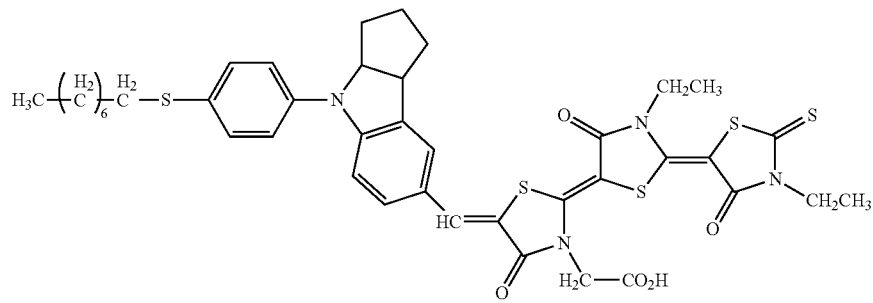

F-19

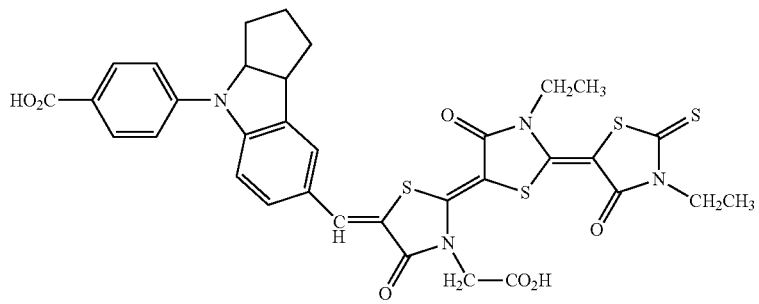

F-20

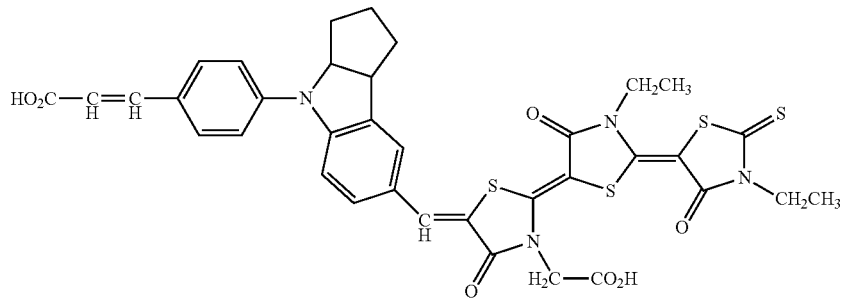

F-21

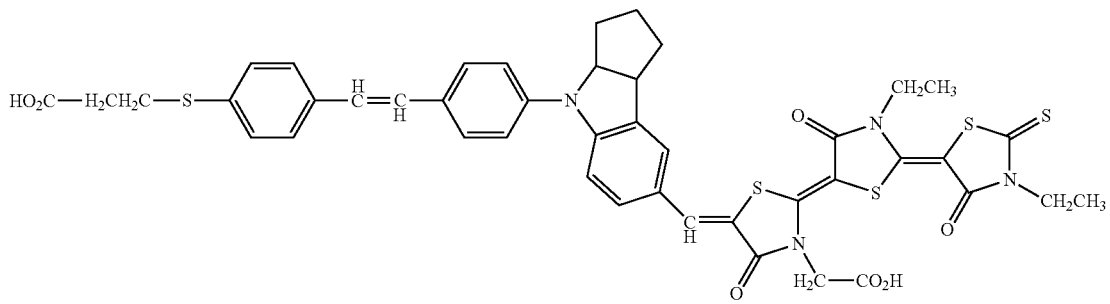

F-22

TABLE 15

| | Dye | Open circuit voltage V | Short circuit current density mA/cm² | Fill factor | Photoelectric conversion efficiency % |
|---|---|---|---|---|---|
| Ex. 145 | C-8 | 0.67 | 14.6 | 0.66 | 6.46 |
| Ex. 146 | C-1 | 0.67 | 12.9 | 0.66 | 5.70 |
| Ex. 147 | C-2 | 0.67 | 12.5 | 0.71 | 5.95 |
| Ex. 148 | C-3 | 0.68 | 12.1 | 0.68 | 5.60 |
| Ex. 149 | C-4 | 0.69 | 12.4 | 0.68 | 5.82 |
| Ex. 150 | C-5 | 0.69 | 12.1 | 0.69 | 5.76 |
| Ex. 151 | C-6 | 0.69 | 12.3 | 0.70 | 5.94 |
| Ex. 152 | C-7 | 0.68 | 14.0 | 0.68 | 6.47 |
| Ex. 153 | C-9 | 0.66 | 12.0 | 0.69 | 5.46 |
| Ex. 154 | C-10 | 0.65 | 13.5 | 0.68 | 5.97 |
| Ex. 155 | C-11 | 0.69 | 14.2 | 0.67 | 6.56 |
| Ex. 156 | C-12 | 0.68 | 12.8 | 0.65 | 5.66 |
| Ex. 157 | C-13 | 0.68 | 12.7 | 0.65 | 5.61 |
| Ex. 158 | C-14 | 0.66 | 11.2 | 0.63 | 4.66 |
| Ex. 159 | C-15 | 0.67 | 10.1 | 0.67 | 4.53 |
| Ex. 160 | C-16 | 0.69 | 10.6 | 0.69 | 5.05 |
| Ex. 161 | C-17 | 0.70 | 10.3 | 0.65 | 4.69 |
| Ex. 162 | C-18 | 0.70 | 10.1 | 0.64 | 4.52 |
| Ex. 163 | C-19 | 0.68 | 11.2 | 0.64 | 4.87 |
| Ex. 164 | C-20 | 0.70 | 10.3 | 0.66 | 4.76 |
| CEx. 35 | F-18 | 0.62 | 12.3 | 0.66 | 5.03 |
| CEx. 36 | F-19 | 0.65 | 12.5 | 0.67 | 5.44 |
| CEx. 37 | F-20 | 0.61 | 10.1 | 0.67 | 4.13 |
| CEx. 38 | F-21 | 0.62 | 10.4 | 0.64 | 4.13 |
| CEx. 39 | F-22 | 0.62 | 10.5 | 0.64 | 4.17 |

Ex. = Example, CEx. = Comparative Example

TABLE 16

| | Dye | Open circuit voltage V | Short circuit current density mA/cm² | Fill factor | Photoelectric conversion efficiency % | Stability ratio of photoelectric conversion efficiency % |
|---|---|---|---|---|---|---|
| Ex. 145 | C-8 | 0.67 | 14.4 | 0.65 | 6.27 | 97 |
| Ex. 146 | C-1 | 0.67 | 12.1 | 0.68 | 5.53 | 97 |
| Ex. 147 | C-2 | 0.66 | 12.5 | 0.70 | 5.77 | 97 |
| Ex. 148 | C-3 | 0.67 | 11.9 | 0.68 | 5.43 | 97 |
| Ex. 149 | C-4 | 0.67 | 12.5 | 0.67 | 5.59 | 96 |
| Ex. 150 | C-5 | 0.68 | 11.8 | 0.69 | 5.53 | 96 |
| Ex. 151 | C-6 | 0.68 | 12.3 | 0.69 | 5.76 | 97 |

TABLE 16-continued

| | Dye | Open circuit voltage V | Short circuit current density mA/cm² | Fill factor | Photo-electric conversion efficiency % | Stability ratio of photo-electric conversion efficiency % |
|---|---|---|---|---|---|---|
| Ex. 152 | C-7 | 0.67 | 13.8 | 0.68 | 6.28 | 97 |
| Ex. 153 | C-9 | 0.65 | 12.0 | 0.68 | 5.30 | 97 |
| Ex. 154 | C-10 | 0.64 | 13.5 | 0.67 | 5.79 | 97 |
| Ex. 155 | C-11 | 0.68 | 14.0 | 0.67 | 5.36 | 97 |
| Ex. 156 | C-12 | 0.67 | 12.8 | 0.64 | 5.49 | 97 |
| Ex. 157 | C-13 | 0.66 | 12.6 | 0.65 | 5.39 | 96 |
| Ex. 158 | C-14 | 0.65 | 11.2 | 0.62 | 4.52 | 97 |
| Ex. 159 | C-15 | 0.66 | 9.80 | 0.67 | 4.35 | 96 |
| Ex. 160 | C-16 | 0.67 | 10.6 | 0.68 | 4.85 | 96 |
| Ex. 161 | C-17 | 0.68 | 10.5 | 0.64 | 4.55 | 97 |
| Ex. 162 | C-18 | 0.68 | 10.8 | 0.64 | 4.72 | 97 |
| Ex. 163 | C-19 | 0.66 | 11.1 | 0.64 | 4.68 | 96 |
| Ex. 164 | C-20 | 0.68 | 10.7 | 0.63 | 4.57 | 96 |
| CEx. 35 | F-18 | 0.61 | 8.49 | 0.66 | 3.42 | 68 |
| CEx. 36 | F-19 | 0.64 | 7.98 | 0.66 | 3.37 | 62 |
| CEx. 37 | F-20 | 0.61 | 7.59 | 0.67 | 3.10 | 75 |
| CEx. 38 | F-21 | 0.61 | 8.25 | 0.64 | 3.22 | 78 |
| CEx. 39 | F-22 | 0.61 | 8.69 | 0.63 | 3.34 | 80 |

Ex. = Example, CEx. = Comparative Example

TABLE 17

| | Dye | Adsorption stability |
|---|---|---|
| Example 145 | C-8 | ○ |
| Example 146 | C-1 | ○ |
| Example 147 | C-2 | ○ |
| Example 148 | C-3 | ○ |
| Example 149 | C-4 | ○ |
| Example 150 | C-5 | ○ |
| Example 151 | C-6 | ○ |
| Example 152 | C-7 | ○ |
| Example 153 | C-9 | ○ |
| Example 154 | C-10 | ○ |
| Example 155 | C-11 | ○ |
| Example 156 | C-12 | ○ |
| Example 157 | C-13 | ○ |
| Example 158 | C-14 | ○ |
| Example 159 | C-15 | ○ |
| Example 160 | C-16 | ○ |
| Example 161 | C-17 | ○ |
| Example 162 | C-18 | ○ |
| Example 163 | C-19 | ○ |
| Example 164 | C-20 | ○ |
| CEx. 35 | F-18 | Δ |
| CEx. 36 | F-19 | Δ |
| CEx. 37 | F-20 | ○ |
| CEx. 38 | F-21 | ○ |
| CEx. 39 | F-22 | ○ |

CEx. = Comparative Example

In Table 15, it is seen that the dyes of this invention having the first acid group and the second acidic group in the predetermined sites of the molecule thereof exhibit excellent photoelectric conversion efficiency. Further, it is seen that of the dyes of Comparative Examples, the dyes having the first acidic group in the electron acceptor unit and having no second acidic group (F-18 and F-19) exhibit excellent photoelectric conversion efficiency. On the other hand, it is seen that the dyes having the first acidic group in the electron acceptor unit and an acid group bonded directly to the sp² carbon atom constituting the π electron conjugated system of the electron donor unit (F-20 and F-21) and the dye having the first acidic group in the electron acceptor unit and having an acid group possessing a pKa of less than 6 bonded through an alkylene group having 2 carbon atoms in the electron donor unit (F-22) have low photoelectric conversion efficiency.

In Table 16, it is seen that the dyes of this invention have higher stability ratios of photoelectric conversion efficiency after storage in a 65° C. environment for 14 days than the dyes of Comparative Examples and have excellent durability.

In Table 17, it is seen that the dyes of this invention are also excellent in the stability of adsorption to a semiconductor electrode. Further, it is seen that of the dyes of Comparative Examples, the dyes F-18 and F-19 are poor in the stability of adsorption to a semiconductor electrode as compared with the dyes of this invention. The dyes F-20, F-21 and F-22 are excellent in adsorption stability.

To summarize these results, it is seen that the dyes of this invention have all of high photoelectric conversion efficiency, excellent durability and good adsorption stability.

A dye-sensitized solar cell was made in the same manner as in Example 145 except that the concentration of 4-t-butylpyridine in the electrolytic solution was changed to 0.5 M, and evaluated for photoelectric conversion efficiency. Table 18 shows the results. As compared with Example 145, the open circuit voltage changed by +0.05 V, the short circuit current density changed by −0.1 mA/cm², and the fill factor changed by +0.02, and as a result, the photoelectric conversion efficiency was improved by +0.64%.

Examples 166-184

Dye-sensitized solar cells were made in the same manner as in Examples 146 to 164 except that the concentration of 4-t-butylpyridine in an electrolytic solution was changed to 0.5 M, and they were evaluated for photoelectric conversion efficiency. Table 18 shows the results. Table 18 also shows differences in open circuit voltage and photoelectric conversion efficiency from Examples 146 to 164.

Comparative Examples 40-44

Dye-sensitized solar cells were made in the same manner as in Comparative Examples 35 to 39 except that the concentration of 4-t-butylpyridine in an electrolytic solution was changed to 0.5 M, and they were evaluated for photoelectric conversion efficiency. Table 18 shows the results. Table 18 also shows differences in open circuit voltage and photoelectric conversion efficiency from Comparative Examples 35 to 39.

TABLE 18

| | Dye | Open circuit voltage V | Short circuit current density mA/cm² | Fill factor | Photo-electric conversion efficiency % | Difference in open circuit voltage V | Difference in photo-electric conversion efficiency % |
|---|---|---|---|---|---|---|---|
| Ex. 165 | C-8 | 0.72 | 14.5 | 0.68 | 7.10 | +0.05 | +0.64 |
| Ex. 166 | C-1 | 0.73 | 12.8 | 0.70 | 6.54 | +0.06 | +0.84 |
| Ex. 167 | C-2 | 0.72 | 12.4 | 0.72 | 6.42 | +0.05 | +0.47 |
| Ex. 168 | C-3 | 0.74 | 12.0 | 0.70 | 6.22 | +0.06 | +0.62 |
| Ex. 169 | C-4 | 0.74 | 12.3 | 0.69 | 6.28 | +0.05 | +0.46 |
| Ex. 170 | C-5 | 0.74 | 12.1 | 0.71 | 6.36 | +0.05 | +0.84 |
| Ex. 171 | C-6 | 0.74 | 12.2 | 0.72 | 6.50 | +0.05 | +0.56 |
| Ex. 172 | C-7 | 0.74 | 13.9 | 0.70 | 7.20 | +0.06 | +0.73 |
| Ex. 173 | C-9 | 0.71 | 11.9 | 0.70 | 5.91 | +0.05 | +0.45 |
| Ex. 174 | C-10 | 0.71 | 13.4 | 0.70 | 6.66 | +0.06 | +0.69 |
| Ex. 175 | C-11 | 0.74 | 14.0 | 0.69 | 7.15 | +0.05 | +0.59 |
| Ex. 176 | C-12 | 0.72 | 12.5 | 0.66 | 5.94 | +0.04 | +0.28 |
| Ex. 177 | C-13 | 0.73 | 12.5 | 0.66 | 6.02 | +0.05 | +0.41 |
| Ex. 178 | C-14 | 0.70 | 11.1 | 0.66 | 5.13 | +0.04 | +0.47 |

TABLE 18-continued

| | Dye | Open circuit voltage V | Short circuit current density mA/cm² | Fill factor | Photo-electric conversion efficiency % | Difference in open circuit voltage V | Difference in photo-electric conversion efficiency % |
|---|---|---|---|---|---|---|---|
| Ex. 179 | C-15 | 0.71 | 10.0 | 0.69 | 4.90 | +0.04 | +0.37 |
| Ex. 180 | C-16 | 0.74 | 10.5 | 0.70 | 5.44 | +0.05 | +0.39 |
| Ex. 181 | C-17 | 0.75 | 10.2 | 0.66 | 5.05 | +0.05 | +0.36 |
| Ex. 182 | C-18 | 0.74 | 10.0 | 0.65 | 4.81 | +0.04 | +0.29 |
| Ex. 183 | C-19 | 0.73 | 11.1 | 0.65 | 5.22 | +0.05 | +0.35 |
| Ex. 184 | C-20 | 0.75 | 10.1 | 0.66 | 5.00 | +0.05 | +0.24 |
| CEx. 40 | F-18 | 0.66 | 9.80 | 0.66 | 4.27 | +0.04 | −0.76 |
| CEx. 41 | F-19 | 0.69 | 9.90 | 0.66 | 4.51 | +0.04 | −0.93 |
| CEx. 42 | F-20 | 0.65 | 9.89 | 0.65 | 4.18 | +0.05 | +0.05 |
| CEx. 43 | F-21 | 0.67 | 10.0 | 0.63 | 4.22 | +0.03 | +0.09 |
| CEx. 44 | F-22 | 0.66 | 10.1 | 0.64 | 4.27 | +0.04 | +0.10 |

Ex. = Example, CEx. = Comparative Example

As is clear in Table 18, it is seen that when the concentration of 4-t-butylpyridine in an electrolytic solution is increased, the open circuit voltage is improved while nearly maintaining the short circuit current density since the dyes of this invention are excellent in adsorption stability, and as a result, the total photoelectric conversion efficiency is improved. On the other hand, when the dyes of Comparative Examples are used, the open circuit voltage is improved with an increase in the concentration of 4-t-butylpyridine in an electrolytic solution, but the short circuit current density is greatly decreased, and it is seen that as a result, the photoelectric conversion efficiency is decreased or only increased to a slight extent.

Example 185

<Making of Dye-Sensitized Solar Cell>

2 Grams of titanium oxide (trade name: P-25, supplied by NIPPON AEROSIL CO., LTD.), 0.2 g of acetylacetone and 0.3 g of a surfactant (trade name: Triton X-100, supplied by Sigma-Aldrich Co.) were dispersed with a paint conditioner (supplied by Red Devil Inc.) together with 6.5 g of water for 6 hours. Further, to 4.0 g of this dispersion were added 0.2 ml of concentrated nitric acid, 0.4 ml of ethanol and 1.2 g of polyethylene glycol (#20,000), to prepare a paste. The paste was applied to an FTO glass substrate so as to form a layer having a thickness of 10 μm and the applied paste was dried at room temperature and heated at 100° C. for 1 hour and further at 550° C. for 1 hour to give a semiconductor electrode.

Dye D-7 was dissolved in tetrahydrofuran to prepare a dye solution having a concentration of 0.3 mM. Then, the above-prepared semiconductor electrode was immersed and so kept in the dye solution at room temperature for 3 hours to carry out adsorption treatment, thereby to make a dye-adsorbed semiconductor electrode (work electrode). As a counter electrode, an electrode obtained by sputtering platinum on a titanium plate was used. These two electrodes were arranged such that they faced each other, and an electrolytic solution was injected between them to make a dye-sensitized solar cell. As an electrolytic solution, there was used a solution of 0.1 M of lithium iodide, 0.05 M of iodine, 0.5 M of 1,2-dimethyl-3-n-propylimidazolium iodide and 0.05 M of 4-t-butylpyridine in 3-methoxypropionitrile.

<Evaluations 1-3>

The evaluations 1 to 3 were carried out, and Tables 19 to 21 show the results.

Examples 186-204

Dye-sensitized solar cells were made in the same manner as in Example 185 except that Dye D-7 was changed to dyes shown in Table 19, and they were evaluated. Tables 19 to 21 show the results.

Comparative Examples 45-49

Dye-sensitized solar cells were made in the same manner as in Example 185 except that Dye D-7 was changed to comparative dyes F-23 to F-27, and they were evaluated. Tables 19 to 21 show the results.

[CF55]

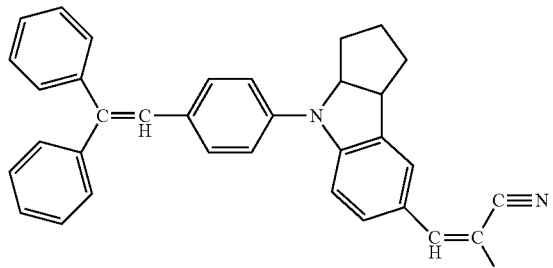

F-23

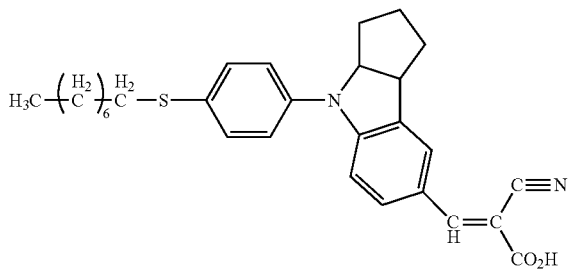

F-24

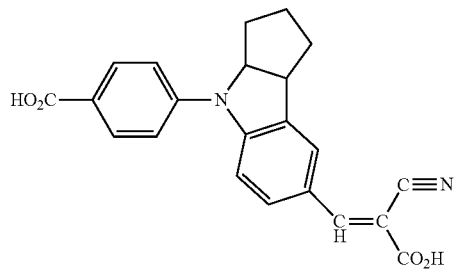

F-25

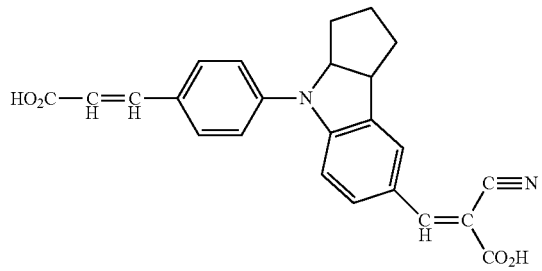

F-26

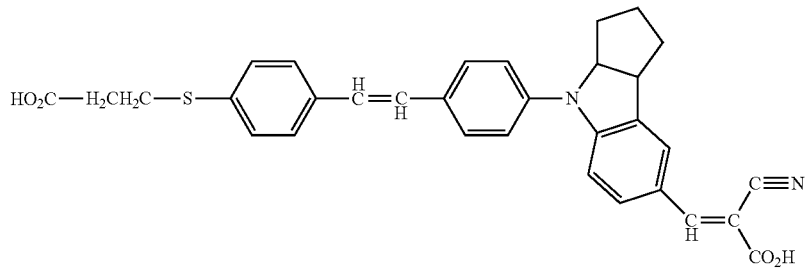

F-27

TABLE 19

| | Dye | Open circuit voltage V | Short circuit current density mA/cm² | Fill factor | Photoelectric conversion efficiency % |
|---|---|---|---|---|---|
| Ex. 185 | D-7 | 0.68 | 7.81 | 0.71 | 3.77 |
| Ex. 186 | D-1 | 0.67 | 7.51 | 0.70 | 3.52 |
| Ex. 187 | D-2 | 0.67 | 7.61 | 0.71 | 3.62 |
| Ex. 188 | D-3 | 0.68 | 7.69 | 0.69 | 3.61 |
| Ex. 189 | D-4 | 0.69 | 7.71 | 0.69 | 3.67 |
| Ex. 190 | D-5 | 0.69 | 7.91 | 0.70 | 3.82 |
| Ex. 191 | D-6 | 0.69 | 7.80 | 0.71 | 3.82 |
| Ex. 192 | D-8 | 0.68 | 7.10 | 0.69 | 3.33 |
| Ex. 193 | D-9 | 0.66 | 8.70 | 0.70 | 4.02 |
| Ex. 194 | D-10 | 0.65 | 9.10 | 0.69 | 4.08 |
| Ex. 195 | D-11 | 0.69 | 9.10 | 0.68 | 4.27 |
| Ex. 196 | D-12 | 0.68 | 9.20 | 0.67 | 4.19 |
| Ex. 197 | D-13 | 0.68 | 7.09 | 0.67 | 3.23 |
| Ex. 198 | D-14 | 0.66 | 6.90 | 0.65 | 2.96 |
| Ex. 199 | D-15 | 0.67 | 7.09 | 0.69 | 3.28 |
| Ex. 200 | D-16 | 0.69 | 7.00 | 0.70 | 3.38 |
| Ex. 201 | D-17 | 0.70 | 7.21 | 0.68 | 3.43 |
| Ex. 202 | D-18 | 0.70 | 7.10 | 0.66 | 3.28 |
| Ex. 203 | D-19 | 0.68 | 7.00 | 0.67 | 3.19 |
| Ex. 204 | D-20 | 0.70 | 6.80 | 0.67 | 3.19 |
| CEx. 45 | F-23 | 0.67 | 9.00 | 0.67 | 4.04 |
| CEx. 46 | F-24 | 0.68 | 9.20 | 0.66 | 4.13 |
| CEx. 47 | F-25 | 0.64 | 7.39 | 0.63 | 2.98 |
| CEx. 48 | F-26 | 0.64 | 7.71 | 0.62 | 3.06 |
| CEx. 49 | F-27 | 0.66 | 10.5 | 0.62 | 4.30 |

Ex. = Example, CEx. = Comparative Example

TABLE 20

| | Dye | Open circuit voltage V | Short circuit current density mA/cm² | Fill factor | Photoelectric conversion efficiency % | Stability ratio of photoelectric conversion efficiency % |
|---|---|---|---|---|---|---|
| Ex. 185 | D-7 | 0.67 | 7.83 | 0.65 | 3.41 | 97 |
| Ex. 186 | D-1 | 0.67 | 7.70 | 0.68 | 3.51 | 97 |
| Ex. 187 | D-2 | 0.68 | 7.39 | 0.70 | 3.52 | 97 |
| Ex. 188 | D-3 | 0.68 | 7.57 | 0.68 | 3.50 | 97 |
| Ex. 189 | D-4 | 0.67 | 7.93 | 0.67 | 3.56 | 97 |
| Ex. 190 | D-5 | 0.68 | 7.82 | 0.69 | 3.67 | 96 |
| Ex. 191 | D-6 | 0.68 | 7.91 | 0.69 | 3.71 | 97 |
| Ex. 192 | D-8 | 0.67 | 7.09 | 0.68 | 3.23 | 97 |
| Ex. 193 | D-9 | 0.65 | 8.82 | 0.68 | 3.90 | 97 |
| Ex. 194 | D-10 | 0.64 | 9.24 | 0.67 | 3.96 | 97 |
| Ex. 195 | D-11 | 0.68 | 9.09 | 0.67 | 4.14 | 97 |
| Ex. 196 | D-12 | 0.67 | 9.47 | 0.64 | 4.06 | 97 |
| Ex. 197 | D-13 | 0.66 | 7.23 | 0.65 | 3.10 | 96 |
| Ex. 198 | D-14 | 0.65 | 7.12 | 0.62 | 2.87 | 97 |
| Ex. 199 | D-15 | 0.66 | 7.12 | 0.67 | 3.15 | 96 |
| Ex. 200 | D-16 | 0.67 | 7.22 | 0.68 | 3.29 | 96 |
| Ex. 201 | D-17 | 0.68 | 7.67 | 0.64 | 3.34 | 97 |
| Ex. 202 | D-18 | 0.68 | 7.23 | 0.64 | 3.15 | 97 |
| Ex. 203 | D-19 | 0.66 | 7.24 | 0.64 | 3.06 | 96 |
| Ex. 204 | D-20 | 0.68 | 7.21 | 0.63 | 3.09 | 97 |
| CEx. 45 | F-23 | 0.66 | 7.42 | 0.66 | 3.23 | 80 |
| CEx. 46 | F-24 | 0.67 | 5.97 | 0.66 | 2.64 | 64 |
| CEx. 47 | F-25 | 0.63 | 5.31 | 0.67 | 2.24 | 75 |
| CEx. 48 | F-26 | 0.63 | 5.93 | 0.64 | 2.39 | 78 |
| CEx. 49 | F-27 | 0.65 | 8.40 | 0.63 | 3.44 | 80 |

Ex. = Example, CEx. = Comparative Example

TABLE 21

| | Dye | Adsorption stability |
|---|---|---|
| Ex. 185 | D-7 | ○ |
| Ex. 186 | D-1 | ○ |
| Ex. 187 | D-2 | ○ |
| Ex. 188 | D-3 | ○ |
| Ex. 189 | D-4 | ○ |
| Ex. 190 | D-5 | ○ |
| Ex. 191 | D-6 | ○ |
| Ex. 192 | D-8 | ○ |
| Ex. 193 | D-9 | ○ |
| Ex. 194 | D-10 | ○ |
| Ex. 195 | D-11 | ○ |
| Ex. 196 | D-12 | ○ |
| Ex. 197 | D-13 | ○ |
| Ex. 198 | D-14 | ○ |
| Ex. 199 | D-15 | ○ |
| Ex. 200 | D-16 | ○ |
| Ex. 201 | D-17 | ○ |
| Ex. 202 | D-18 | ○ |
| Ex. 203 | D-19 | ○ |
| Ex. 204 | D-20 | ○ |
| CEx. 45 | F-23 | Δ |
| CEx. 46 | F-24 | Δ |
| CEx. 47 | F-25 | ○ |
| CEx. 48 | F-26 | ○ |
| CEx. 49 | F-27 | ○ |

Ex. = Example, CEx. = Comparative Example

In Table 19, it is seen that the dyes of this invention each having, as substituents, the first acidic group in the electron acceptor unit and the second acidic group in the electron donor unit exhibit excellent photoelectric conversion efficiency. Further, it is seen that, of the dyes of Comparative Examples, the dyes having the first acidic group in the electron acceptor unit and having no second acidic group (F-23 and F-24) or the dye having the first acidic group in the electron acceptor unit and having an acidic group possessing a pKa of less than 6 bonded through an alkylene group having 2 carbon atoms in the electron donor unit (F-27) exhibit excellent photoelectric conversion efficiency. On the other hand, it is also seen that the dyes having the first acidic group in the electron acceptor unit and an acidic group bonded directly to the sp² carbon atom constituting the π electron conjugated system of the electron donor unit (F-25 and F-26) have low photoelectric conversion efficiency.

In Table 20, it is seen that the dyes of this invention having higher stability ratios of photoelectric conversion efficiency after storage in a 65° C. environment for 14 days than the dyes of Comparative Examples, and hence have excellent durability.

In Table 21, it is seen that the dyes of this invention are excellent in the stability of adsorption to a semiconductor electrode. It is also seen that, of the dyes of Comparative Examples, the dyes F-23 and F-24 are poor in the stability of adsorption to a semiconductor electrode as compared with the dyes of this invention. The dyes F-25 to F-27 are excellent in the stability of adsorption to a semiconductor electrode.

To summarize these results, it is seen that the dyes of this invention have all of high photoelectric conversion efficiency, excellent durability and good adsorption stability.

Example 205

A dye-sensitized solar cell was made in the same manner as in Example 185 except that the concentration of 4-t-butylpyridine in the electrolytic solution was changed to 0.5 M, and evaluated for photoelectric conversion efficiency. Table 22 shows the results. As compared with Example 185, the open circuit voltage changed by +0.05 V, the short circuit current density changed by −0.1 mA/cm², and the fill factor changed by +0.02, and as a result, the photoelectric conversion efficiency was improved by +0.67%.

Examples 206-224

Dye-sensitized solar cells were made in the same manner as in Examples 186 to 204 except that the concentration of 4-t-butylpyridine in an electrolytic solution was changed to 0.5 M, and they were evaluated for photoelectric conversion efficiency. Table 22 shows the results. Table 22 also shows differences in open circuit voltage and photoelectric conversion efficiency from Examples 186 to 204.

Comparative Examples 50-54

Dye-sensitized solar cells were made in the same manner as in Comparative Examples 45 to 49 except that the concentration of 4-t-butylpyridine in an electrolytic solution was changed to 0.5 M, and they were evaluated for photoelectric conversion efficiency. Table 22 shows the results. Table 22 also shows differences in open circuit voltage and photoelectric conversion efficiency from Comparative Examples 45 to 49.

TABLE 22

| | Dye | Open circuit voltage V | Short circuit current density mA/cm² | Fill factor | Photoelectric conversion efficiency % | Difference in open circuit voltage V | Difference in photoelectric conversion efficiency % |
|---|---|---|---|---|---|---|---|
| Ex. 205 | D-7 | 0.73 | 7.70 | 0.79 | 4.44 | +0.05 | +0.67 |
| Ex. 206 | D-1 | 0.72 | 7.50 | 0.72 | 3.89 | +0.05 | +0.37 |
| Ex. 207 | D-2 | 0.72 | 7.50 | 0.72 | 3.89 | +0.05 | +0.27 |
| Ex. 208 | D-3 | 0.73 | 7.59 | 0.70 | 3.88 | +0.05 | +0.27 |
| Ex. 209 | D-4 | 0.74 | 7.71 | 0.71 | 4.05 | +0.05 | +0.35 |
| Ex. 210 | D-5 | 0.74 | 7.60 | 0.72 | 4.05 | +0.05 | +0.23 |
| Ex. 211 | D-6 | 0.74 | 7.70 | 0.72 | 4.10 | +0.05 | +0.28 |
| Ex. 212 | D-8 | 0.73 | 7.01 | 0.70 | 3.58 | +0.05 | +0.25 |
| Ex. 213 | D-9 | 0.71 | 8.61 | 0.71 | 4.34 | +0.05 | +0.32 |
| Ex. 214 | D-10 | 0.70 | 9.00 | 0.70 | 4.41 | +0.05 | +0.33 |
| Ex. 215 | D-11 | 0.74 | 9.11 | 0.69 | 4.65 | +0.05 | +0.38 |
| Ex. 216 | D-12 | 0.72 | 9.10 | 0.69 | 4.52 | +0.04 | +0.33 |
| Ex. 217 | D-13 | 0.73 | 7.01 | 0.70 | 3.58 | +0.05 | +0.35 |
| Ex. 218 | D-14 | 0.70 | 6.80 | 0.66 | 3.14 | +0.04 | +0.18 |
| Ex. 219 | D-15 | 0.72 | 7.00 | 0.71 | 3.58 | +0.05 | +0.30 |
| Ex. 220 | D-16 | 0.74 | 6.91 | 0.72 | 3.68 | +0.05 | +0.30 |
| Ex. 221 | D-17 | 0.75 | 7.09 | 0.70 | 3.72 | +0.05 | +0.29 |
| Ex. 222 | D-18 | 0.74 | 7.00 | 0.68 | 3.52 | +0.04 | +0.24 |
| Ex. 223 | D-19 | 0.73 | 6.91 | 0.69 | 3.48 | +0.05 | +0.29 |
| Ex. 224 | D-20 | 0.75 | 6.71 | 0.68 | 3.42 | +0.05 | +0.23 |
| CEx. 50 | F-23 | 0.70 | 5.91 | 0.66 | 2.73 | +0.04 | −0.50 |
| CEx. 51 | F-24 | 0.71 | 3.69 | 0.66 | 1.73 | +0.04 | −0.91 |
| CEx. 52 | F-25 | 0.67 | 4.89 | 0.65 | 2.13 | +0.04 | −0.11 |
| CEx. 53 | F-26 | 0.66 | 5.51 | 0.63 | 2.29 | +0.03 | −0.10 |
| CEx. 54 | F-27 | 0.69 | 7.88 | 0.64 | 3.48 | +0.04 | +0.04 |

Ex. = Example, CEx. = Comparative Example

As is clear in Table 22, it is seen that when the concentration of 4-t-butylpyridine in an electrolytic solution is increased, the open circuit voltage is improved while nearly maintaining the short circuit current density since the dyes of this invention are excellent in adsorption stability, and as a result, the total photoelectric conversion efficiency is improved. On the other hand, when the dyes of Comparative Examples are used, the open circuit voltage is improved with an increase in the concentration of 4-t-butylpyridine in an electrolytic solution, but the short circuit current density is greatly decreased, and it is seen that as a result, the photoelectric conversion efficiency is decreased or only increased to a slight extent.

Example 225

<Making of Dye-Sensitized Solar Cell>

2 Grams of titanium oxide (trade name: P-25, supplied by NIPPON AEROSIL CO., LTD.), 0.2 g of acetylacetone and 0.3 g of a surfactant (trade name: Triton X-100, supplied by Sigma-Aldrich Co.) were dispersed with a paint conditioner (supplied by Red Devil Inc.) together with 6.5 g of water for 6 hours. Further, to 4.0 g of this dispersion were added 0.2 ml of concentrated nitric acid, 0.4 ml of ethanol and 1.2 g of polyethylene glycol (#20,000), to prepare a paste. The paste was applied to an FTO glass substrate so as to form a layer having a thickness of 6 µm, and the applied paste was dried at room temperature and heated at 100° C. for 1 hour and further at 550° C. for 1 hour to give a semiconductor electrode.

Dye B-12 was dissolved in tetrahydrofuran to prepare a dye solution having a concentration of 0.3 mM. A steroid compound E1 was dissolved in the dye solution such that the dye solution had a steroid compound concentration of 0.6 mM. The above-prepared semiconductor electrode was immersed and so kept in the dye solution at room temperature for 3 hours to carry out adsorption treatment, thereby to make a dye-adsorbed semiconductor electrode (work electrode). As a counter electrode, an electrode obtained by sputtering platinum on a titanium plate was used. These two electrodes were arranged such that they faced each other, and an electrolytic solution was injected between them to make a dye-sensitized solar cell. As an electrolytic solution, there was used a solution of 0.1 M of lithium iodide, 0.05 M of iodine, 0.5 M of 1,2-dimethyl-3-n-propylimidazolium iodide and 0.05 M of 4-t-butylpyridine in 3-methoxypropionitrile.

<Evaluations 1-3>

The evaluations 1 to 3 were carried out, and Tables 23 to 25 show the results.

Example 226

Dye D-9 was dissolved in tetrahydrofuran to prepare a dye solution having a concentration of 0.3 mM. A semiconductor electrode that was made in the same manner as in Example 225 was immersed and so kept in the dye solution at room temperature for 3 hours to carry out adsorption treatment, thereby to make a dye-adsorbed semiconductor electrode (work electrode). As a counter electrode, an electrode obtained by sputtering platinum on a titanium plate was used. These two electrodes were arranged such that they faced each other, and an electrolytic solution was injected between them to make a dye-sensitized solar cell. As an electrolytic solution, there was used a solution of 0.1 M of lithium iodide, 0.05 M of iodine, 0.5 M of 1,2-dimethyl-3-n-propylimidazolium iodide and 0.05 M of 4-t-butylpyridine in 3-methoxypropionitrile.

<Evaluations 1-3>

The evaluations 1 to 3 were carried out, and Tables 23 to 25 show the results.

Comparative Examples 55-56

Dye-sensitized solar cells were made in the same manner as in Example 225 except that Dye B-12 was changed to a comparative dye F-28 or F-29, and they were evaluated. Tables 23 to 25 show the results.

Comparative Examples 57-58

Dye-sensitized solar cells were made in the same manner as in Example 226 except that Dye D-9 was changed to a comparative dye F-30 or F-31, and they were evaluated. Tables 23 to 25 show the results.

[CF56]

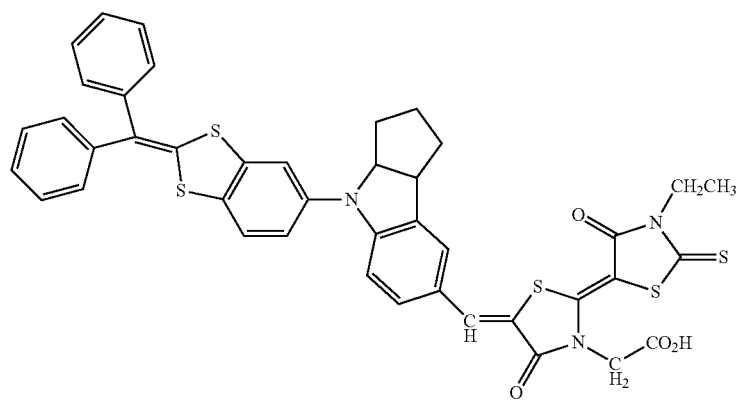

F-28

-continued

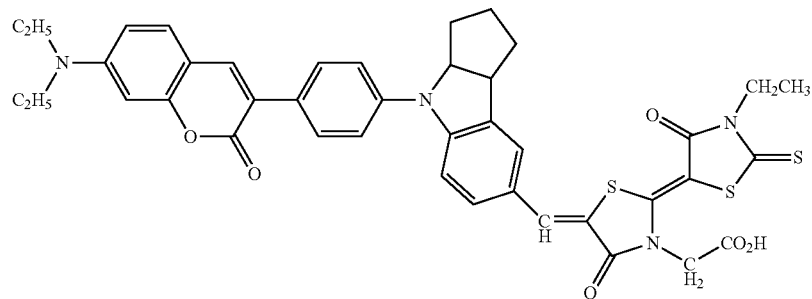
F-29

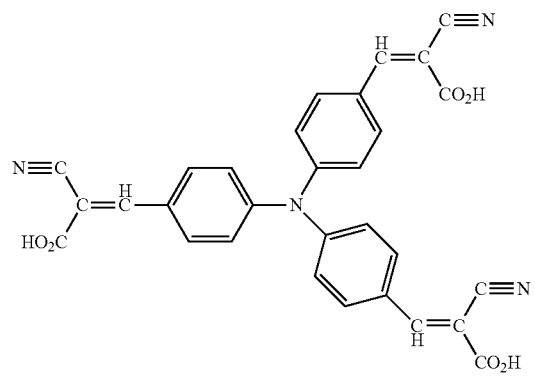
F-30

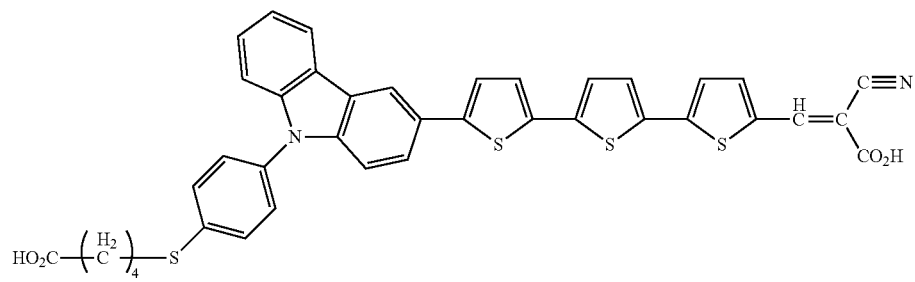
F-31

TABLE 23

| | Dye | Open circuit voltage V | Short circuit current density mA/cm² | Fill factor | Photoelectric conversion efficiency % |
|---|---|---|---|---|---|
| Example 225 | B-12 | 0.72 | 12.8 | 0.71 | 6.54 |
| Comparative Example 55 | F-28 | 0.71 | 11.0 | 0.70 | 5.47 |
| Comparative Example 56 | F-29 | 0.70 | 10.9 | 0.69 | 5.26 |
| Example 226 | D-9 | 0.64 | 8.46 | 0.70 | 3.79 |
| Comparative Example 57 | F-30 | 0.68 | 4.93 | 0.65 | 2.18 |
| Comparative Example 58 | F-31 | 0.70 | 6.94 | 0.69 | 3.35 |

TABLE 24

| | Dye | Open circuit voltage V | Short circuit current density mA/cm² | Fill factor | Photoelectric conversion efficiency % | Stability ratio of photoelectric conversion efficiency % |
|---|---|---|---|---|---|---|
| Ex. 225 | B-12 | 0.72 | 12.4 | 0.71 | 6.34 | 97 |
| CEx. 55 | F-28 | 0.70 | 8.29 | 0.66 | 3.83 | 70 |
| CEx. 56 | F-29 | 0.67 | 7.61 | 0.66 | 3.37 | 64 |
| Ex. 226 | D-9 | 0.64 | 8.21 | 0.70 | 3.68 | 97 |
| CEx. 57 | F-30 | 0.63 | 4.19 | 0.61 | 1.61 | 74 |
| CEx. 58 | F-31 | 0.68 | 6.00 | 0.64 | 2.61 | 78 |

Ex. = Example, CEx. = Comparative Example

TABLE 25

| | Dye | Adsorption stability |
|---|---|---|
| Example 225 | B-12 | ◯ |
| Comparative Example 55 | F-28 | Δ |
| Comparative Example 56 | F-29 | Δ |

TABLE 25-continued

| Dye | Adsorption stability |
|---|---|---|
| Example 226 | D-9 | ○ |
| Comparative Example 57 | F-30 | ○ |
| Comparative Example 58 | F-31 | ○ |

In Table 23, it is seen that the dyes of this invention exhibit excellent photoelectric conversion efficiency over the dyes of Comparative Examples (comparisons of B-12 with F-28 and F-29 and comparisons of D-9 with F-30 and F-31).

In Table 24, it is seen that the dyes of this invention have higher stability ratios of photoelectric conversion efficiency after storage in a 65° C. environment for 14 days than the dyes of Comparative Examples and have excellent durability.

In Table 25, it is seen that the dyes of this invention are also excellent in the stability of adsorption to a semiconductor electrode. It is also seen that, of the dyes of Comparative Examples, the dyes having only one acidic group possessing a pKa of less than 6 in the electron acceptor unit (F-28 and F-29) are poor in the stability of adsorption to a semiconductor electrode as compared with the dyes of this invention. The dyes having a plurality of acidic groups possessing a pKa of less than 6 (F-30 and F-31) are excellent in adsorption stability.

To summarize these results, the dyes of this invention have all of high photoelectric conversion efficiency, excellent durability and good adsorption stability.

A dye-sensitized solar cell was made in the same manner as in Example 225 except that the concentration of 4-t-butylpyridine in the electrolytic solution was changed to 0.5 M, and evaluated for photoelectric conversion efficiency. Table 26 shows the results. As compared with Example 225, the open circuit voltage changed by +0.05 V, the short circuit current density changed by −0.1 mA/cm², and the fill factor changed by +0.01, and as a result, the photoelectric conversion efficiency was improved by +0.50%.

Example 228

A dye-sensitized solar cell was made in the same manner as in Example 226 except that the concentration of 4-t-butylpyridine in the electrolytic solution was changed to 0.5 M, and it was evaluated for photoelectric conversion efficiency. Table 26 shows the result. Table 26 also shows differences in open circuit voltage and photoelectric conversion efficiency from Example 226.

Comparative Examples 59-62

Dye-sensitized solar cells were made in the same manner as in Comparative Examples 55 to 58 except that the concentration of 4-t-butylpyridine in the electrolytic solution was changed to 0.5 M, and they were evaluated for photoelectric conversion efficiency. Table 26 shows the results. Table 28 also shows differences in open circuit voltage and photoelectric conversion efficiency from Comparative Examples 55 to 58.

TABLE 26

| Dye | Open circuit voltage V | Short circuit current density mA/cm² | Fill factor | Photoelectric conversion efficiency % | Difference in open circuit voltage V | Difference in photoelectric conversion efficiency % |
|---|---|---|---|---|---|---|
| Ex. 227 | B-12 | 0.77 | 12.7 | 0.72 | 7.04 | +0.05 | +0.50 |
| CEx. 59 | F-28 | 0.76 | 7.72 | 0.66 | 3.87 | +0.05 | −1.60 |
| CEx. 60 | F-29 | 0.74 | 6.83 | 0.61 | 3.08 | +0.04 | −2.18 |
| Ex. 228 | D-9 | 0.69 | 8.42 | 0.72 | 4.18 | +0.05 | +0.39 |
| CEx. 61 | F-30 | 0.72 | 4.81 | 0.62 | 2.15 | +0.04 | −0.03 |
| CEx. 62 | F-31 | 0.75 | 6.71 | 0.67 | 3.37 | +0.05 | +0.02 |

Ex. = Example, CEx. = Comparative Example

As is clear in Table 26, it is seen that when the concentration of 4-t-butylpyridine in an electrolytic solution is increased, the open circuit voltage is improved while nearly maintaining the short circuit current density since the dyes of this invention are excellent in adsorption stability, and as a result, the total photoelectric conversion efficiency is improved. On the other hand, when the dyes of Comparative Examples are used, the open circuit voltage is improved with an increase in the concentration of 4-t-butylpyridine in the electrolytic solution, but the short circuit current density is greatly decreased, and it is seen that as a result, the photoelectric conversion efficiency is decreased or only increased to a slight extent.

Industrial Utility

The dye for a dye-sensitized solar cell, provide by this invention, can be applied not only to a dye-sensitized solar cell but also to a photosensor sensitive to light having a specific wavelength, etc.

The invention claimed is:

1. A dye for a dye-sensitized solar cell, represented by the Formula [II],

[CF2]

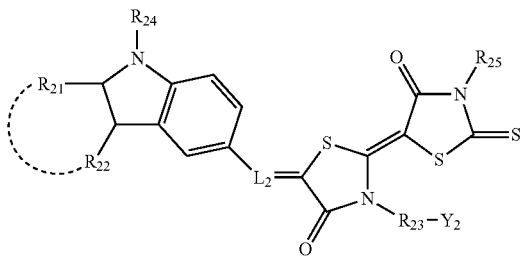

[II]

wherein each of $R_{21}$ and $R_{22}$ represents a hydrogen atom or an alkyl group, or $R_{21}$ and $R_{22}$ may be bonded to each other and form a cyclopentane ring or a cyclohexane ring, $R_{23}$ represents an alkylene group having 1 to 3 carbon atoms, $Y_2$ represents an acidic group possessing a pKa of less than 6, $R_{24}$ represents an aliphatic hydrocarbon residue, an aromatic hydrocarbon residue or a heterocyclic ring residue, $R_{25}$ represents an alkyl group or an aralkyl group, provided that at least one of $R_{24}$ and $R_{25}$ represents a group of the following formula, —$(CH_2)_n$—Y in which n is an integer of 4 to 23 and Y is an acidic group possessing a pKa of less than 6, $L_2$ represents a conjugated methine group, and a steric configuration of two heterocyclic five-membered rings containing a sulfur atom each may be any one of Z-configuration and E-configuration.

2. A semiconductor electrode comprising the dye for a dye-sensitized solar cell recited in claim 1.

3. A dye-sensitized solar cell comprising the semiconductor electrode recited in claim 2.

* * * * *